US011317883B2

(12) United States Patent
Min

(10) Patent No.: US 11,317,883 B2
(45) Date of Patent: May 3, 2022

(54) SYSTEMS AND METHODS OF CHARACTERIZING HIGH RISK PLAQUES

(71) Applicant: Cleerly, Inc., New York, NY (US)

(72) Inventor: James K. Min, Brooklyn, NY (US)

(73) Assignee: CLEERLY, INC., Denver, CO (US)

( * ) Notice: Subject to any disclaimer, the term of this patent is extended or adjusted under 35 U.S.C. 154(b) by 0 days.

(21) Appl. No.: 17/461,587

(22) Filed: Aug. 30, 2021

(65) Prior Publication Data

US 2021/0386390 A1 Dec. 16, 2021

Related U.S. Application Data

(63) Continuation of application No. 17/033,136, filed on Sep. 25, 2020, which is a continuation of application
(Continued)

(51) Int. Cl.
*A61B 6/00* (2006.01)
*A61B 6/03* (2006.01)
*G06T 7/00* (2017.01)

(52) U.S. Cl.
CPC .............. *A61B 6/504* (2013.01); *A61B 6/032* (2013.01); *A61B 6/5217* (2013.01);
(Continued)

(58) Field of Classification Search
CPC .................... G06T 7/0012; G06T 7/97; G06T 2207/30101; G06T 2207/10028;
(Continued)

(56) References Cited

U.S. PATENT DOCUMENTS 4,945,478 A 7/1990 Merickel et al.
5,722,408 A 3/1998 Dehner et al.
(Continued)

FOREIGN PATENT DOCUMENTS

CA 2368390 C 7/2010
EP 3431005 A1 1/2019
(Continued)

OTHER PUBLICATIONS

Dey, Damini, et al. "Integrated prediction of lesion-specific ischaemia from quantitative coronary CT angiography using machine learning: a multicentre study." European radiology 28.6 (2018): 2655-2664. (Year: 2018).*
(Continued)

*Primary Examiner* — Vu Le
*Assistant Examiner* — Tracy Mangialaschi
(74) *Attorney, Agent, or Firm* — Knobbe, Martens, Olson & Bear LLP

(57) ABSTRACT

A method for characterization of coronary plaque tissue data and perivascular tissue data using image data gathered from a computed tomography (CT) scan along a blood vessel, the image information including radiodensity values of coronary plaque and perivascular tissue located adjacent to the coronary plaque, the method comprising quantifying radiodensity in regions of coronary plaque, quantifying, radiodensity in at least one region of corresponding perivascular tissue adjacent to the coronary plaque, determining gradients of the quantified radiodensity values within the coronary plaque and the quantified radiodensity values within the corresponding perivascular tissue, and determining a ratio of the quantified radiodensity values within the coronary plaque and the corresponding perivascular tissue; and characterizing the coronary plaque by analyzing a gradient of the quantified radiodensity values in the coronary plaque and the corresponding perivascular, and/or the ratio of the coronary plaque radiodensity values and the radiodensity values of the corresponding perivascular tissue.

30 Claims, 21 Drawing Sheets

Related U.S. Application Data

No. 16/750,278, filed on Jan. 23, 2020, now Pat. No. 10,813,612.

(60) Provisional application No. 62/797,024, filed on Jan. 25, 2019.

(52) U.S. Cl.
CPC .......... *A61B 6/5223* (2013.01); *G06T 7/0012* (2013.01); *G06T 7/97* (2017.01); *G06T 2207/10028* (2013.01); *G06T 2207/10072* (2013.01); *G06T 2207/30101* (2013.01)

(58) Field of Classification Search
CPC ........ G06T 2207/10072; A61B 6/5217; A61B 6/032; A61B 6/504; A61B 6/5223
See application file for complete search history.

(56) References Cited

U.S. PATENT DOCUMENTS

| | | | |
|---|---|---|---|
| 5,891,030 | A | 4/1999 | Johnson et al. |
| 6,047,080 | A | 4/2000 | Chen et al. |
| 6,591,004 | B1 | 7/2003 | VanEssen et al. |
| 7,535,986 | B2 | 5/2009 | Hempel |
| 7,558,611 | B2 | 7/2009 | Arnold et al. |
| 7,570,983 | B2 | 8/2009 | Becker et al. |
| 7,711,165 | B2 | 5/2010 | Lesage et al. |
| 7,715,626 | B2 | 5/2010 | Florin et al. |
| 7,805,385 | B2 | 9/2010 | Steck et al. |
| 7,813,549 | B2 | 10/2010 | Buelow et al. |
| 7,840,062 | B2 | 11/2010 | Boroczky et al. |
| 7,860,283 | B2 | 12/2010 | Begelman et al. |
| 7,899,764 | B2 | 3/2011 | Martin et al. |
| 7,904,977 | B1 | 3/2011 | Singh |
| 7,912,528 | B2 | 3/2011 | Krishnan et al. |
| 7,940,974 | B2 | 5/2011 | Skinner et al. |
| 7,940,977 | B2 | 5/2011 | Begelman et al. |
| 7,953,266 | B2 | 5/2011 | Gulsun et al. |
| 7,993,274 | B2 | 8/2011 | Pruvot et al. |
| 8,046,488 | B2 | 10/2011 | Cherukuri et al. |
| 8,068,894 | B2 | 11/2011 | Huizenga et al. |
| 8,144,949 | B2 | 3/2012 | Simon et al. |
| 8,200,466 | B2 | 6/2012 | Spiker et al. |
| 8,386,188 | B2 | 2/2013 | Taylor et al. |
| 8,526,699 | B2 | 9/2013 | Mittal et al. |
| 8,582,854 | B2 | 11/2013 | Zhang et al. |
| 8,605,979 | B2 | 12/2013 | Arnold et al. |
| 8,774,479 | B2 | 7/2014 | Madabhushi et al. |
| 8,777,854 | B2 | 7/2014 | Patwardhan et al. |
| 8,885,905 | B2 | 11/2014 | Dey et al. |
| 8,938,106 | B2 | 1/2015 | Aulbach et al. |
| 9,008,392 | B1 | 4/2015 | Bai et al. |
| 9,058,692 | B1 | 6/2015 | Grady et al. |
| 9,070,214 | B1 | 6/2015 | Grady et al. |
| 9,081,721 | B1 | 7/2015 | Grady et al. |
| 9,129,417 | B2 | 9/2015 | Zheng et al. |
| 9,155,512 | B2 | 10/2015 | Choi et al. |
| 9,159,159 | B2 | 10/2015 | Bai et al. |
| 9,195,801 | B1 | 11/2015 | Sankaran et al. |
| 9,220,418 | B2 | 12/2015 | Choi et al. |
| 9,220,419 | B2 | 12/2015 | Choi et al. |
| 9,235,887 | B2 | 1/2016 | Bucker et al. |
| 9,239,905 | B1 | 1/2016 | Sankaran et al. |
| 9,280,639 | B2 | 3/2016 | Sankaran et al. |
| 9,295,397 | B2 | 3/2016 | Liu et al. |
| 9,295,429 | B2 | 3/2016 | Ong et al. |
| 9,378,580 | B2 | 6/2016 | Grady et al. |
| 9,430,827 | B2 | 8/2016 | Kelm et al. |
| 9,538,925 | B2 | 1/2017 | Sharma et al. |
| 9,610,272 | B2 | 4/2017 | Soni |
| 9,642,586 | B2 | 5/2017 | Kelm et al. |
| 9,649,171 | B2 | 5/2017 | Sankaran et al. |
| 9,655,563 | B2 | 5/2017 | Liu et al. |
| 9,700,219 | B2 | 7/2017 | Sharma et al. |
| 9,721,340 | B2 | 8/2017 | Gillies et al. |
| 9,761,004 | B2 | 9/2017 | Mittal et al. |
| 9,767,557 | B1 | 9/2017 | Gulsun et al. |
| 9,770,303 | B2 | 9/2017 | Choi et al. |
| 9,785,748 | B2 | 10/2017 | Koo et al. |
| 9,805,463 | B2 | 10/2017 | Choi et al. |
| 9,805,470 | B2 | 10/2017 | Bhatia et al. |
| 9,836,653 | B2 | 12/2017 | Schnittman |
| 9,839,399 | B2 | 12/2017 | Fonte et al. |
| 9,839,484 | B2 | 12/2017 | Taylor |
| 9,881,372 | B2 | 1/2018 | Gulsun et al. |
| 9,965,891 | B2 | 5/2018 | Grady et al. |
| 10,078,124 | B2 | 9/2018 | Horkay et al. |
| 10,082,553 | B2 | 9/2018 | Boss |
| 10,170,206 | B2 | 1/2019 | Koo et al. |
| 10,176,408 | B2 | 1/2019 | Paik et al. |
| 10,398,331 | B2 | 9/2019 | Relan |
| 10,456,094 | B2 | 10/2019 | Fonte et al. |
| 10,478,130 | B2 | 11/2019 | Sharma et al. |
| 10,483,006 | B2 | 11/2019 | Itu et al. |
| 10,498,755 | B2 | 12/2019 | Harris |
| 10,517,677 | B2 | 12/2019 | Sankaran et al. |
| 10,776,988 | B2 | 9/2020 | Grady et al. |
| 10,813,612 | B2 | 10/2020 | Min |
| 10,871,536 | B2 | 12/2020 | Golden et al. |
| 10,939,828 | B2 | 3/2021 | Fonte et al. |
| 10,939,960 | B2 | 3/2021 | Choi et al. |
| 10,945,606 | B2 | 3/2021 | Sanders et al. |
| 10,951,715 | B2 | 3/2021 | Hart et al. |
| 10,964,071 | B2 | 3/2021 | Grady et al. |
| 10,966,619 | B2 | 4/2021 | Fonte et al. |
| 10,973,583 | B2 | 4/2021 | Taylor et al. |
| 10,978,210 | B2 | 4/2021 | Grady et al. |
| 10,984,535 | B2 | 4/2021 | Grady et al. |
| 10,987,010 | B2 | 4/2021 | Grady et al. |
| 10,990,652 | B2 | 4/2021 | Tayler et al. |
| 10,991,465 | B2 | 4/2021 | Grady |
| 11,013,425 | B2 | 5/2021 | Fonte et al. |
| 11,017,904 | B2 | 5/2021 | Sankaran et al. |
| 11,033,332 | B2 | 6/2021 | Taylor |
| 11,042,822 | B2 | 6/2021 | Sankaran et al. |
| 11,071,501 | B2 | 7/2021 | Buckler et al. |
| 11,083,524 | B2 | 8/2021 | Taylor |
| 11,087,459 | B2 | 8/2021 | Buckler et al. |
| 11,087,460 | B2 | 8/2021 | Buckler et al. |
| 11,087,884 | B2 | 8/2021 | Sankaran et al. |
| 11,090,118 | B2 | 8/2021 | Taylor |
| 11,094,058 | B2 | 8/2021 | Buclker et al. |
| 11,094,060 | B1 | 8/2021 | Min et al. |
| 11,094,061 | B1 | 9/2021 | Min et al. |
| 11,113,811 | B2 | 9/2021 | Min et al. |
| 11,113,812 | B2 | 9/2021 | Buckler et al. |
| 11,116,575 | B2 | 9/2021 | Taylor |
| 11,120,312 | B2 | 9/2021 | Buckler et al. |
| 11,120,549 | B2 | 9/2021 | Min et al. |
| 11,120,550 | B2 | 9/2021 | Min et al. |
| 11,120,893 | B2 | 9/2021 | Choi et al. |
| 11,127,503 | B2 | 9/2021 | Rabbat et al. |
| 11,135,012 | B2 | 10/2021 | Taylor |
| 11,138,337 | B2 | 10/2021 | Yousfi et al. |
| 11,154,361 | B2 | 10/2021 | Taylor |
| 11,185,368 | B2 | 11/2021 | Spilker et al. |
| 11,210,786 | B2 | 12/2021 | Min et al. |
| 11,232,564 | B2 | 1/2022 | Min et al. |
| 11,238,587 | B2 | 2/2022 | Min et al. |
| 11,244,451 | B1 | 2/2022 | Min et al. |
| 2004/0101181 | A1 | 5/2004 | Giger et al. |
| 2004/0133094 | A1 | 7/2004 | Becker et al. |
| 2004/0136491 | A1 | 7/2004 | Iatrou et al. |
| 2005/0043614 | A1 | 2/2005 | Huizenga et al. |
| 2005/0110791 | A1 | 5/2005 | Krishnamoorthy et al. |
| 2005/0118632 | A1 | 6/2005 | Chen et al. |
| 2006/0036167 | A1 | 2/2006 | Shina |
| 2006/0101075 | A1 | 5/2006 | Lehel et al. |
| 2007/0018558 | A1 | 1/2007 | Chua et al. |
| 2007/0019778 | A1 | 1/2007 | Clouse et al. |
| 2007/0248250 | A1 | 10/2007 | Gulsun et al. |
| 2007/0260141 | A1 | 11/2007 | Margolis et al. |
| 2008/0100621 | A1 | 5/2008 | Aharon et al. |

(56) References Cited

U.S. PATENT DOCUMENTS

| | | |
|---|---|---|
| 2008/0103389 A1 | 5/2008 | Begelman et al. |
| 2008/0119734 A1 | 5/2008 | Pruvot et al. |
| 2008/0187199 A1 | 8/2008 | Gulsun et al. |
| 2008/0188962 A1 | 8/2008 | Suryanarayanan et al. |
| 2009/0012382 A1 | 1/2009 | Dutta et al. |
| 2009/0016588 A1 | 1/2009 | Slabaugh et al. |
| 2009/0129673 A1 | 5/2009 | Simon et al. |
| 2009/0276161 A1 | 11/2009 | Cobain |
| 2009/0278846 A1 | 11/2009 | Gulsun et al. |
| 2010/0137711 A1 | 6/2010 | Hamilton et al. |
| 2010/0177945 A1 | 7/2010 | Moriya |
| 2010/0201786 A1 | 8/2010 | Schaefer et al. |
| 2010/0316274 A1 | 12/2010 | Langheinrich et al. |
| 2011/0026798 A1 | 2/2011 | Madabhushi et al. |
| 2011/0116697 A1 | 5/2011 | Dafni et al. |
| 2011/0206247 A1 | 8/2011 | Dachille et al. |
| 2011/0229002 A1 | 9/2011 | Arnold et al. |
| 2011/0245650 A1 | 10/2011 | Kerwin et al. |
| 2012/0041323 A1 | 2/2012 | Taylor et al. |
| 2012/0076377 A1 | 3/2012 | Dutta et al. |
| 2012/0128132 A1 | 5/2012 | Coolens et al. |
| 2012/0158432 A1 | 6/2012 | Jain |
| 2012/0243764 A1 | 9/2012 | Dey et al. |
| 2012/0263368 A1 | 10/2012 | Nakano et al. |
| 2013/0101187 A1 | 4/2013 | Sundar et al. |
| 2013/0190592 A1 | 7/2013 | Coppini et al. |
| 2013/0190595 A1 | 7/2013 | Oraevsky et al. |
| 2013/0246034 A1 | 9/2013 | Sharma et al. |
| 2014/0058715 A1 | 2/2014 | Sharma et al. |
| 2014/0073976 A1 | 3/2014 | Fonte et al. |
| 2014/0114176 A1 | 4/2014 | Hirschenbain et al. |
| 2015/0016702 A1 | 1/2015 | Huizenga et al. |
| 2015/0065846 A1 | 3/2015 | Choi |
| 2015/0066818 A1 | 3/2015 | Choi et al. |
| 2015/0187025 A1 | 7/2015 | Wasserkrug et al. |
| 2015/0193944 A1 | 7/2015 | Lang et al. |
| 2016/0066861 A1 | 3/2016 | Taylor |
| 2016/0078309 A1 | 3/2016 | Feldman |
| 2016/0104281 A1 | 4/2016 | Grady et al. |
| 2016/0203263 A1 | 7/2016 | Maier et al. |
| 2016/0292372 A1 | 10/2016 | Kamen et al. |
| 2016/0296288 A1 | 10/2016 | Sankaran et al. |
| 2016/0300350 A1 | 10/2016 | Choi et al. |
| 2016/0346043 A1 | 12/2016 | Jaquet et al. |
| 2017/0014034 A1 | 1/2017 | Koo et al. |
| 2017/0018081 A1 | 1/2017 | Taylor et al. |
| 2017/0046484 A1 | 2/2017 | Buckler et al. |
| 2017/0103525 A1 | 4/2017 | Hu et al. |
| 2017/0119333 A1 | 5/2017 | Zebaze et al. |
| 2017/0202621 A1 | 7/2017 | Taylor |
| 2017/0245821 A1 | 8/2017 | Itu et al. |
| 2017/0265831 A1 | 9/2017 | Sankaran et al. |
| 2017/0265832 A1* | 9/2017 | Antoniades ............ A61B 6/504 |
| 2017/0337343 A1 | 11/2017 | Kakadiaris et al. |
| 2017/0340393 A1 | 11/2017 | Choi et al. |
| 2018/0165811 A1 | 6/2018 | Flohr et al. |
| 2018/0179189 A1 | 6/2018 | MacPhee et al. |
| 2018/0225847 A1 | 8/2018 | Grady et al. |
| 2018/0243033 A1 | 8/2018 | Tran et al. |
| 2018/0330477 A1 | 11/2018 | Paik et al. |
| 2019/0074082 A1 | 3/2019 | Buckler et al. |
| 2019/0110776 A1 | 4/2019 | Yu et al. |
| 2019/0159737 A1 | 5/2019 | Buckler et al. |
| 2019/0172197 A1 | 6/2019 | Buckler et al. |
| 2019/0174082 A1 | 6/2019 | Taruki et al. |
| 2019/0175130 A1 | 6/2019 | Raman et al. |
| 2019/0180153 A1 | 6/2019 | Buckler et al. |
| 2019/0180438 A1 | 6/2019 | Buckler et al. |
| 2019/0244347 A1 | 8/2019 | Buckler et al. |
| 2019/0244348 A1 | 8/2019 | Buckler et al. |
| 2019/0251713 A1 | 8/2019 | Chen et al. |
| 2019/0350538 A1 | 11/2019 | Wilson et al. |
| 2020/0069262 A1 | 3/2020 | Fonte et al. |
| 2020/0085501 A1 | 3/2020 | Sankaran et al. |
| 2020/0237329 A1 | 7/2020 | Min |
| 2020/0273579 A1 | 8/2020 | Wright |
| 2020/0372701 A1 | 11/2020 | Grady et al. |
| 2021/0007807 A1 | 1/2021 | Sankaran et al. |
| 2021/0030478 A1 | 2/2021 | Hart et al. |
| 2021/0042918 A1 | 2/2021 | Bucker |
| 2021/0042927 A1 | 2/2021 | Amis et al. |
| 2021/0074435 A1 | 3/2021 | Taylor et al. |
| 2021/0077196 A1 | 3/2021 | Jaquet et al. |
| 2021/0082579 A1 | 3/2021 | Grady et al. |
| 2021/0093384 A1 | 4/2021 | Grady et al. |
| 2021/0153749 A1 | 5/2021 | Fonte et al. |
| 2021/0153945 A1 | 5/2021 | Choi et al. |
| 2021/0185131 A1 | 6/2021 | Hart et al. |
| 2021/0186448 A1 | 6/2021 | Min |
| 2021/0196391 A1 | 7/2021 | Taylor et al. |
| 2021/0202110 A1 | 7/2021 | Grady et al. |
| 2021/0209757 A1 | 7/2021 | Min et al. |
| 2021/0210209 A1 | 7/2021 | Taylor et al. |
| 2021/0217165 A1 | 7/2021 | Min et al. |
| 2021/0217534 A1 | 7/2021 | Rabbat et al. |
| 2021/0225006 A1 | 7/2021 | Grady et al. |
| 2021/0228094 A1 | 7/2021 | Grady et al. |
| 2021/0241455 A1 | 8/2021 | Min et al. |
| 2021/0241920 A1 | 8/2021 | Sankaran et al. |
| 2021/0244475 A1 | 8/2021 | Taylor |
| 2021/0267690 A1 | 9/2021 | Taylor |
| 2021/0272030 A1 | 9/2021 | Sankaran et al. |
| 2021/0282719 A1 | 9/2021 | Buckler et al. |
| 2021/0282860 A1 | 9/2021 | Taylor |
| 2021/0312622 A1 | 10/2021 | Buckler et al. |
| 2021/0319558 A1 | 10/2021 | Min et al. |
| 2021/0322102 A1 | 10/2021 | Sankaran et al. |
| 2021/0334961 A1 | 10/2021 | Min et al. |
| 2021/0334962 A1 | 10/2021 | Min et al. |
| 2021/0334966 A1 | 10/2021 | Min et al. |
| 2021/0335497 A1 | 10/2021 | Sankaran et al. |
| 2021/0338333 A1 | 11/2021 | Sankaran et al. |
| 2021/0343010 A1 | 11/2021 | Min et al. |
| 2021/0358634 A1 | 11/2021 | Sankaran et al. |
| 2021/0358635 A1 | 11/2021 | Sankaran et al. |
| 2021/0366111 A1 | 11/2021 | Min et al. |
| 2021/0366112 A1 | 11/2021 | Min et al. |
| 2021/0366113 A1 | 11/2021 | Min et al. |
| 2021/0366114 A1 | 11/2021 | Min et al. |
| 2021/0366115 A1 | 11/2021 | Min et al. |
| 2021/0374969 A1 | 12/2021 | Grady et al. |
| 2021/0375401 A1 | 12/2021 | Choi et al. |
| 2021/0375476 A1 | 12/2021 | Rabbat et al. |
| 2021/0390689 A1 | 12/2021 | Buckler et al. |
| 2021/0397746 A1 | 12/2021 | Yousfi et al. |

FOREIGN PATENT DOCUMENTS

| | | |
|---|---|---|
| FR | 2908976 A1 | 5/2008 |
| JP | 2003-150703 | 5/2003 |
| JP | 5305821 B2 | 10/2013 |
| JP | 6203410 B2 | 9/2017 |
| WO | WO 2009/105530 | 8/2009 |
| WO | WO 2010/067276 | 6/2010 |
| WO | WO 2014/107402 | 7/2014 |
| WO | WO 2015/095282 | 6/2015 |
| WO | WO 2016/022533 | 2/2016 |
| WO | WO 2016/024128 | 2/2016 |
| WO | WO 2017/011555 | 1/2017 |
| WO | WO 2017/096407 | 6/2017 |
| WO | WO 2017/106819 | 6/2017 |
| WO | WO 2019/033098 | 2/2019 |
| WO | WO 19/242227 | 12/2019 |
| WO | WO 2021/141921 | 7/2021 |

OTHER PUBLICATIONS

Sabir, Adeel, et al. "Measuring noncalcified coronary atherosclerotic plaque using voxel analysis with MDCT angiography: phantom validation." American Journal of Roentgenology 190.4 (2008): W242-W246. (Year: 2008).*

Obaid, Daniel R., et al. "Atherosclerotic Plaque Composition and Classification Identified by Coronary Computed Tomography: Assess-

(56) References Cited

OTHER PUBLICATIONS ment of CT-Generated Plaque Maps Compared with Virtual Histology Intravascular Ultrasound and Histology." Circulation: Cardiovascular Imaging 6.5 (2013): 655-664. (Year: 2013).*
Mancio, Jennifer, Evangelos K. Oikonomou, and Charalambos Antoniades. "Perivascular adipose tissue and coronary atherosclerosis." Heart 104.20 (2018): 1654-1662. (Year: 2018).*
Okubo, Ryo, et al. "Pericoronary adipose tissue ratio is a stronger associated factor of plaque vulnerability than epicardial adipose tissue on coronary computed tomography angiography." Heart and vessels 32.7 (2017): 813-822. (Year: 2017).*
Ahmadi et al., "Association of Coronary Stenosis and Plaque Morphology with Fractional Flow Reserve and Outcomes." JAMA cardiology 2016; 1 (3): 350-7. doi: 10.1001/jamacardio.2016.0263 [published Online First: Jul. 22, 2016].
International Preliminary Report on Patentability for Application No. PCT/US2020/015035 dated Jul. 27, 2021, in 7 pages.
International Search Report and Written Opinion for Application No. PCT/US2021/037919 dated Oct. 6, 2021, in 12 pages.
Abbara et al., "SCCT Guidelines for the performance and acquisition of coronary computed tomographic angiography: A report of the society of Cardiovascular Computed Tomography Guidelines Committee: Endorsed by the North American Society for Cardiovascular Imaging (NASCI)." Journal of cardiovascular computed tomography 2016; 10(6) pp. 435-449.
Achenbach et al. "Detection of calcified and noncalcified coronary atherosclerotic plaque by contrast-enhanced, submillimeter multidetector spiral computed tomography: a segment-based comparison with intravascular ultrasound." Circulation 2004; 109(1) pp. 14-17.
Ahmadi A. et al. "Do Plaques rapidly progress prior to myocardial infarction? The interplay between plaque vunerability and progression." Circ Res. 2015; 117(1), pp. 99-104.
Ahmadi et al., "Lesion-Specific and Vessel-Related Determinants of Fractional Flow Reserve Beyond Coronary Artery Stenosis", JACCL Cardiovascular Imaging, vol. 11, No. 4. 2018 pp. 521-530.
Antonopoulos et al., "Detecting Human coronary inflammation by imaging perivascular fat", Sci. Transl. Med. 9, eaal2658 (2017) Jul. 12, 2017.
Al'Aref et al. "Clinical Applications of machine learning in cardiovascular disease and its relevance to cardiac imaging." Eur Heart J. Jul. 27, 2018. [Epub ahead of print].
Al'Aref et al., "High-risk atherosclerotic plaque features for cardiovascular risk assessment in the Prospective Multicenter Imaging Study for Evaluation of Chest Pain trial", Cardiovascular Diagnosis and Therapy, vol. 9, No. 1, Feb. 2019. pp. 89-93.
Arbab-Zadeh et al., "Contemporary Reviews in Cardiovascular Medicine, Acute Coronary Events", Amercan Heart Assocation, Inc., Circulation. 2012;125:1147-1156, Mar. 6, 2012, pp. 1147-1156.
Arbab-Zadeh, et al. "The myth of the vulnerable plaque: transitioning from a focus on individual lesions to atherosclerotic disease burden for coronary artery disease risk assessment." J Am Coll Cardiol. 2015;65: 846-855.
Bakhasi, et al. "Comparative Effectiveness of CT-Derived Atherosclerotic Plaque Metrics for Predictiong Myocardial Ischemia." JACC Cardiovasc Imaging. Jul. 13, 2018. doi: 10.2013/j.jcmg.2018. 05.019. [Epub ahead of print].
Baskaran et al., "Dense calcium and lesion-specific ischemia: A comparison of CCTA with fractional flow reserve", Atherosclerosis 260, 2017 pp. 163-168.
Benjamin, et al. "Heart Disease and Stroke Statistics—2018 Update: A Report From the American Heart Association." Circulation. 2018;137: e67-e492.
Bergman "Using Multicoloured Halftsone Screens for Offset Print Quality Monitoring", Linköping Studies in Science and Technology; LiU-TEK-LIC-2005:02.
Blankstein R. et al. "Coronary CTA in the Evaluation of Stable Chest Pain: Clear Benefits, But Not for All." J Am Coll Cardiol 2017; 69 (14): 1771-73. doi: 10.1016/j.jacc.2017.02.011 [published Online First: Apr. 8, 2017].
Boogers, et al. "Automated Quantification of Coronary Plaque with Computed Tomography: Comparison with Intravascular Ultrasound using a Dedicated Registration Algorithm for Fusion-Based Quantification", Epub, (2012).
Budoff MJ, et al. "Diagnostic performance of 64-multidetector row coronary computed tomographic angiography for evaluation of coronary artery stenosis in individuals without know coronary artery disease: results from the prospective multicenter ACCURACY (Assessment by Coronary Computed Tomography of Individuals Undergoing Invasive Coronary Angiography) trial." J Am Coll Cardiol 2008; 52(21): 1724-32.
Bzdok "Classical Statistics and Statistical Learning in Imaging Neuroscience." Front Neurosci. 2017; 11:543.
Calvert, et al. "Association between IVUS Findings and Adverse Outcomes in Patients with Coronary Artery Disease: the VIVA (VH-IVUS in Vulnerable Atherosclerosis) Study." JACC Cardiovasc Imaging. 2011;4: 894-901.
Celeng, et al. "Non-invasive and Invasive Imaging of Vulnerable Coronary Plaque." trends Cardiovasc Med. 2016;26-538-47.
Cerqueira et al. "Standardized myocardial segmentation and nomenclature for tomographic imaging of the heart. A statement for healthcare professinals from the Cardiac Imaging Committee of the Council on Clinical Cardiology of the American Heart Association." Int J Cardiovasc Imaging 2002; 18(1): 539-42.
Chang et al., "Coronary Atherosclerotic Precursors of Acute Coronary Syndromes", Journal of the American College of Cardiology, vol. 71, No. 22, Jun. 5, 2018. pp. 2511 -2522.
Chang et al., "Selective Referral Using CCTA Versus Direct Referral for Individuals Referred to Invasive Coronary Angiography for Suspected CAD", JACC: Cardiovascular Imaging, vol. 12, No. 7, Jul. 2019. pp. 1303-1312.
Chung et al. "Image Segmentation Methods for Detecting Blood Vessels in Angiography", 2006 9th Int. Conf. Control, Automation, Robotics and Vision, Singapore, Dec. 5-8, 2006, ICARCV 2006, pp. 1424-1429.
Costopoulos, et al. "Intravascular Ultrasound and Optical Coherence Tomography Imaging of Coronary Atherosclerosis." Int J Cardiovasc Imaging. 2016;32: 189-200.
Cury, et al. "CAD-RADS™ Coronary Artery Disease—Reporting and Data System. An Expert consensus documents of the Society of Cardiovascular Computed Tomography (SCCT), the American College of Radiology (ACR) and the North American Society for Cardiovascular Imaging (NASCI)." Endorsed by the American COllege of Cardiology. J Cardiovasc COmput Tomogr. 2016;10: 269-81.
Danad et al. "Comparison of Coronary CT Angiography, SPECT, PET, and Hybrid Imaging for Diagnosis of Ischemic Heart Disease Determined by Fractional Flow Reserve." JAMA Cardiol 2017; 2 (10): 1100-07. doi 10.1001/jamacardio.2017.2471 [published Online First: Aug. 17, 2017].
De Bruyne B. et al. "Fractional flow reserve-guided PCI for stable coronary artery disease." The New England journal of medicine 2014; 371 (13): 1208-17. doi: 10.1056/NEJMoa1408758 [published Online First: 2014/0902].
De Graaf, et al. "Automatic Quantification and Characterization of Coronary Atherosclerosis with Computed Tomography Coronary Angiography: Cross-Correlation with Intravascular Ultrasound Virtual Histology", Int J Cardiovasc, pp. 1177-1190, (2013).
De Graaf, et al. "Feasibility of an Automated Quantitative Computed Tomography Angiography-Derived Risk Stratification of Patients with Suspected CAD." Am J Cardiol (2014).
DeLong ER, et al. "Comparing the areas under two or more correlated receiver operating characteristic curves: a nonparametric approach." Biometrics 1988; 44 (3): 837-45. [published Online First: Sep. 1, 1988].
Dey, et al. "Comparison of Quantitative Atherosclerotic Plaque Burden from Coronary CT Angiography in Patients with First Acute Coronary Syndrome and Stable CAD" J Cardivasc Comput tomogr (2014).
Dey et al., "Direct Quantatitive In Vivo Comparison of Calcified Atherosclerotic Plaque on Vascular MRI and CT by Multimodality Image Registration" Journal of Magnetic Resonance Imaging 23:345-354 (2006).

(56) References Cited

OTHER PUBLICATIONS

Dey et al., Integrated prediction of lesion-specific ischemia from quantitative coronary CT Angiography using machine learning: a multicenter study, European Radiology 2018.
Dey, et al. "Non-Invasive Measurement of Coronary Plaque from Coronary CT Angiography and its Clinical Implication", Expert Review of Cardiovascular Therapy (2013).
Diaz-Zamudio, et al. "Automated Quantitiative Plaque Burden from Coronary CT Angiography Non-Invasively Predicts Hemodynamic Significance by Using Fractional Flow Reserve in Intermediate Coronary Lesions." Radiology (2015).
Douglas et al., "Outcomes of Anatomical versus Functional Testing for Coronary Artery Disease", N Engl J Med. Apr. 2, 2015, p. 1291-1300.
Driessen et al., "Adverse Plaque Characteristic Relate More Strongly With Hyperemic Fractional Flow Reserve and Instanteous Wave-Free Ratio Than With Resting Instantaneous Wave-Free Ratio", JACC: Cardiovascular Imaging, 2019, in 11 pages.
Driessen et al., "Effect of Plaque Burden and Morphology on Myocardial Blood Flow and Franctional Flow Reserve", Journal of the American College of Cardiology, vol. 71, No. 5, 2018 p. 499-509.
Dwivedi et al., "Evaluation of Atherosclerotic Plaque in Non-invasice Coronary Imaging", Korean Circulation Journal, Feb. 2018. 48(2), pp. 124-133.
Ehara et al. "Spotty calcification typifies the culprit plaque in patients with acute myocardial infarction: an intravascular ultrasound study." Circulation 2004; 110(22): 3424-9.
Erickson BJ, et al. "Machine Learning for Medical Imaging." Radiographics 2017; 37(2) pp. 505-515.
Ferencik, et al. "Computed Tomography-Based High-Risk Coronary Plaque Score to Predict ACS Among Patients with Acute Chest Pain" Journal of Cardiovascular Computed Tomography, (2015).
Ferencik et al., "Use of High-Risk Coronary Atherosclerotic Plaque Detection for Risk Stratification of Patients With Stable Chest Pain", JAMA Cardiol, Feb. 2018 in 19 pages.
Fihn et al. "2012 ACCF/AHA/ACP/AATS/PCNA/SCAI/STS Guideline for the Diagnosis and the Management of Patients With Statble Ischemic Heart Disease: Executive Summary: A Report of the American College of Cardiology Foundation/American Heart Association Task Force on Practice Guidelines, and the American College of Physicians, American Association for Thoracic Surgery, Preventive Cardiovascular Nurses Association, Society for Cardiovascular Angiography and Interventions, and Society of Thoracic Surgeons." J Am Coll Cardio 2012;60(24):2564-603. doi: 10.1016/c.cacc.2012.07.012 [published Online First: Nov. 28, 2012].
Finh et al. "2014 ACC/AHA/AATS/PCNA/SCAI/STS focused update of the guideline for the diagnosis and management of patients with stable ischemic heart disease: a report of the American College of Cardiology/American Heart Association Task Force on Practice Guidelines, and the American Association for Thoracic Surgery, Preventive Cardiovascular Nurses Association, Society for Cardiovascular Angiography and Interventions, and Society of Thoracic Surgeons." Journal of the American College of Cardiology 2014;64 (18): 1929-49. doi:10.1016/j.jacc.2014.07.017 [published Online First: 2014/08/01].
Friedman et al., "Additive logistic regression: a statistical view of boosting (With discussion and a rejoinder by the authors)." Ann Statist. 2000; 28(2) pp. 337-407.
Funama, Yoshinori, et al. "Improved estimation of coronary plaque and luminal attenuation using a vendor-specific model-based iterative reconstruction algorithm in contrast-enhanced CT coronary angiography." Academic radiology 24.9.
Gaemperli et al. "Cardiac hybrid imaging." Eur Heart J 2011; 32(17): 2100-8.
Gaur et al., "Coronary plaque quantification and fractional flow reserve by coronary computed tomography angiography identify ischaemia-causing lesions", European Heart Journal, 2016 pp. 1220-1227.
Goff, et al. "2013 ACC/AHA Guidelines on the Assessment of Cardiovascular Risk: a Report of the American College of Cardiology/American Heart Association Task Force on Practice Guidelines." J Am Coll Cardiol. 2014;63: 2935-59.
Gogas, et al. "Assessment of Coronary Atherosclerosis by IVUS and IVUS-based Imaging Modalities: Profession and Regression Studies, Tissue Composition and Beyond." Int J Cardiovasc Imaging. 2011;27: 225-37.
Goldstein et al., "Moving beyond regression techniques in cardiovascular risk prediction: applying machine learning to address analytic challenges." Eur Heart J. 2017; 38(23) pp. 1805-1814.
Greenwood et al. "Effect of Care Guided by Cardiovascular Magnetic Resonance, Myocardial Perfusion Scintigraphy, or NICE Guidelines on Subsequent Unnecessary Angiography Rates: The CE-MARC 2 Randomized Clinical Trial." JAMA 2016; 316(10): 1051-60. doi: 10.1001/jama.2016.12680 [published Online First: Aug. 30, 2016.
Guyon et al., "An introduction to variable and feature selection." J Mach Learn Res. 2003; 3:1157-1182.
Hadamitzky et al., "Optimized Progostic Score for Coronary Computed Tomographic Angiography", Journal of the American College of Cardiology, vol. 62, No. 5, 2013, pp. 468-476.
Hall et al., "The WEKA data mining software: an update." SIGKDD Explor Newsl. 2009; 11(1) pp. 10-18.
Hall et al., "Benchmarking attribute selection techniques for discrete clas data mining." IEEE Transaction on Knowledge and Data Engineering 2003; 15(6): pp. 1437-1447.
Han et al. "Incremental role of resting myocardial computed tomography perfusion for predicting physiologically significant coronary artery disease: A machine learning approach." J Nucl Cardiol. 2018; 25(1) pp. 223-233.
Han et al., "Quantitative measurement of lipid rich plaque by coronary computed tomography angiography: A correlation of histology in sudden cardiac death", Atherosclerosis, 2018 pp. 426-433.
Hausleiter et al. "Estimated radiation dose associated with cardiac CT angiography." JAMA 2009; 301(5): 500-7.
Heo et al., "Optimal boundary detection method and window settings for coronary atherosclerotic plaque volume analysis in coronary computed tomography angiography: comparison with intravascular ultrasound", Eur Radiol, (2016) 26:31, pp. 3190-3198.
Hesse et al. "EANM/ESC procedural guidelines for myocardial perfusion imaging in nuclear cardiology." Eur J Nucl Med Mol Imaging 2005; 32 (7): 855-97. doi: 10.1007/s00259-005-1779-y.
Howard G. et al. "Cigarette smoking and progression of atherosclerosis: The Atherosclerosis Risk in Communities (AIRC) Study." JAMA 1998; 279(2) pp. 119-124.
Hundley WG et al. "Society for Cardiovascular Magnetic Resonance guidelines for reporting cardiovascular magnetic resonance examinations." J Cardiovasc Magn Reson 2009; 11:5.
International Search Report and Written Opinion for Application No. PCT/US20/15035 dated Apr. 14, 2020, in 20 pages.
International Search Report and Written Opinion for Application No. PCT/US2021/012218 dated Mar. 17, 2021, in 11 pages.
Kanamori et al. "Robust Loss Functions for Boosting" Neural Computation. 2007; 19(8) pp. 2183-2244.
Kang, et al. Automated Knowledge-Based Detection of Nonobstructive and Obstructive Arterial Lesions from Coronary CT Angiography. Med Phys.
Kang, et al. "Structured Learning Algorithm for Detection of Nonobstructive and Obstructive Coronary Plaque Lesions from Computed Tomography Angiography", Journal of Medical Imaging, (2015).
Klass O, et al. "Coronary plaque imaging with 256-slice multidetector computed tomography: interobserver ariability of volumetric lesion parameters with semiautomatic plaque analysis software", Int J Cardiovasc Imaging, (2010). 26; pp. 711-720.
Klein et al. :Diagnostic quality of time-averaged ECG-Gated CT data, SPIE medical imaging, 2019.
Knuiman et al. "An Empirical comparison of multivariable methods for estimating risk of death from coronary heart disease." J. Cardiovasc Risk. 1997; 4(2): pp. 127-134.

(56) References Cited

OTHER PUBLICATIONS

Kolossvary, et al. "Radiomic Features Are Superior to Conventional Quantitative Computed Tomographic Metrics to Identify Coronary Plaques with Napkin-Ring Sign." Circ Cardiovasc Imaging. 2017;10.
Koo BK, et al. "Diagnosis of ischemia-causing coronary stenoses by noninvasive fractional flow reserve computed from coronary computed tomographic angiograms. Results from the prospective multicenter DISCOVERY-FLOW (Diagnosis of Ischemia-Causes Stenoses Obtained Via Noninvasive Fractional Flow Reserve) study." J Am Coll Cardiol 2011; 58 (19): 1989-97. doi: 10.1016/j.jacc.2011.06.066 [published Online First: Oct. 29, 2011].
Kim et al., "Natural History of Diabetic Coronary Atherosclerosis by Quantitative Measurement of Serial Coronary Computed Tomographic Angiography", JACC: Cardiovascular Imaging, vol. 11, No. 10, 2018 pp. 1461-1471.
Kramer et al. "Standardized cardiovascular magnetic resonance imaging (CMR) protocols, society for cardiovascular magnetic resonance: board of trustees task force on standardized protocols." J Cardiovasc Magn Reson 2008; 10:35. doi: 10.1186/1532-429X-10-35.
Kwan et al., "Bridging the gap for lipid lowering therapy: plaque regression, coronary computed tomographic angiography, and imaging-guided personalized medicine." Expert Rev Cardiovasc Ther. 2017; 15(7): pp. 547-558.
Lee et al., "Differences in Progression to Obstructive Lesions per High-Risk Plaque Features and Plaque Volumes With CCTA", JACC: Cardiovascular Imaging, 2019 in 9 pages.
Lee et al., "Effects of Statins on Coronary Atherosclerotic Plaques—The PARADIGM (Progession of AtheRosclerotic PlAque Determined by Computed TomoGraphic Angiography Imaging) Study", JACC: Cardiovascular Imaging, 2018.
Lee et al., "Identification of High-Risk Plaques Destined to Cause Acute Coronary Syndrome Using Coronary Computed Tomographic Angiography and Computational Fluid Dynamics", JACC: Cardiovascular Imaging, vol. 12, No. 6, Jun. 2019. pp. 1032-1043.
Lee et al., "Rationale and design of the Progession of AtheRosclerotic PlAque Determined by Computed TomoGraphic Angiography Imaging (PARADIGM) registry: A comprehensive exploration of plaque progression and its impact on clinical outcomes from a multicenter serial coronary computed tomographic angiography study", American Heart Journal, vol. 182. 2016 pp. 72-79.
Lee et al., Rationale and design of the Coronary Computed Tomographic Angiography for Selective Cardiac Catheterization: Relation to Cardiovascular Outcomes, Cost Effectiveness and Quality of Life (CONSERVE) trial:, Am Heart J, 2017; vol. 186, pp. 48-55.
Lee et al., "Reproducibility in the assessment of noncalcified coronary plaque with 256-slice multi-detector CT and automated plaque analysis software", Int J Cardiovasc Imaging; 2010; 26:237-244.
Lee et al., "Quantification of Coronary Atherosclerosis in the Assessment of Coronary Artery Disease." Circ Cardiovasc Imaging. 2018; 11(7): e007562.
Leipsic et al. "SCCT guidelines for the interpretation and reporting of coronary CT angiography: a report of the Society of Cardiovascular Computed Tomography Guidelines Committee" J Cardiovasc Comput Tomogr 2014; 8(5): 342-58.
Libby P. "Mechanisms of acute coronary syndromes and their implications for therapy." N Engl J Med. 2013; 368: 2004-13.
Lu et al., "Central Core Laboratory versus Site Interpretation of Coronary CT Angiography: Agreement and Association with Cardiovascular Events in the PROMISE Trial", Radiology: vol. 287, No. 1, Apr. 2018, pp. 87-95.
Lundberg, et al. "A Unified Approach to Interpreting Model Predictions." 31st Conference on Neural Information Processing Systems (NIPS 2017).
Mancio, Jennifer, et al. "Perivascular adipose tissue and coronary atherosclerosis." Hear 104.20 (2018): 1654-1662. (Year: 2018).
Maurovich-Horvat, et al. "Comprehensive Plaque Assessment by Coronary CT Angiography", Nature Reviews, (2014).
Maurovich-Horvat, et al. "The napkin-ring sign indicates advanced atherosclerotic lesions in coronary CT angiography.", JACC Cardiovasc Imaging 2012; 5(12): 1243-52.
Meijboom et al. "Diagnostic accuracy of 64-slice computed tomography coronary angiography: a prospective, multicenter, multivendor study." J Am Coll Cardiol 2008; 52 (25): 2135-44. doi: 10.1016/j.jacc.2008.08.058.
Melikian et al. "Fractional flow reserve and myocardial perfusion imaging in patients with angiographic multivessel coronary artery disease." JACC Cardiovasc Interv 2010; 3 (3): 307-14. doi: 10.1016/j.jcin.2009.12.010 [published Online First: Mar. 20, 2010].
Mettler et al. "Effective doses in radiology and diagnostic nuclear medicine: a catalog." Radiology 2008; 248(1): 254-63.
Miller et al. "Diagnostic performance of coronary angiography by 61-row CT." N Engel J Med 2008; 359 (22): 2324-36. doi: 10.1056/NEJMoa0806576 [published Online First: Nov. 29, 2008].
Min, "Atherosclerotic plaque characterization:a need for a paradigm shift for prediction of risk", European Heart Journal—Cardiovascular Imaging, Oct. 2017. pp. 1340-1341.
Min et al., "Atherosclerosis, Stenosis, and Ischemia", JACC: Cardiovascular Imaging, vol. 11, No. 4, Apr. 2018. pp. 531-533.
Min, "Chess and Coronary Artery Ischemia: Clinical Implications of Machine-Learning Applications", Circulation:Cardiovascular Imaging, 2018 in 4 pages.
Min et al., "Diagnostic accuracy of fractional flow reserve from anatomic CT angiography." JAMA 2012; 038 (12): 1237-45. doi: 10.1001/2012.jama.11274 [published Online First: Aug. 28, 2012].
Min et al., "The Immediate Effects of Statins on Coronary Atherosclerosis", JACC:Cardiovascular Imaging, vol. 11, No. 6, Jun. 2018. pp. 839-841.
Min et al. "Prognostic value of multidetector coronary computed tomographic angiography for predication of all-cause mortality" J Am Coll Cardio 2007; 50(12): 1161-70.
Min, et al. "Rationale and Design of the CONFIRM (Coronary CT Angiography Evalution for Clinical Outcomes: An International Multicenter) Registry." J Cardiovasc Comput Tomogr. 2011;5:84-92.
Mintz GS. "Intravascular Imaging of Coronary Calcification and its Clinical Implications." JACC Cardiovasc Imaging. 2015;8: 461-471.
Montalescot et al. "2013 ESC guidelines on the management of stable coronary artery disease: the Task Force on the management of stable coronary artery disease of the European Society of Cardiology." Eur Heart J 2013;34(35: 2949-3003. doi: 10.1093/eurheartj/eht296 [published Online First: Sep. 3, 2013].
Motoyama et al. "Atherosclerotic plaque characterization by 0.5-mm-slice multislice computed tomographic imaging." Circ J 2009; 71(3): 363-6.
Motoyama et al. "Computed tomographic angiography characteristics of atherosclerotic plaques subsequently resulting in acute coronary syndrome." J Am Coll Cardiol 2009; 54(1): 49-57.
Motoyama et al. "Multislice computed tomographic characteristics of coronary lesions in acute coronary syndromes." J Am Coll Cardiol 2007; 50(4): 319-26.
Motwani et al., "Machine learning for prediction of all-cause mortality in patients with suspected coronary artery disease: a 5-year multicentre prospective registry analysis", European Heart Journal, 2017, pp. 500-507.
Naghavi, et al. From Vulnerable Plaque to Vulnerable Patient: a call for new definitions and risk assessment strategies: Part I. Circulation. 2003; 108: 1664-72.
Nair, et al. "Automated Coronary Plaque Characterisation with intravascular ultrasound backscatter: ex vivo validation." EuroIntervention. 2007; 3: 113-20.
Nakanishi R. et al. "Plaque progression assessed by a novel semi-automated quantitative plaque software on coronary computed tomography angiography between diabetes and non-diabetes patients: A propensity-score matching study." Atherosclerosis 2016; 255 pp. 73-79.
Nakazato et al., "Additive diagnostic value of atherosclerotic plaque characteristics to non-invasive FFR for indentification of lesions

(56) References Cited

OTHER PUBLICATIONS causing ischaemia: results from a prospective international multicentre trial", http://www.pcronline.com/eurointervention/ahead_of_print/201509-02/ in 9 pages.

Nakazato et al., "Aggregate Plaque Volume by Coronary Computed Tomography Angiography is Superior and Incremental to Luminal Narrowing for Diagnosis of Ischemic Lesions of Intermediate Stenosis Severity", Journal of the American College of Cardiology, vol. 62, No. 5, 2013 pp. 460-467.

Nakazato et al., "Atherosclerotic plaque characterization by CT angiography for identification of high-risk coronary artery lesions: a comparison to optical coherence tomography", European Heart Journal—Cardiovascular Imaging, vol. 16, 2015. pp. 373-379.

Nakazato et al., "Quantification and characterisation of coronary artery plaque volume and adverse plaque features by coronary computed tomographic angiography: a direct comparison to intravascular ultrasound", Eur Radiol (2013) 23, pp. 2109-2117.

Nakazato et al., "Relationship of low- and high-density lipoproteins to coronary artery plaque composition by CT angiography", Journal of Cardiovascular Computed Tomography 7, 2013, pp. 83-90.

Neglia et al. "Detection of significant coronary artery disease by noninvasive anatomical and functional imaging." Circ Cardiovasc Imaging 2015; 8 (3) doi: 10.1161/CIRCIMAGING.114.002179 [published Online First: Feb. 26, 2015].

Newby et al., "Coronary CT Angiography and 5-Year Risk of Myocardial Infarction", The New England Journal of Medicine, Aug. 25, 2018, pp. 924-933.

Newby et al., "CT coronary angiography in patients with suspected angina due to coronary heart disease (SCOT-HEART): an open-label, parallel-group, multicentre trial", www.thelancet.com, vol. 385. Jun. 13, 2015, pp. 2383-2391.

Nicholls, et al. "Effect of Evolocumab on Coronary Plaque Composition." J Am Coll Cardiol. 2018;72: 2012-2021.

Nicholls et al. "Intravascular ultrasound-derived measures of coronary atherosclerotic plaque burden and clinical outcome." J Am Coll Cardiol. 2010; 55(21): pp. 2399-2407.

Obaid, D.R., et al. "Atherosclerotic Plaque Composition and Classification Identified by Coronary Computed Tomography: Assessment of CT-Generated Plaque Maps Compared with Virtual Histology Intravascular Ultrasound and Histology." Circulation: Cardiovascular Imaging 6.5 (2013): 655-664. (Year: 2013).

Obaid, Daniel R., et al. "Coronary CT angiography features of ruptured and high-risk atherosclerotic plaques: correlation with intra-vascular ultrasound." Journal of Cardiovascular Computed Tomography 11.6 (2017): 455-461. (Year: 2017).

Otsuka et al. "Napkin-ring sign on coronary CT angiography for the prediction of acute coronary syndrome." JACC Cardiovasc Imaging 2013; 6(4): 448-57.

Ovrehus et al., "CT-based total vessel plaque analyses improves prediction of hemodynamic significance lesions as assessed by fractional flow reserve in patients with stable angina pectoris", Journal of Cardiovascular Computed Tomorgraphy 12, 2018 pp. 344-349.

Ovrehus, et al. "Reproducibility of Semi-Automatic Coronary Plaque Quantification in Coronary CT Angiography with Sub-mSv Radiation Dose." J Cardiovasc Comput Toogr, (2016).

Papadopoulou, et al. "Detection and Quantification of Coronary Atherosclerotic plaqie by 64-slice multidetector CT: A systematic head-to-head comparison with intravascular ultrasound." Atherosclerosis. 2011;219: 163-70.

Papadopoulou, et al. Reproductibility of CT Angiography Data Analysis Using Semiautomated Plaque Quantification Software: Implications for the Design of Longitudinal Studies. Int J Cardiovasc Imaging.

Park et al., "Atherosclerotic Plaque Characteristics by CT Angiography Identify Coronary Lesions That Cause Ischemia", JACC: Cardiovascular Imaging, vol. 8, No. 1, 2015 in 10 pages.

Park, et al. "Clinical Feasibility of 3D Automated Coronary Atherosclerotic Plaque Quantification Algorithm on Coronary Computed Tomography Angiography: Comparison with Intravascular Ultrasound" European Radiology (2015), 25: 3073-3083.

Park, et al. "Visual-functional Mismatch between Coronary Angiography and Fractional Flow Reserve." JACC Cardiovasc Interv. 2012; 5: 1029-36.

Pavlou et al., "A note on obtaining correct marginal predictions from a random intercepts model for binary outcomes." BMC Med Res Methodol 2015; 15:59. doi: 10.1186/s12874-015-004606 [published Online First: Aug. 6, 2015].

Pedregosa, et al. "Scikit-learn: Machine Learning in Python." Journal of Machine Learning Research, 2011;12: 2825-2830.

Picano et al. "The appropriate and justified use of medical radiation in cardiovascular imaging: a position document of the ESC Associations of Cardiovascular Imaging, Percutaneous Cardiovascular Interventions and Electrophysiology." Eur Heart J 2014; 35(10): 665-72.

Puchner, et al. "High-Risk Plaque Detected on Coronary CT Angiography Predicts Acute Coronary Syndrome Independent of Significant Stenosis in Patients with Acute Chest Pain" J Am Coll Cardiol 2014.

Puchner, et al. "High-Risk Coronary Plaque at Coronary CT Angiography is Associated with NAFLD, Independent of Coronary Plaque and Stenosis Burden", J Cardiovasc Comput Tomogr.

Raff, et al. "SCCT guidelines for the interpretation and reporting of coronary computed tomographic angiography" J Cardiovasc Comput Tomogr 2009: 3(2): 122-36.

Rehani et al. "ICRP Publication 117. Radiological protection in fluoroscopically guided procedures performed outside the imaging departement." Ann ICRP 2010; 40(6): 1-102.

Rizvi et al., "Diffuse coronary artery disease among other atherosclerotic plaque characteristics by coronary computed tomography angiography for predicting coronary vessel-specific ischemia by fractional flow reserve", Atherosclerosis 258, 2017 pp. 145-151.

Rizvi et al., "Rationale and Design of the CREDENCE Trial: computed TomogRaphic evaluation of atherosclerotic DEtermiNants of myocardial IsChEmia", BMC Cardiovascular Disorders, 2016, in 10 pages.

Roy-Cardinal et al. "Intravascular Ultrasound Image Segmentation: A Three-Dimentional Fast-Marching Method Based on Grey Level Distributions", IEEE Transactons on Medical Imaging, vol. 25, No. 5, May 2006.

Sabir, A et al. Measuring Noncalcified Coronary Atherosclerotic Plaque Using Voxel Analysis with MDCT Angiography: Phantom Validation: American Journal of Roentgenology, Apr. 2008; vol. 190, No. 4, pp. 242-246.

Samady H. et al. "Coronary artery wall shear is associated with progression and transformation of atherosclerotic plaque and arterial remodeling in patients with coronary artery disease." American Heart Association Circuliation, vol. 124, Issue 7, Aug. 16, 2011, pp. 779-788.

Schinkel et al. "Nonivasive elalusation of ischaemic heart desease: myocardial perfusion imaging or stress echocardiography?" European Heart Journal (2003) 24, 789-800.

Schlett et al. "How to assess non-calcified plaque in CT angiography: delineation methods affect diagnostic accuracy of low-attenuation plaque by CT for lipid-core plaque in history." Euro Heart J Cardiovasc Imaging 2013; 14(11): 1099-105.

Schuurman, et al. "Prognostic Value of Intravascular Ultrasound in Patients with Coronary Artery Disease." J Am Coll Cardiol. 2018;72: 2003-2011.

Seghier et al., "Lesion identification using unified segmentation-normalisation models and fuzzy clustering" NeuroImage 40(2008) 1253-1266.

Seifarth, et al. "Histopathological Correlates of the Napkin-Ring Sign Plaque in Coronary CT Angiography." Send to Atherosclerosis. 2012;224: 90-6.

Sharma et al., "Stress Testing Versus CT Angiography in Patients With Diabetes and Suspected Coronary Artery Disease", Journal of the American College of Cardiology, vol. 73, No. 8, 2019 pp. 893-902.

Shaw et al. "Optimal medical therapy with or without percutaneous coronary intervention to reduce ischemic burden: results from the Clinical Outcomes Utilizing Revascularization and Aggressive Drug

(56) References Cited

OTHER PUBLICATIONS

Evaluation (COURAGE) trail nuclear substudy." Circulation 2008; 117 (10): 1283-91. doi: 10.116/CIRCULATIONAHA.107.743963.
Shaw et al. "Why all the focus on cardiac imaging?" JAAC Cardiovasc Imaging 2010; 3(7): 789-94 doi: 10.16/j.jcmg.2010.05.004.
Shin S. et al., "Impact of Intensive LDL Cholesterol Lowering on Coronary Artery Atherosclerosis Progression: A Serial CT Angiography Study." JACC Cardiovasc Imaging. 2017; 10(4) pp. 437-446.
Siasos, et al. "Local Low Shear Stress and Endothelial Dysfunction in Patients with Nonobstructive Coronary Atherosclerosis." J Am Coll Cardiol. 2018;71: 2092-2102.
Song et al. "Comparison of machine learning techniques with classical statistical models in predicting health outcomes." Stud Heatlh Technol Inform. 2004; 107(Pt 1) pp. 736-740.
Staruch, et al. "Automated Quantitative Plaque Analysis for Discrimination of Coronary Chronic Total Occlusion and Subtotal Occlusion in Computed Tomography Angiography", J Thoracic Imaging, (2016).
Stone, et al. "A prospective natural-history stucy of coronary atherosclerosis." N Engl J Med 2011; 364(3): 226-35.
Stuijfzand, et al. "Stress Myocardial Perfusion Imaging vs Coronary Computed Tomographic Angiography for Diagnosis of Invasive Vessel-Specific Coronary Physiology Predictive Modeling Results From the Computed Tomographic Evaluation of Atherosclerotic Determinants of Myocardial Ischemia (CREDENCE) Trial", JAMA Cardiology, doi:10.1001/jamacardio.2020.3409, Aug. 19, 2020.
Sun, et al. "Diagnostic Value of Multislice Computed Tomography Angiography in Coronary Artery Disease: a Meta-Analysis." Eur J Radiol. 2006;60: 279-86.
Taylor et al., "Patient-Specific Modeling of Cardiovascular Mechanics", Annu. Rev. Biomed. Eng. 2009.11:109-139.
Thim, et al. "Unreliable Assessment of Necrotic Core by Virtual Histology Intravascular Ultrasound in Porcine Coronary Artery Disease." Circ Cardiovasc Imaging. 2010;3: 384-91.
Thygesen, et al. "Third Universal Definition of Myocardial Infarction." Glob Heart. 2013;7: 275-95.
Tian, et al. "Distinct Morphological Features of Ruptured Culprit Plaque for Acute Coronary Events Compared to those with Silent Rupture and Thin-Cap Fibroatheroma: a Combined Optical Coherence Tomography and Intravascular Ultrasound Study." J Am Coll Cardiol. 2014;63: 2209-16.
Tilkemeier et al., "American Society of Nuclear Cardiology information statement: Standardized reporting matrix for radionuclide myocardial perfusion imaging." J Nucl Cardiol 2006; 13 (6): e157-71. doi: 10.1016/j.nuclcard.2006.08.014.
Tomey MI, et al. "Advances in the understanding of plaque composition and treatment options: year in review." J AM Coll Cardio. 2014; 63(16) pp. 1604-1616.
Tonino et al., "Angiographic versus functional severity of coronary artery stenoses in the FAME study fractional flow reserve versus angiography in multivessel evaluation." Journal of the American College of Cardiology 2010; 55 (25): 2816-21. doi: 10.1016/j.jacc.2009.11-096 [published Online First: Jun. 29, 2010].
Van Ooijen, et al. "Coronary Artery Imaging with Multidetector CT: Visualization Issues" RadioGraphics, vol. 23. (2003).
Van Rosendael et al., "Maximization of the usage of coronary CTA derived plaque information using a machine learning based algorithm to improve risk stratification; insights from the CONFIRM registry", Journal of Cardiovascular Computed Tomography 12, 2018, pp. 204-209.
Van Rosendael et al., "Quantitative Evaluation of High-Risk Coronary Plaque by Coronary CTA and Subsequent Acute Coronary Events", JACC: Cardiovascular Imaging, vol. 12, No. 8, Aug. 2019. pp. 1568-1571.
Versteylen MO, et al. "Additive value of semiautomated quantification of coronary artery diseae using cardiac computed tomographic angiography to predict future acute coronary syndrome." J Am Coll Cardiol. 2013; 61(22): pp. 2296-2305.
Virmani, et al. "Atherosclerotic plaque progression and vulnerability to rupture: angiogenesis as a source of intraplaque hemorrage." Arterioscler Thromb Vasc Biol. 2005; 25: 2054-61.
Virmani, et al. "Lessons from sudden coronary death: a comprehensive morphological classification scheme for atherosclerotic lesions." Arterioscler Thromb Vasc Biol. 2000;20: 1262-75.
Virmani, et al. "Pathology of the Vulnerable Plaque." J Am Coll Cardiol. 2006; 47: C13-8.
Wei, et al. "Computerized Detection of Noncalcified Plaques in Coronary CT Angiography: Evaluation of Topological Soft Gradient Prescreening Method and Luminal Analysis" Med Phys, (2014).
Weir-MacCall et al., "Impact of Non-obstructive left main disease on the progession of coronary artery disease: A PARADIGM substudy", Journal of Cardiovascular Computed Tomography 12, 2018, pp. 231-237.
Weisenfeld et al. "Automatic Segmentation of Newborn Brain MRI", NIH PA Author Manuscript 2010.
Williams et al., "Coronary Artery Plaque Chracteristics Associated With Adverse Outcomes in the SCOT-HEART Study", Journal of the American College of Cardiology, vol. 73, No. 3, Jan. 29, 2019. pp. 291-301.
Williams et al. "Use of Coronary Computed Tomographic Angiography to Guide Management of Patients with Coronary Disease." Journal of American College of Cardiology 2016; 67 (15): 1759-68. doi: 10.1016/J.Jacc.2016.02.026 [published Online First: Apr. 16, 2016].
Wilson et al. "Prediction of coronary heart disease using risk factor categories" Circulation 1998; 97(18) pp. 1837-1847.
Won et al., "Longitudinal assessment of coronary plaque volume change related to glycemic status using serial coronary computed tomography angiography: A Computed TomoGraphic Angiography Imaging) substudy", Journal of Cardiovascular Computed Tomography 13, 2019 pp. 142-147.
Won et al., "Longitudinal quanititive assessment of coronary plaque progression related to body mass index using serial coronary computed tomography angiography", European Heart Journal—Cardiovascular Imaging, 2019 pp. 591-599.
Yang, et al. "Automatic centerline extraction of coronary arteries in coronary computed tomographic angiography" The International Journal of Cardiocascular Imaging, 28, pp. 921-933. (2012).
Yokoya K, et al. "Process of progression of coronary artery lesions from mild or moderate stenosis to moderate or severe stenosis: A study based on four serial coronary arteriograms per year." Circulation 1999; 100(9); pp. 903-909.
Zeb I et al. "Effect of statin treatment on coronary plaque progression—a serial coronary CT angiography study." Atherosclerosis. 2013; 231(2) pp. 198-204.
Zhao Z., et al. "Dynamic nature of nonculprit coronary artery lesion morphology in STEMI: a serial IVUS analysis from HORIZONS-AMI trial." JACC Cardiovasc Imaging, 2013; 6(1) pp. 86-95.

\* cited by examiner

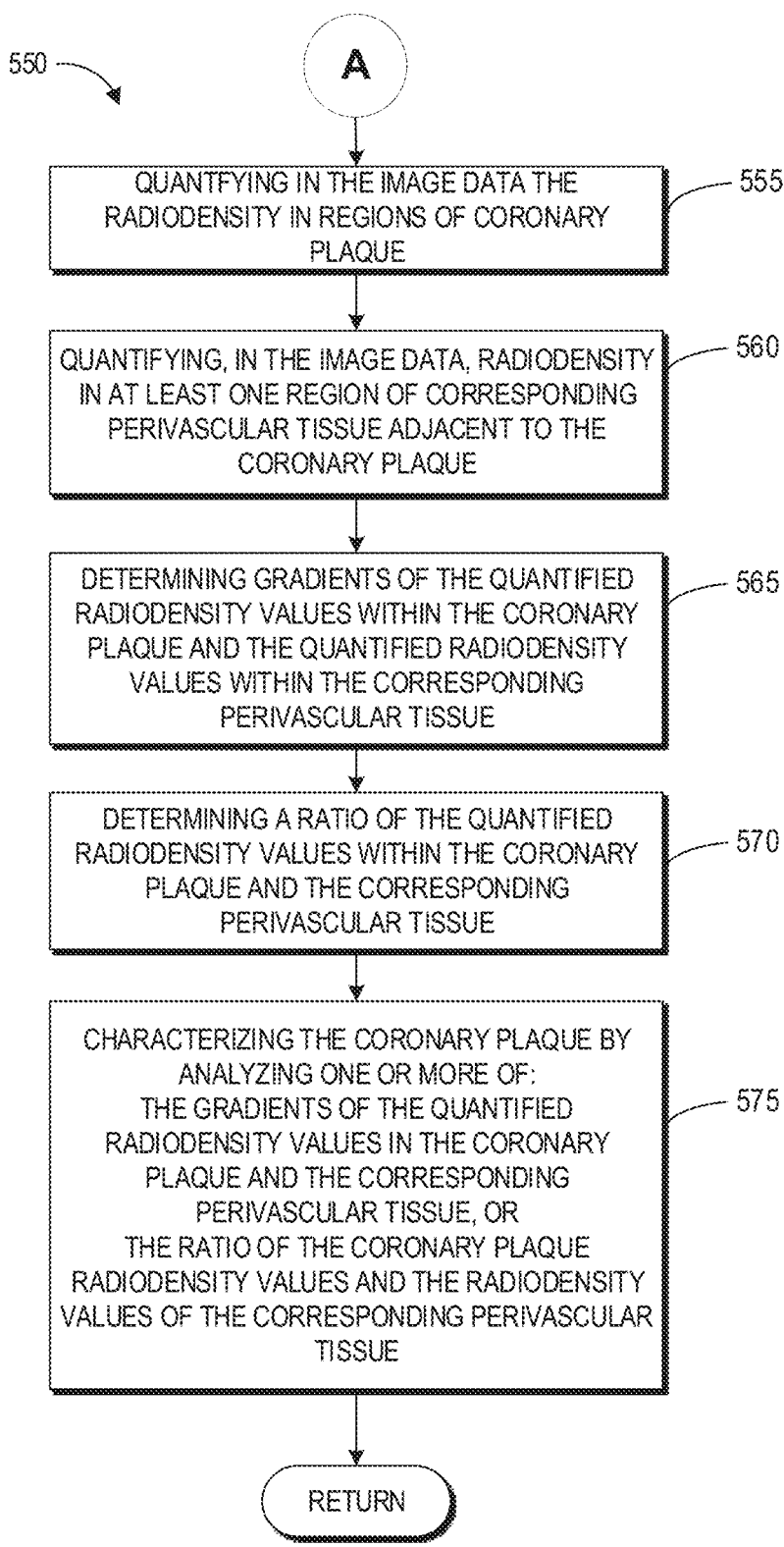

| Patient | |
|---|---|
| Item | Importance or Value |
| Sex | weight/value# |
| Age | weight/value# |
| BMI | weight/value# |
| Medication | weight/value# |
| Blood Pressure | weight/value# |
| Heart Rate | weight/value# |
| Weight | weight/value# |
| Height | weight/value# |
| Race | weight/value# |
| Body Habitus | weight/value# |
| Smoking | weight/value# |
| Diabetes | weight/value# |
| Hypertension | weight/value# |
| Prior CAD | weight/value# |
| Family History | weight/value# |
| Labs | weight/value# |
| ⋮ | ⋮ |
| Total | Total# |

FIG. 13

Scan

| Item | Importance or Value |
|---|---|
| Contrast to Noise Ratio | weight/value# |
| Signal to Noise Ratio | weight/value# |
| Tube Current | weight/value# |
| Tube Voltage | weight/value# |
| Contrast Type | weight/value# |
| Contrast Volume | weight/value# |
| Flow Rate | weight/value# |
| Flow Duration | weight/value# |
| Slice Thickness | weight/value# |
| Slice Spacing | weight/value# |
| Pitch | weight/value# |
| Vasodilator | weight/value# |
| Beta Blockers | weight/value# |
| Recon option | weight/value# |
|   Iterative | weight/value# |
|   Filtered Back Projection | weight/value# |
| Recon Type | |
|   Standard | weight/value# |
|   High Resolution | weight/value# |
| Display Field of View | weight/value# |
| Rotation Speed | weight/value# |
| Gating | |
|   Prospective Triggering | weight/value# |
|   Retrospective Gating | weight/value# |
| Stents | weight/value# |
| Heart Rate | weight/value# |
| Blood Pressure | weight/value# |
| ⋮ | ⋮ |
| Total | Total# |

FIG. 14

| Cardiac | |
|---|---|
| Item | Importance or Value |
| Density | weight/value# |
| Volume | weight/value# |
| Geometry- shape | weight/value# |
| Location | weight/value# |
| Remodeling | weight/value# |
| Baseline Anatomy | weight/value# |
|    Diameter | weight/value# |
|    Length | weight/value# |
| Compartments | weight/value# |
|    Inner | weight/value# |
|    Outer | weight/value# |
|    Within | weight/value# |
| Stenosis | weight/value# |
|    Diameter | weight/value# |
|    Area | weight/value# |
| Myocardial Mass | weight/value# |
| Plaque Volume | weight/value# |
| Plaque Composition | weight/value# |
| Texture | weight/value# |
| Uniformity | weight/value# |
| ⋮ | ⋮ |
| | |
| | |
| | |
| | |
| | |
| | |
| Total | Total# |

FIG. 15

SYSTEMS AND METHODS OF CHARACTERIZING HIGH RISK PLAQUES

INCORPORATION BY REFERENCE TO ANY PRIORITY APPLICATIONS

This application is a continuation of U.S. patent application Ser. No. 17/033,136, filed Sep. 25, 2020, which is a continuation of U.S. patent application Ser. No. 16/750,278, filed Jan. 23, 2020, now U.S. Pat. No. 10,813,612, which claims the benefit of U.S. Provisional Application No. 62/797,024, filed Jan. 25, 2019. Any and all applications for which a foreign or domestic priority claim is identified in the Application Data Sheet as filed with the present application are hereby incorporated by reference under 37 CFR 1.57.

TECHNICAL FIELD

The systems and methods disclosed herein are directed to identifying high risk plaques in coronary arteries, and more particularly, to characterizing coronary plaque by using three-dimensional (3D) models of medical images of coronary arteries to calculate density ratios of the coronary plaque and surrounding tissues.

BACKGROUND

The heart is a muscle that receives blood from several arteries, including the left circumflex artery (LCX) and the left anterior descending artery (LAD), both of which branch off from the left main artery, and the right coronary artery. Coronary artery disease generally relates to a constriction or blockage of one of these arteries and may produce coronary lesions in the blood vessels providing blood to the heart, such as a stenosis (abnormal narrowing of a blood vessel) or ischemia (a deficient supply of blood to the body part due to obstruction of the inflow of arterial blood). As a result, blood flow to the heart may be restricted. A patient suffering from coronary artery disease may experience chest pain. A more severe manifestation of coronary artery disease may the lead to myocardial infarction, or a heart attack.

Patients suffering from chest pain and/or exhibiting symptoms of coronary artery disease may be subjected to one or more tests that may provide some indirect evidence relating to coronary lesions. For example, noninvasive tests may include electrocardiograms, blood tests, treadmill exercise tests, echocardiograms, single positron emission computed tomography (SPECT) and positron emission tomography (PET). Anatomic data may be obtained noninvasively using coronary computed tomography angiography (CCTA), which uses computed tomography (CT) scanning after an intravenous infusion of an iodinated contrast agent to examine the arteries that supply blood to the heart and determine whether they have been narrowed or blocked by plaque buildup. CCTA and CT scanning, as sometimes used herein, may be hereinafter referred to as CT scanning for brevity. Images generated from a CT scan can be reconfigured to create three-dimensional (3D) images that may be viewed on a monitor, printed on film, or transferred to electronic media. Invasive tests can include measuring the fractional flow reserve (FFR) of any given lesion in order to evaluate the functional significance of that lesion. FFR is defined as the ratio of the blood pressure downstream of a lesion to the blood pressure upstream of the lesion at hyperemia and requires cardiac catheterization to be measured. Another common invasive test is the invasive coronary angiogram, with heart disease severity scored through the SYNTAX scoring system, which involves assessing the coronary anatomy using angiograms and answering a series of questions. A score is generated based on the lesion characteristics and responses to the questions to determine the most appropriate course of treatment. This process is time-consuming and depends on an individual cardiologist's subjective characterizations of the coronary angiograms. Because of this limitation, the SYNAX score is sometimes performed by multiple cardiologists to obtain an average score, which increases the time and resources required to perform the assessment. Further, as with any invasive medical procedures, FFR and SYNTAX scoring risk adverse effects and unnecessary medical costs.

Although plaque features, such as adverse plaque characteristics (APCs), have been investigated for prognostic value of major adverse cardiac events using both invasive and noninvasive techniques (such as intravascular ultrasound, optical coherence tomography, and coronary computed tomography data), a need exist for methods and systems for predicting adverse cardiac events by characterizing individual coronary plaque using noninvasive imaging techniques (atomic image data specific to a patient).

SUMMARY

Coronary artery disease (CAD) is a major cause of morbidity and mortality. Coronary computed tomographic angiography (CCTA, sometimes referred to simply as CT) has emerged as a non-invasive method for evaluation of CAD. Coronary atherosclerosis is the primary disease entity of CAD, with coronary stenosis and ischemia serving as secondary and tertiary consequences of the atherosclerotic process. The primary mechanisms for heart attack resulting from coronary atherosclerosis are rupture of the plaque, erosion of the plaque, or a calcified nodular protrusion that punctures the plaque. Coronary atherosclerosis may present in many different forms: focal or diffuse, at bifurcations or trifurcations/along straight segments of the artery; of different compositions, for example, plaque can be graded as necrotic core, fibrofatty, fibrous, calcified and densely calcified; and of different 3D shapes. Not all coronary plaque will be implicated in adverse cardiac events, and overtreatment of non-risky plaques can impose unnecessary health risks to patients and may result in unnecessary increased health care costs. Herein is described methods and systems of using images generated by scanning a patient's arteries (e.g., CCTA) to identify coronary artery plaques that are at higher risk of causing future heart attack or acute coronary syndrome. While it cannot necessarily be determined whether these plaques will rupture, erode or protrude, it can be noted that these plaques will likely be the future culprits of heart attack or acute coronary syndrome (ACS).

Scientific evidence reported to date that examine "high risk plaque" features have focused on plaques alone and have identified certain atherosclerotic plaque features as associated with future risk of heart attack or ACS, such as aggregate plaque volume (APV), low attenuation plaque (LAP), positive arterial remodeling (PR) and napkin ring signs (NRS). Such studies, however, have failed to consider the relationship between the plaque and adjoining vascular structures, most notably the coronary lumen and the perivascular coronary fat/tissue.

"Radiodensity" as used herein is a broad term that refers to the relative inability of electromagnetic relation (e.g., X-rays) to pass through a material. In reference to an image, radiodensity values refer to values indicting a density in image data (e.g., film, print, or in an electronic format)

where the radiodensity values in the image corresponds to the density of material depicted in the image. "Attenuation" as used herein is a broad term that refers to the gradual loss of intensity (or flux) through a medium. "Hypo-attenuation" is a term that may be used to indicate, in an image, portions of materials having low density that appear darker. "Hyper-attenuation" is a term that may be used to indicate, in an image, portions of materials having high density that appear lighter in the image. Antoniades reported a fat attenuation index, FAI, which could identify high risk plaques by characterizing the radiodensity gradient of fat tissue (e.g., perivascular adipose tissue) near or surrounding such plaque. (See, Antonopoulos et al., "Detecting human coronary inflammation by imaging perivascular fat," *Sci. Transl. Med.*, Vol. 9, Issue 398, Jul. 12, 2017.) The attenuation density of fat cells closer to the density of water (e.g., Hounsfield unit (HU) density=0) contrast with fat cells of a lower HU density (closer to −100), with the former associated with more inflamed fat cells and achieving higher attenuation due to cholesterol efflux from those cells. This was assumed to identify areas where there are coronary artery atherosclerotic lesions that are more inflamed.

No study to date, however, has considered the relationship of the densities of the coronary lumen, the plaque itself and the perivascular coronary fat. As summarized below and described herein, methods and systems are described for identifying a coronary plaque that is at increased susceptibility to be implicated in future ACS, heart attack or death. In some embodiments, a ratio method is described where the plaque serves as the central fulcrum point between the lumen or perivascular coronary fat.

One innovation includes a method for characterization (e.g., volumetric characterization) of coronary plaque using data from images of the coronary plaque and perivascular tissue gathered from a computed tomography (CT) scan along a blood vessel, the image information including radiodensity values of coronary plaque and perivascular tissue located adjacent to the coronary plaque. In some embodiments, the perivascular tissue may include the vessel lumen and/or the perivascular fat. In some embodiments, the method can include creating three dimensional (3D) models from CT images prior to determining radiodensity values. In some embodiments, the method can include quantifying, in the image data, the radiodensity in regions of coronary plaque, quantifying, in the image data, radiodensity in at least one region of corresponding perivascular tissue adjacent to the coronary plaque, determining gradients of the quantified radiodensity values within the coronary plaque and the quantified radiodensity values within the corresponding perivascular tissue, determining a ratio of the quantified radiodensity values within the coronary plaque and the corresponding perivascular tissue, and characterizing the coronary plaque based on at least the radiodensity values and/or ratios. In some examples, the plaque may be characterized by analyzing one or more of a minimum radiodensity value of the plaque and/or the perivascular tissue and a maximum radiodensity value of the plaque and/or the perivascular tissue. In some embodiments, the perivascular tissue may include at least one of coronary artery lumen, fat or coronary plaque. Such methods are performed by one or more computer hardware processors configured to execute computer-executable instructions on a non-transitory computer storage medium. Such methods may include one or more other aspects, or the aspects of the methods may be characterized in various ways, in different embodiments, some of which are described below.

In some embodiments, the method further comprises receiving, via a network, the image data at a data storage component. In some embodiments, the network is one of the Internet or a wide area network (WAN). In some embodiments, the image data from a CT scan includes at least ten images, or at least 30 images, or more. In some embodiments, the method further includes generating a patient report comprising at least one of a diagnosis, a prognosis, or a recommended treatment for a patient based on the characterization of the coronary plaque Adipose tissue (or simply "fat") is a type of connective tissue that plays an important role in the functioning of the body by storing energy in the form of lipids and cushioning and insulating the body. It is a loose connective tissue composed mostly of adipocytes, but also may contain a stromal vascular fraction (SVF) of cells including preadipocytes (the predecessor cells to adipocytes), fibroblasts, and vascular endothelial cells, and a variety of immune cells. Quantifying radiodensity in at least one region of perivascular tissue can include quantifying radiodensity of coronary plaque and adipose tissue in one or more regions or layers of vascular and/or perivascular tissue. In some embodiments, the radiodensity of the scan information is quantified for water (e.g., as a control or reference point) in each of one or more of the regions of coronary plaque and perivascular tissue. In some embodiments, radiodensity of the scan information is quantified for necrotic core plaque in the each of one or more regions or layers of coronary plaque. In some embodiments, the coronary plaque radiodensity values and the perivascular tissue radiodensity values are an average radiodensity. In some embodiments, the coronary plaque radiodensity values and the perivascular tissue radiodensity values are a maximum radiodensity. In some embodiments, the coronary plaque radiodensity values and the perivascular tissue radiodensity values are a minimum radiodensity. The quantified radiodensities may be characterized as numerical values. In some embodiments, the quantified radiodensities account for CT scan- and patient-specific parameters, including but not limited to one or more of iodinated contrast agent, contrast type, injection rate, aortic contrast opacification, left ventricular blood pool opacification, signal-to-noise, contrast-to-noise, tube voltage, milliamps, method of cardiac gating, CT scanner type, heart rate, heart rhythm, or blood pressure.

Such methods may also include reporting the quantified radiodensities of the coronary plaque and the perivascular tissue as a gradient of such radiodensities. In some embodiments, the quantified radiodensities of the coronary plaque and the perivascular tissue are determined and reported as a ratio of the slopes of the radiodensity gradients of the coronary plaque and perivascular tissue adjacent to the coronary plaque. In some embodiments, the quantified (maximum or minimum) radiodensities of the coronary plaque and the perivascular tissue determined and each are reported as the differences in radiodensity values of the coronary plaque and the perivascular tissue. In some embodiments, the image data is gathered from a CT scan along a length of at least one of a right coronary artery, left anterior descending artery, left circumflex artery, aorta, carotid arteries, or, femoral arteries, or their branches. In some embodiments, the data is gathered from a CT scan along a length of a non-coronary reference vessel, which can be, for example, the aorta. The radiodensity of the image data can be expressed in a variety of measurement units. In one example, the radiodensity is quantified in Hounsfield units. In another example, the radiodensity is quantified in absolute material densities, for example, when multi-energy CT is performed, which uses spectral data allowing differentiation and classification of tissues to obtain material-specific images.

In some embodiments of the method for characterization (e.g., volumetric characterization) of coronary plaque, one or more regions (or layers) of perivascular tissue extend to an end distance from the outer wall of the blood vessel. In some embodiments of the method, one or more regions (or layers) of the coronary plaque tissue extend to an end distance from the outer wall of the blood vessel, the end distance being the fixed distance where the radiodensity of adipose tissue (i) reaches a maximum value within the plaque, or (ii) increases by a relative percent (e.g., ≥10%); (iii) or changes by a relative percent versus the lowest radiodensity value in the plaque. In some embodiments, the end distance may be defined as being the fixed distance where the radiodensity of adipose tissue (i) reaches a minimum value within the scanned anatomical area in a healthy vessel, or (ii) drops by a relative percent (e.g., ≥10%); or (iii) drops by a relative percent versus a baseline radiodensity value in a vessel of the same type free of disease. In some embodiments, the baseline radiodensity value is the radiodensity quantified in a layer of adipose tissue lying within a fixed layer or region surrounding the outer vessel wall, measured by a thickness, area or volume. In some embodiments, the baseline perivascular tissue radiodensity is the radiodensity quantified for a layer of adipose tissue lying proximal to the outer wall of the blood vessel. In some embodiments, the baseline adipose tissue radiodensity is the radiodensity quantified for water (as a reference or control point) in a layer of adipose tissue lying proximal to the outer wall of the blood vessel. The baseline radiodensity may be generated in various ways. In some embodiments, the baseline radiodensity is an average radiodensity. In some embodiments, the baseline radiodensity is a maximum radiodensity. In some embodiments, the baseline radiodensity is a minimum radiodensity. In some embodiments, a baseline coronary plaque radiodensity value is the average radiodensity quantified in a layer of coronary plaque tissue within a fixed layer or region within the plaque and is measured by a thickness, area or volume. In some embodiments, the baseline coronary plaque radiodensity is the radiodensity quantified for all coronary plaques in the measured vessels.

In some embodiments, the method may further include determining a plot of the change in quantified radiodensity relative to baseline radiodensity in each of one or more concentric layers of perivascular tissue with respect to distance from the outer wall of the blood vessel up to an end distance, determining the area of the region bound by the plot of the change in quantified radiodensity and a plot of baseline radiodensity with respect to distance from the outer wall of the blood vessel up to the end distance, and dividing said area by the quantified radiodensity measured at a distance from the outer wall of the blood vessel, wherein the distance is less than the radius of the vessel or is a distance from the outer surface of the vessel above which the quantified radiodensity of adipose tissue drops by more than 5% compared to the baseline radiodensity of adipose tissue in a vessel of the same type free of disease. Some embodiments of the method may further comprise determining a plot of the change in quantified radiodensity relative to baseline radiodensity in each of one or more concentric layers of coronary plaque tissue with respect to distance from the outer wall of the blood vessel up to the inner surface of the plaque, determining the area of the region bound by the plot of the change in quantified radiodensity and a plot of baseline radiodensity with respect to distance from the outer wall of the blood vessel up to the inner surface of the plaque, and dividing said area by the quantified radiodensity measured at a distance from the outer wall of the blood vessel, wherein the distance is less than the radius of the vessel or is a distance from the outer surface of the vessel above which the quantified radiodensity of adipose tissue drops by more than 5% compared to the baseline radiodensity of adipose tissue in a vessel of the same type free of disease. In some embodiments, the quantified radiodensity is the quantified radiodensity of adipose tissue in the each of one or more regions or layers of perivascular tissue or coronary plaque. In some embodiments, the quantified radiodensity is the quantified radiodensity of water in the each of one or more regions or layers of perivascular tissue. In some embodiments, the quantified radiodensity is an average radiodensity. In some embodiments, the quantified radiodensities are a maximum radiodensity. In some embodiments, the quantified radiodensities are a minimum radiodensity.

In some embodiments of the methods described herein, the methods may further comprise normalizing the quantified radiodensity of the coronary plaque and the perivascular tissue to CT scan parameters (patient- and CT-specific parameters), which include but are not limited to one or more of iodinated contrast agent, contrast type, injection rate, aortic contrast opacification, left ventricular blood pool opacification, signal-to-noise, contrast-to-noise, tube voltage, milliamps, method of cardiac gating, CT scanner type, heart rate, heart rhythm, or blood pressure. In some embodiments, the methods may also include normalizing the quantified radiodensity of the coronary plaque-associated perivascular fat to remote perivascular fat and/or normalizing the quantified radiodensity of the coronary plaque to remote coronary plaques.

Embodiments of the method may further comprise quantifying other high risk plaque features, such as remodeling, volume, spotty calcifications, and further characterizing the high risk plaque based on one or more of high risk plaque features. In some embodiments, characterization of the coronary plaque includes analyzing plaque heterogeneity, specifically the presence of calcium and non-calcified plaque admixtures. In some embodiments, characterizing the coronary plaque comprises identifying the coronary plaque as a high risk plaque if it is prone to be implicated as culprit lesions in future acute coronary events, based on comparison with previously classified patient image data which may include image data from scans taken for the same patient and/or image data from scans taken from other patients. In some embodiments, characterizing the coronary plaque comprises identifying the coronary plaque as a high-risk plaque if it is likely to cause ischemia (e.g., restriction in blood supply to tissue) based on a comparison with previously classified patient image data. In some embodiments, characterizing the coronary plaque comprises identifying the coronary plaque as a high-risk plaque if it is likely to show aberrations in shear stress (e.g., low shear stress) based on a comparison with previously classified patient image data.

A vasospasm is the narrowing of the arteries caused by a persistent contraction of the blood vessels, which is known as vasoconstriction. This narrowing can reduce blood flow. Vasospasms can affect any area of the body including the brain (cerebral vasospasm) and the coronary artery (coronary artery vasospasm). In some embodiments of the method, characterizing the coronary plaque comprises identifying the coronary plaque as a high risk plaque if it is likely to cause a vasospasm based on a comparison with previously classified patient image data. In some embodiments, characterizing the coronary plaque comprises identifying the coronary plaque as a high risk plaque if it is likely to rapidly progress based on a comparisons with previously classified patient image data. In some cases, coronary plaque may calcify, hardening by deposition of or conversion into calcium carbonate or other insoluble calcium compounds. In some embodiments, characterizing the coronary plaque comprises identifying the coronary plaque as a high risk plaque if it is likely not to calcify, based on a comparisons with previously classified patient image data. In some embodiments, characterizing the coronary plaque comprises identifying the coronary plaque as a high risk plaque if it is likely not to respond, regress or stabilize to medical therapy based on a comparisons with previously classified patient image data. In some embodiments, characterizing the coronary plaque comprises identifying the coronary plaque as a high risk plaque if it is progresses rapidly in volumetric size. In some embodiments, characterizing the coronary plaque comprises identifying the coronary plaque as a high risk plaque if it is associated with complications at the time of revascularization (such as by inducing no-reflow phenomenon) based on a comparisons with previously classified patient image data.

Another innovation includes a system for characterization of coronary plaque tissue (e.g., volumetric characterization) using image data gathered from one or more computed tomography (CT) scans along a blood vessel, the image information including radiodensity values of coronary plaque and perivascular tissue located adjacent to the coronary plaque. The system can include a first non-transitory computer storage medium configured to at least store the image data, a second non-transitory computer storage medium configured to at least store computer-executable instructions, and one or more computer hardware processors in communication with the second non-transitory computer storage medium. The one or more computer hardware processors are configured to execute the computer-executable instructions to at least quantify, in the image data, the radiodensities in regions of coronary plaque, and quantify, in the image data, radiodensities in at least one region of corresponding perivascular tissue adjacent to the coronary plaque, determine gradients of the quantified radiodensity values within the coronary plaque and the quantified radiodensity values within the corresponding perivascular tissue, determine a ratio of the quantified radiodensity values within the coronary plaque and the corresponding perivascular tissue, and characterize the coronary plaque by analyzing one or more of the gradients of the quantified radiodensity values in the coronary plaque and the corresponding perivascular tissue, or the ratio of the coronary plaque radiodensity values and the radiodensity values of the corresponding perivascular tissue.

Another innovation includes a non-transitory computer readable medium including instructions that, when executed, cause one or more hardware computer processors of an apparatus to perform a method, the method including quantifying, in the image data, the radiodensities in regions of coronary plaque. The method may further include quantifying, in the image data, radiodensities in at least one region of corresponding perivascular tissue adjacent to the coronary plaque, determining gradients of the quantified radiodensity values within the coronary plaque and the quantified radiodensity values within the corresponding perivascular tissue. The method may further include determining a ratio of the quantified radiodensity values within the coronary plaque and the corresponding perivascular tissue. The method may further include characterizing the coronary plaque by analyzing one or more of the gradients of the quantified radiodensity values in the coronary plaque and the corresponding perivascular tissue, or the ratio of the coronary plaque radiodensity values and the radiodensity values of the corresponding perivascular tissue.

BRIEF DESCRIPTION OF THE DRAWINGS

The disclosed aspects will hereinafter be described in conjunction with the accompanying drawings, which are incorporated in and constitute a part of this specification, and are provided to illustrate and provide a further understanding of example embodiments, and not to limit the disclosed aspects. In the drawings, like designations denote like elements unless otherwise stated.

FIG. 5B illustrates an example of a flowchart that expands on a portion of the flowchart in FIG. 5A for determining characteristics of coronary plaque.

FIG. 13 is a table illustrating an example of a set of patient information.

FIG. 14 is a table 1400 illustrating an example of a set of scan information.

FIG. 15 is a table 1500 illustrating an example of a set of cardiac information.

DETAILED DESCRIPTION OF CERTAIN INVENTIVE ASPECTS

Introduction

Figure 1:
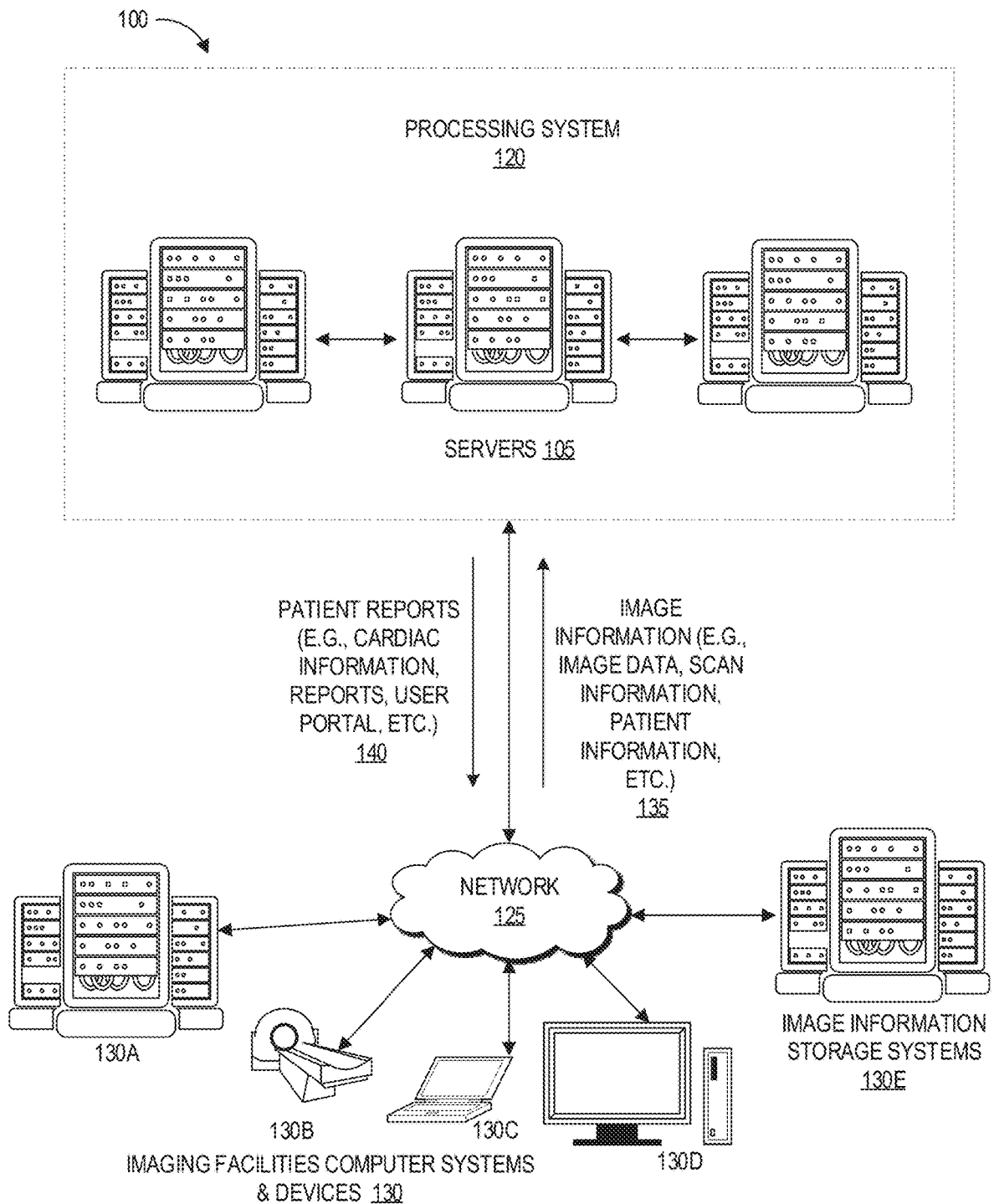
FIG. 1 depicts a schematic of an example of an embodiment of a system 100 that includes a processing system 120 configured to characterize coronary plaque.

Disclosed are methods for identification of high-risk plaques using volumetric characterization of coronary plaque and perivascular adipose tissue data by computed tomography (CT) scanning. The volumetric characterization of the coronary plaque and perivascular adipose tissue allows for determination of the inflammatory status of the plaque by CT scanning. This is of use in the diagnosis, prognosis and treatment of coronary artery disease. While certain example embodiments are shown by way of example in the drawings and will herein be described in detail, these embodiments are capable of various modifications and alternative forms. It should be understood that there is no intent to limit example embodiments to the particular forms disclosed, but on the contrary, example embodiments are to cover all modifications, equivalents, and alternatives falling within the scope of example embodiments.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

Spatially relative terms, such as "beneath," "below," "lower," "above," "upper," and the like may be used herein for ease of description to describe the relationship of one component and/or feature to another component and/or feature, or other component(s) and/or feature(s), as illustrated in the drawings. It will be understood that the spatially relative terms are intended to encompass different orientations of the device in use or operation in addition to the orientation depicted in the figures. The figures are intended to depict example embodiments and should not be interpreted to limit the intended scope of the claims. The accompanying figures are not to be considered as drawn to scale unless explicitly noted.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof. In this specification, the term "and/or" picks out each individual item as well as all combinations of them.

Example embodiments are described herein with reference to cross-section illustrations that are schematic illustrations of idealized embodiments (and intermediate structures). As such, variations from the shapes of the illustrations as a result, for example, of manufacturing techniques and/or tolerances, are to be expected. Thus, embodiments should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belongs. It will be further understood that terms, such as those defined in commonly used dictionaries, should be interpreted as having a meaning that is consistent with their meaning in the context of the relevant art and should not be interpreted in an idealized or overly formal sense unless expressly so defined herein.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

When it is determined that a detailed description related to a related known function or configuration may make the purpose of example embodiments unnecessarily ambiguous, the detailed description thereof may be omitted. Also, terms used herein are defined to appropriately describe example embodiments and thus may be changed depending on a user, the intent of an operator, or a custom. Accordingly, the terms must be defined based on the following overall description within this specification.

In the drawings, the dimensions of layers and regions are exaggerated for clarity of illustration. It will also be understood that when a layer (or tissue) is referred to as being "on" another layer or tissue, it can be directly on the other layer or substrate, or intervening layers may also be present. Further, it will be understood that when a layer is referred to as being "under" another layer, it can be directly under, and one or more intervening layers may also be present. In addition, it will also be understood that when a layer is referred to as being 'between' two layers, it can be the only layer between the two layers, or one or more intervening layers may also be present. Like reference numerals refer to like elements throughout.

Overview of Example Processing System to Characterize Coronary Plaque

This disclosure includes methods and systems of using data generated from images collected by scanning a patient's arteries to identify coronary artery plaques that are at higher risk of causing future heart attack or acute coronary syndrome. In particular, the characteristics of perivascular coronary fat, coronary plaque, and/or the coronary lumen, and the relationship of the characteristics of perivascular coronary fat, coronary plaque, and/or the coronary lumen are discussed to determine ways for identifying the coronary plaque that is more susceptible to implication in future ACS, heart attack and death. The images used to generate the image data may be CT images, CCTA images, or images generated using any applicable technology that can depict the relative densities of the coronary plaque, perivascular fat, and coronary lumen. For example, CCTA images may be used to generate two-dimensional (2D) or volumetric (three-dimensional (3-D)) image data, and this image data may be analyzed to determine certain characteristics that are associated with the radiodensities of the coronary plaque, perivascular fat, and/or coronary lumen. In some implementations, the Hounsfield scale is used to provide a measure of the radiodensity of these features. A Hounsfield unit, as is known, represents an arbitrary unit of x-ray attenuation used for CT scans. Each pixel (2D) or voxel (3D) of a feature in the image data may be assigned a radiodensity value on the Hounsfield scale, and then these values characterizing the features may be analyzed.

In various embodiments, processing of image information may include: (1) determining scan parameters (for example, mA (milliampere), kvP (peak kilovoltage)); (2) determining the scan image quality (e.g., noise, signal-to-noise ratio, contrast-to-noise ratio); (3) measuring scan-specific coronary artery lumen densities (e.g., from a point distal to a coronary artery wall to a point proximal to the coronary artery wall to distal to the coronary artery, and from a central location of the coronary artery to an outer location (e.g., outer relative to radial distance from the coronary artery): (4) measuring scan-specific plaque densities (e.g., from central to outer, abruptness of change within a plaque from high-to-low or low-to-high) as a function of their 3D shape; and (5) measuring scan-specific perivascular coronary fat densities (from close to the artery to far from the artery) as a function of its 3D shape.

From these measurements, which are agnostic to any commonly known features of ischemia-causing atherosclerosis, we can determine a number of characteristics, including but not limited to:

1. A ratio of lumen attenuation to plaque attenuation, wherein the volumetric model of scan-specific attenuation density gradients within the lumen adjusts for reduced luminal density across plaque lesions that are more functionally significant in terms of risk value 2. A ratio of plaque attenuation to fat attenuation, wherein plaques with high radiodensities are considered to present a lower risk, even within a subset of plaques considered "calcified," where there can be a gradation of densities (for example, 130 to 4000 HU) and risk is considered to be reduced as density increases.
3. A ratio of lumen attenuation/plaque attenuation/fat attenuation
4. A ratio of #1-3 as a function of 3D shape of atherosclerosis, which can include a 3D texture analysis of the plaque
5. The 3D volumetric shape and path of the lumen along with its attenuation density from the beginning to the end of the lumen.
6. The totality of plaque and plaque types before and after any given plaque to further inform its risk.
7. Determination of "higher plaque risks" by "subtracting" calcified (high-density) plaques to obtain a better absolute measure of high risk plaques (lower-density plaques). In other words, this particular embodiment involves identifying calcified plaque and excluding it from further analysis of plaque for the purpose of identifying high risk plaques.

The above listed metrics and others can be analyzed together to assess the risk of the plaque being implicated in future heart attack, ACS, ischemia or death. This can be done through development and/or validation of a traditional risk score or through machine learning methods. Factors for analysis from the metrics, that are likely to be associated with heart attack, ACS, ischemia or death, may include: (1) a ratio of [bright lumen:dark plaque]; (2) a ratio of [dark plaque:light fat]; (3) a ratio of [bright lumen:dark plaque: light fat]; and (4) a low ratio of [dark lumen:dark myocardium in 1 vessel area]/[lumen:myocardium in another vessel area]. Some improvements in the disclosed methods and systems include: (1) using numerical values from ratios of [lumen:plaque], [plaque:fat] and [lumen:plaque:fat] instead of using qualitative definitions of atherosclerotic features; (2) using a scan-specific [lumen:plaque attenuation] ratio to characterize plaque; (3) using a scan-specific [plaque:fat attenuation] ratio to characterize plaque; (4) using ratios of [lumen:plaque:fat circumferential] to characterize plaque; and (5) integration of plaque volume and type before and after as a contributor to risk for any given individual plaque.

Atherosclerotic plaque features may change over time with medical treatment (colchicine and statin medications) and while some of these medications may retard progression of plaque, they also have very important roles in promoting the change in plaque. While statin medications may have reduced the overall progression of plaque they may also have actually resulted in an increased progression of calcified plaque and a reduction of non-calcified plaque. This change will be associated with a reduction in heart attack or ACS or death, and the disclosed methods can be used to monitor the effects of medical therapy on plaque risk over time. Also, this method can also be used to identify individuals whose atherosclerotic plaque features or [lumen: plaque]/[plaque:fat]/[lumen:plaque:fat] ratios indicate that they are susceptible to rapid progression or malignant transformation of disease. In addition, these methods can be applied to single plaques or to a patient-basis wherein whole-heart atherosclerosis tracking can be used to monitor risk to the patient for experiencing heart attack (rather than trying to identify any specific plaque as being causal for future heart attack). Tracking can be done by automated co-registration processes of image data associated with a patient over a period of time.

FIG. 1 depicts a schematic of an example of an embodiment of a system 100 that includes a processing system 120 configured to characterize coronary plaque. The processing system 120 include one or more servers (or computers) 105 each configured with one or more processors. The processing system 120 includes non-transitory computer memory components for storing data and non-transitory computer memory components for storing instructions that are executed by the one or more processors data communication interfaces, the instructions configuring the one or more processors to perform methods of analyzing image information. A more detailed example of a server/computer 105 is described in reference to FIG. 4.

The system 100 also includes a network. The processing system 120 is in communication with the network 125. The network 125 may include, as at least a portion of the network 125, the Internet, a wide area network (WAN), a wireless network, or the like. In some embodiments, the processing system 120 is part of a "cloud" implementation, that can be located anywhere that is in communication with the network 125. In some embodiments, the processing system 120 is located in the same geographic proximity as an imaging facility that images and stores patient image data. In other embodiments, the processing system 120 is located remotely from where the patient image data is generated or stored.

FIG. 1 also illustrates in system 100 various computer systems and devices 130 (e.g., of an imaging facility) that are related to generating patient image data and that are also connected to the network 125. One or more of the devices 130 may be at an imaging facility that generates images of a patient's arteries, a medical facility (e.g., a hospital, doctor's office, etc.) or may be the personal computing device of a patient or care provider. For example, as illustrated in FIG. 1, an imaging facility server (or computer) 130A may be connected to the network 125. Also, in this example, a scanner 130B in an imaging facility may be connected to the network 125. One or more other computer devices may also be connected to the network 125. For example, a mobile wireless device including, for example, a tablet, smart phone, watch, or laptop 130C (or any other mobile computer device), a personal computer 130D, and/or and an image information storage system 130E may also be connected to the network 125, and communicate with the processing system 120, and each other, via the network 125.

The information communicated from the devices 130 to the processing system 120 via the network 125 may include image information 135. In various embodiments, the image information 135 may include 2D or 3D image data of a patient, scan information related to the image data, patient information, and other imagery or image related information that relates to a patient. For example, the image information may include patient information including (one or more) characteristics of a patient, for example, age, gender, body mass index (BMI), medication, blood pressure, heart rate, height, weight, race, whether the patient is a smoker or non-smoker, body habitus (for example, the "physique" or "body type" which may be based on a wide range of factors), medical history, diabetes, hypertension, prior coronary artery disease (CAD), dietary habits, drug history, family history of disease, information relating to other previously collected image information, exercise habits, drinking habits, lifestyle information, lab results and the like. One example of a set of patent information is illustrated in a table 1300 in FIG. 13. In some embodiments, the image information includes identification information of the patient, for example, patient's name, patient's address, driver's license number, Social Security number, or indicia of another patient identification. Once the processing system 120 analyzes the image information 135, information relating to a patient 140 may be communicated from the processing system 120 to a device 130 via the network 125. The patient information 140 may include for example, a patient report. Also, the patient information 140 may include a variety of patient information which is available from a patient portal, which may be accessed by one of the devices 130.

In some embodiments, image information comprising a plurality of images of a patient's coronary arteries and patient information/characteristics may be provided from one or more of the devices 130 to the one or more servers 105 of the processing system 120 via a network 125. The processing system 120 is configured to generate coronary artery information using the plurality of images of the patient's coronary arteries to generate two-dimensional and/or three-dimensional data representations of the patient's coronary arteries. Then, the processing system 120 analyzes the data representations to generate patient reports documenting a patient's health conditions and risks related to coronary plaque. The patient reports may include images and graphical depictions of the patient's arteries in the types of coronary plaque in or near the coronary arteries. Using machine learning techniques or other artificial intelligent techniques, the data representations of the patient's coronary arteries may be compared to other patients' data representations (e.g., that are stored in a database) to determine additional information about the patient's health. For example, based on certain plaque conditions of the patient's coronary arteries, the likelihood of a patient having a heart attack or other adverse coronary effect can be determined. Also, for example, additional information about the patient's risk of CAD may also be determined.

Figure 2:
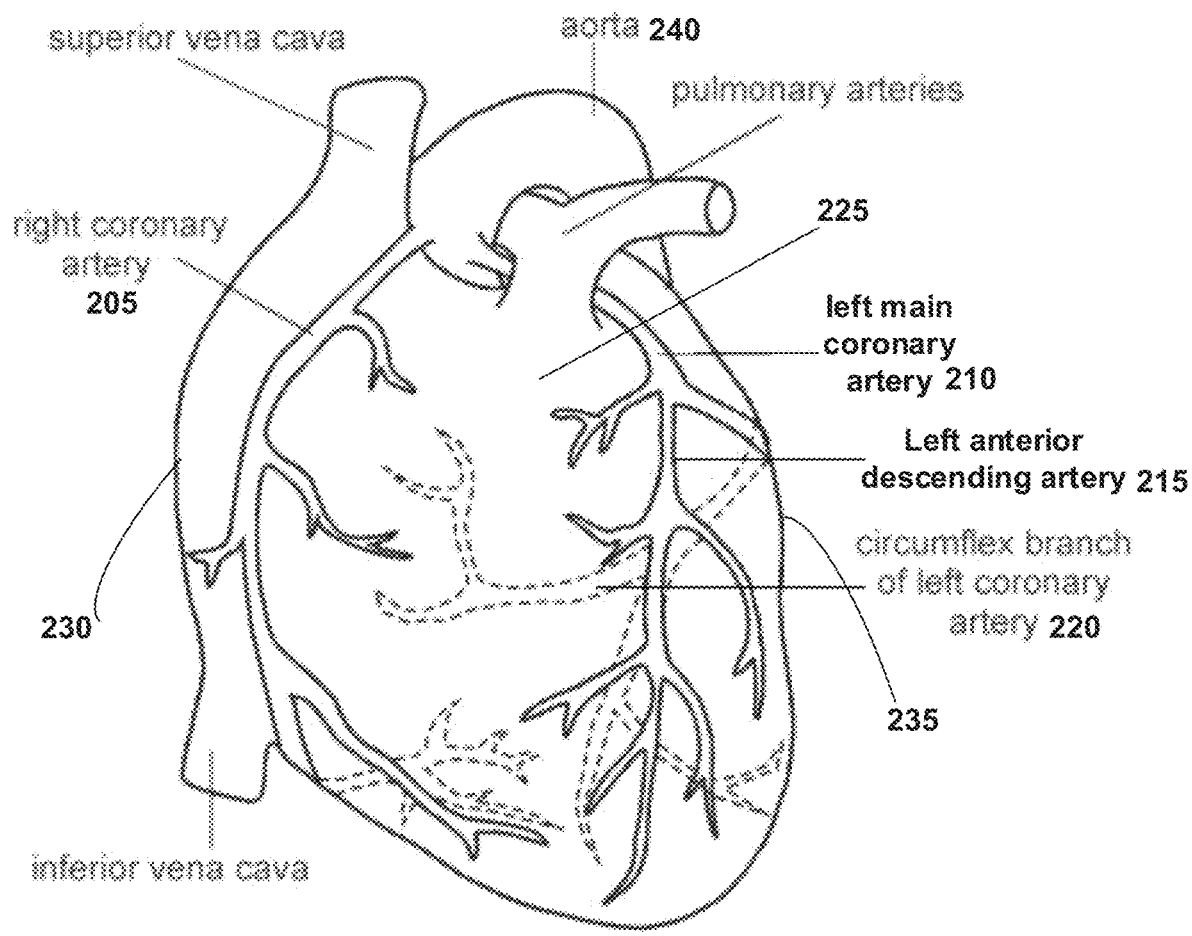
FIG. 2 is a schematic illustrating an example of a heart muscle and its coronary arteries.

FIG. 2 is a schematic illustrating an example of a heart muscle 225 and its coronary arteries. The coronary vasculature includes a complex network of vessels ranging from large arteries to arterioles, capillaries, venules, veins, etc. FIG. 1 depicts a model 220 of a portion of the coronary vasculature that circulates blood to and within the heart and includes an aorta 240 that supplies blood to a plurality of coronary arteries, for example, a left anterior descending (LAD) artery 215, a left circumflex (LCX) artery 220, and a right coronary (RCA) artery 230, described further below. Coronary arteries supply blood to the heart muscle 225. Like all other tissues in the body, the heart muscle 225 needs oxygen-rich blood to function. Also, oxygen-depleted blood must be carried away. The coronary arteries wrap around the outside of the heart muscle 225. Small branches dive into the heart muscle 225 to bring it blood. The examples of methods and systems described herein may be used to determine information relating to blood flowing through the coronary arteries in any vessels extending therefrom. In particular, the described examples of methods and systems may be used to determine various information relating to one or more portions of a coronary artery where plaque has formed which is then used to determine risks associated with such plaque, for example, whether a plaque formation is a risk to cause an adverse event to a patient.

The right side 230 of the heart 225 is depicted on the left side of FIG. 2 (relative to the page) and the left side 235 of the heart is depicted on the right side of FIG. 2. The coronary arteries include the right coronary artery (RCA) 205 which extends from the aorta 240 downward along the right side 230 of the heart 225, and the left main coronary artery (LMCA) 210 which extends from the aorta 240 downward on the left side 235 of the heart 225. The RCA 205 supplies blood to the right ventricle, the right atrium, and the SA (sinoatrial) and AV (atrioventricular) nodes, which regulate the heart rhythm. The RCA 205 divides into smaller branches, including the right posterior descending artery and the acute marginal artery. Together with the left anterior descending artery 215, the RCA 205 helps supply blood to the middle or septum of the heart.

The LMCA 210 branches into two arteries, the anterior interventricular branch of the left coronary artery, also known as the left anterior descending (LAD) artery 215 and the circumflex branch of the left coronary artery 220. The LAD artery 215 supplies blood to the front of the left side of the heart. Occlusion of the LAD artery 215 is often called the widow-maker infarction. The circumflex branch of the left coronary artery 220 encircles the heart muscle. The circumflex branch of the left coronary artery 220 supplies blood to the outer side and back of the heart, following the left part of the coronary sulcus, running first to the left and then to the right, reaching nearly as far as the posterior longitudinal sulcus.

Figure 3:
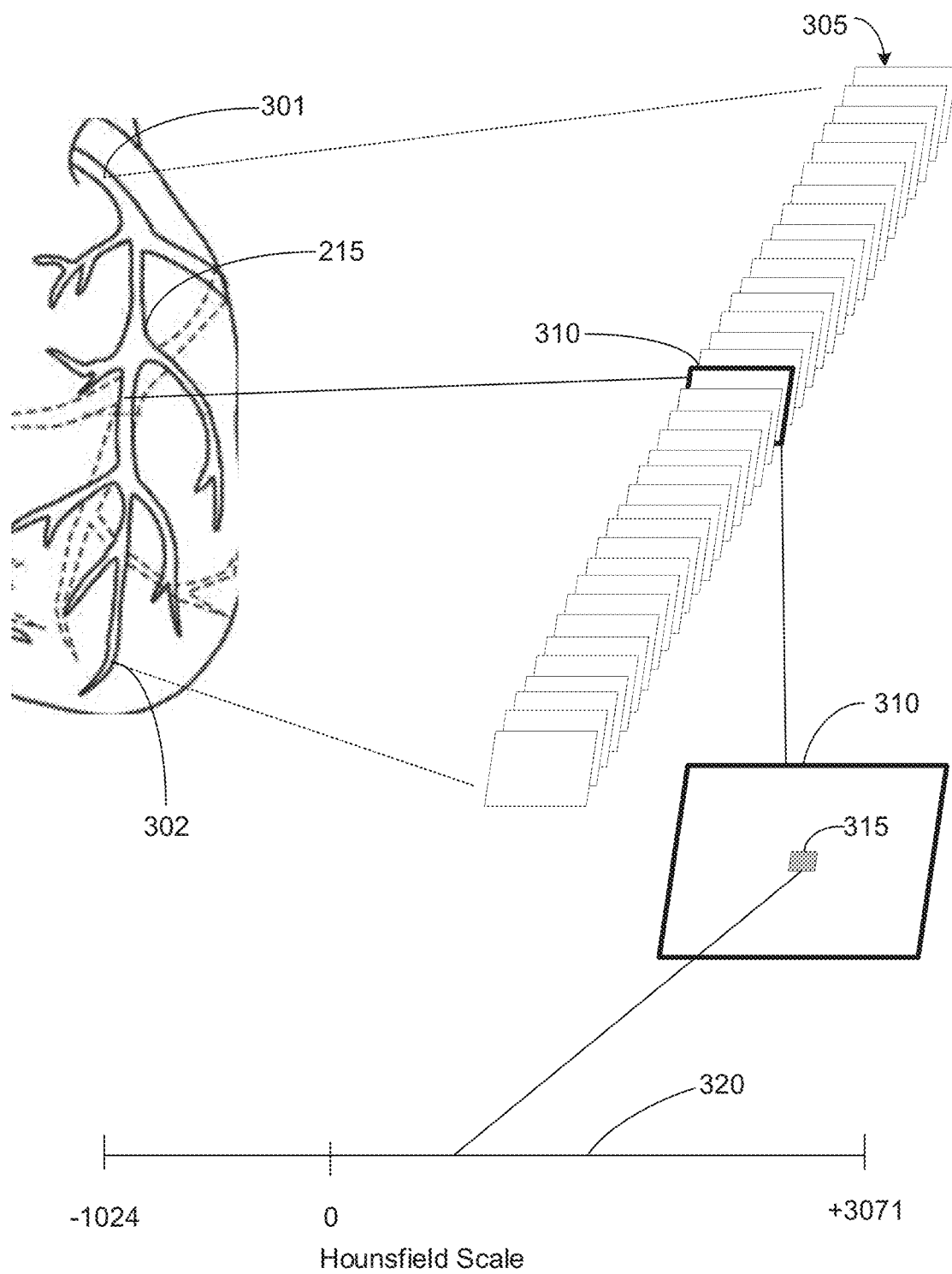
FIG. 3 illustrates an example of a set of images generated from scanning along a coronary artery, including a selected image of a portion of a coronary artery, and how image data may correspond to a value on the Hounsfield Scale.

FIG. 3 illustrates an example of a set of images generated from scanning along a coronary artery, including a selected image of a portion of a coronary artery, and how image data may correspond to a value on the Hounsfield Scale. As discussed in reference to FIG. 1, in addition to obtaining image data, scan information including metrics related to the image data, and patient information including characteristics of the patient may also be collected.

A portion of a heart 225, the LMCA 210, and the LAD artery 215 is illustrated in the example of FIG. 3. A set of images 305 can be collected along portions of the LMCA 210 and the LAD artery 215, in this example from a first point 301 on the LMCA 210 to a second point 302 on the LAD artery 215. In some examples, the image data may be obtained using noninvasive imaging methods. For example, CCTA image data can be generated using a scanner to create images of the heart in the coronary arteries and other vessels extending therefrom. Collected CCTA image data may be subsequently used to generate three-dimensional image models of the features contained in the CCTA image data (for example, the right coronary artery 205, the left main coronary artery 210, the left anterior descending artery 215, the circumflex branch of the left coronary artery 220, the aorta 240, and other vessels related to the heart that appear in the image data.

In various embodiments, different imaging methods may be used to collect the image data. For example, ultrasound or magnetic resonance imaging (MM) may be used. In some embodiments, the imaging methods involve using a contrast agent to help identify structures of the coronary arteries, the contrast agent being injected into the patient prior to the imaging procedure. The various imaging methods may each have their own advantages and disadvantages of usage, including resolution and suitability of imaging the coronary arteries. Imaging methods which may be used to collect image data of the coronary arteries are constantly improving as improvements to the hardware (e.g., sensors and emitters) and software are made. The disclosed systems and methods contemplate using CCTA image data and/or any other type of image data that can provide or be converted into a representative 3D depiction of the coronary arteries, plaque contained within the coronary arteries, and perivascular fat located in proximity to the coronary arteries containing the plaque such that attenuation or radiodensity values of the coronary arteries, plaque, and/or perivascular fat can be obtained.

Referring still to FIG. 3, a particular image 310 of the image data 305 is shown, which represents an image of a portion of the left anterior descending artery 215. The image 310 includes image information, the smallest point of the information manipulated by a system referred to herein generally as a pixel, for example pixel 315 of image 310. The resolution of the imaging system used to capture the image data will affect the size of the smallest feature that can be discerned in an image. In addition, subsequent manipulation of the image may affect the dimensions of a pixel. As one example, the image 310 in a digital format, may contain 4000 pixels in each horizontal row, and 3000 pixels in each vertical column. Pixel 315, and each of the pixels in image data 310 and in the image data 305, can be associated with a radiodensity value that corresponds to the density of the pixel in the image. Illustratively shown in FIG. 3 is mapping pixel 315 to a point on the Hounsfield scale 320. The Hounsfield scale 320 is a quantitative scale for describing radiodensity. The Hounsfield unit scale linear transformation of the original linear attenuation coefficient measurement into one in which the radiodensity of distilled water at standard pressure and temperature is defined as zero Hounsfield units (HU), while the radiodensity of air at standard pressure and temperature is defined as −1000 HU. Although FIG. 3 illustrates an example of mapping pixel 315 of image 310 to a point on the Hounsfield scale 320, such an association of a pixel to a radiodensity value can also be done with 3D data. For example, after the image data 305 is used to generate a three-dimensional representation of the coronary arteries.

Once the data has been obtained and rendered into a three-dimensional representation, various processes can be performed on the data to identify areas of analysis. For example, a three-dimensional depiction of a coronary artery may be segmented to define a plurality of portions of the artery and identified as such in the data. In some embodiments, the data may be filtered (e.g., smoothed) by various methods to remove anomalies that are the result of scanning or other various errors. Various known methods for segmenting and smoothing the 3D data may be used, and therefore for brevity of the disclosure will not be discussed in any further detail herein.

Figure 4A:
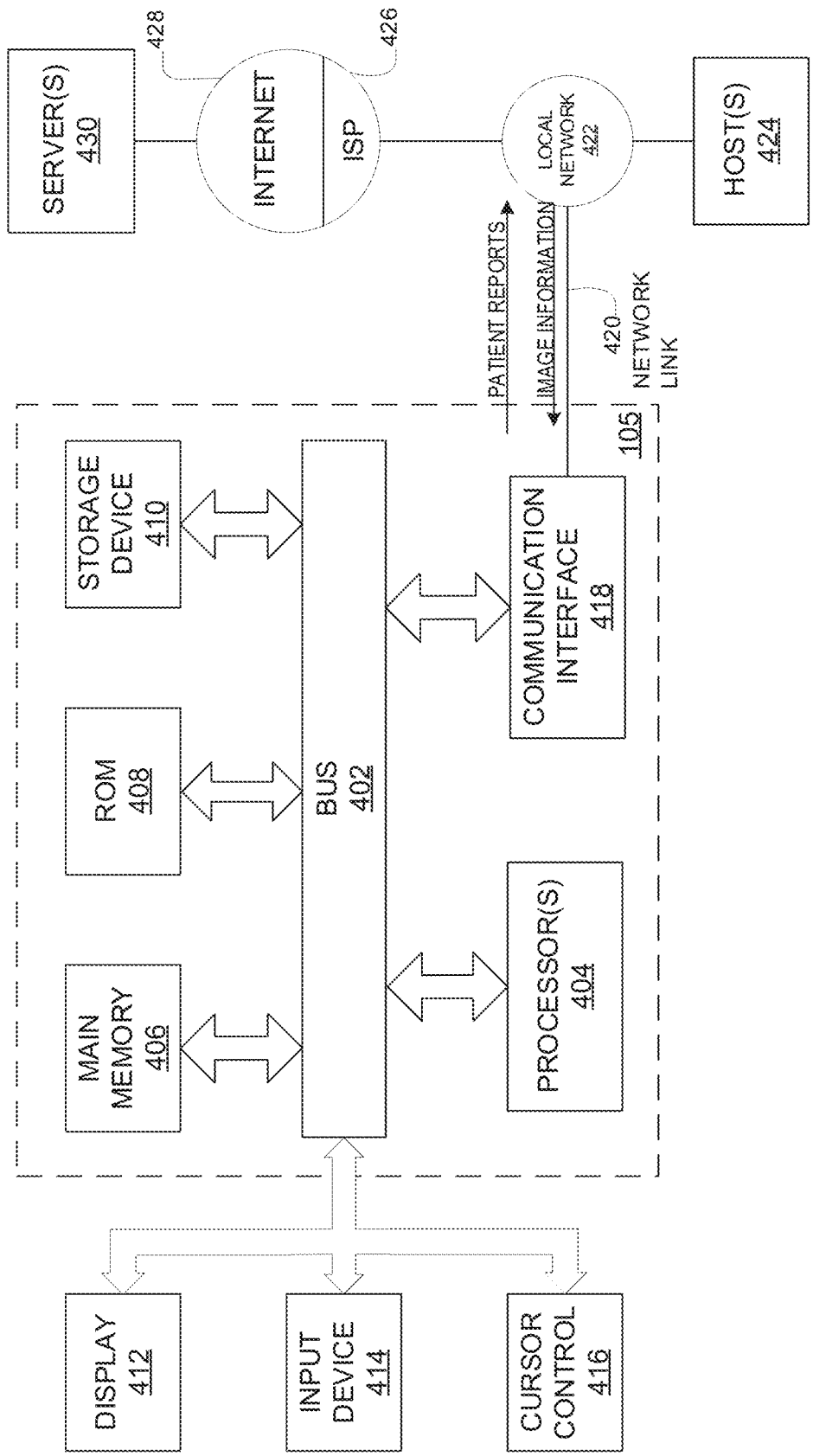
FIG. 4A is a block diagram that illustrates a computer system 400 upon which various embodiments may be implemented.

FIG. 4A is a block diagram that illustrates a computer system 400 upon which various embodiments may be implemented. Computer system 400 includes a bus 402 or other communication mechanism for communicating information, and a hardware processor, or multiple processors, 404 coupled with bus 402 for processing information. Hardware processor(s) 404 may be, for example, one or more general purpose microprocessors.

Computer system 400 also includes a main memory 406, such as a random access memory (RAM), cache and/or other dynamic storage devices, coupled to bus 402 for storing information and instructions to be executed by processor 404. Main memory 406 also may be used for storing temporary variables or other intermediate information during execution of instructions to be executed by processor 404. Such instructions, when stored in storage media accessible to processor 404, render computer system 400 into a special-purpose machine that is customized to perform the operations specified in the instructions. The main memory 406 may, for example, include instructions that analyze image information to determine characteristics of coronary features (e.g., plaque, perivascular fat and coronary arteries) to produce patient reports containing information that characterizes aspects of the patients health relating to their coronary arteries. For example, one or more metrics may be determined, the metrics including one or more of a slope/gradient of a feature, a maximum density, minimum density, a ratio of a slope of one feature to the slope of another feature, a ratio of a maximum density of one feature to the maximum density of another feature, a ratio of a minimum density of a feature to the minimum density of the same feature, or a ratio of the minimum density of a feature to the maximum density of another feature.

Computer system 400 further includes a read only memory (ROM) 408 or other static storage device coupled to bus 402 for storing static information and instructions for processor 404. A storage device 410, such as a magnetic disk, optical disk, or USB thumb drive (Flash drive), etc., is provided and coupled to bus 402 for storing information and instructions.

Computer system 400 may be coupled via bus 402 to a display 412, such as a cathode ray tube (CRT) or LCD display (or touch screen), for displaying information to a computer user. An input device 414, including alphanumeric and other keys, is coupled to bus 402 for communicating information and command selections to processor 404. Another type of user input device is cursor control 416, such as a mouse, a trackball, or cursor direction keys for communicating direction information and command selections to processor 404 and for controlling cursor movement on display 412. This input device typically has two degrees of freedom in two axes, a first axis (e.g., x) and a second axis (e.g., y), that allows the device to specify positions in a plane. In some embodiments, the same direction information and command selections as cursor control may be implemented via receiving touches on a touch screen without a cursor.

Computing system 400 may include a user interface module to implement a GUI that may be stored in a mass storage device as computer executable program instructions that are executed by the computing device(s). Computer system 400 may further, as described below, implement the techniques described herein using customized hard-wired logic, one or more ASICs or FPGAs, firmware and/or program logic which in combination with the computer system causes or programs computer system 400 to be a special-purpose machine. According to one embodiment, the techniques herein are performed by computer system 400 in response to processor(s) 404 executing one or more sequences of one or more computer readable program instructions contained in main memory 406. Such instructions may be read into main memory 406 from another storage medium, such as storage device 410. Execution of the sequences of instructions contained in main memory 406 causes processor(s) 404 to perform the process steps described herein. In alternative embodiments, hard-wired circuitry may be used in place of or in combination with software instructions.

Various forms of computer readable storage media may be involved in carrying one or more sequences of one or more computer readable program instructions to processor 404 for execution. For example, the instructions may initially be carried on a magnetic disk or solid state drive of a remote computer. The remote computer can load the instructions into its dynamic memory and send the instructions over a telephone line using a modem. A modem local to computer system 400 can receive the data on the telephone line and use an infra-red transmitter to convert the data to an infra-red signal. An infra-red detector can receive the data carried in the infra-red signal and appropriate circuitry can place the data on bus 402. Bus 402 carries the data to main memory 406, from which processor 404 retrieves and executes the instructions. The instructions received by main memory 406 may optionally be stored on storage device 410 either before or after execution by processor 404.

Computer system 400 also includes a communication interface 418 coupled to bus 402. Communication interface 418 provides a two-way data communication coupling to a network link 420 that is connected to a local network 422. For example, communication interface 418 may be an integrated services digital network (ISDN) card, cable modem, satellite modem, or a modem to provide a data communication connection to a corresponding type of telephone line. As another example, communication interface 418 may be a local area network (LAN) card to provide a data communication connection to a compatible LAN (or WAN component to communicate with a WAN). Wireless links may also be implemented. In any such implementation, communication interface 418 sends and receives electrical, electromagnetic or optical signals that carry digital data streams representing various types of information.

Network link 420 typically provides data communication through one or more networks to other data devices. For example, network link 420 may provide a connection through local network 422 to a host computer 424 or to data equipment operated by an Internet Service Provider (ISP) 426. ISP 426 in turn provides data communication services through the world wide packet data communication network now commonly referred to as the "Internet" 428. Local network 422 and Internet 428 both use electrical, electromagnetic or optical signals that carry digital data streams. The signals through the various networks and the signals on network link 420 and through communication interface 418, which carry the digital data to and from computer system 400, are example forms of transmission media.

Computer system 400 can send messages and receive data, including program code, through the network(s), network link 420 and communication interface 418. In the Internet example, a server 430 might transmit a requested code for an application program through Internet 428, ISP 426, local network 422 and communication interface 418.

The received code may be executed by processor 404 as it is received, and/or stored in storage device 410, or other non-volatile storage for later execution.

Accordingly, in an embodiment, the computer system 105 comprises a non-transitory computer storage medium storage device 410 configured to at least store image information of patients. The computer system 105 can also include non-transitory computer storage medium storage that stores instructions for the one or more processors 404 to execute a process (e.g., a method) for characterization of coronary plaque tissue data and perivascular tissue data using image data gathered from a computed tomography (CT) scan along a blood vessel, the image information including radiodensity values of coronary plaque and perivascular tissue located adjacent to the coronary plaque. Executing the instructions, the one or more processors 404 can quantify, in the image data, the radiodensity in regions of coronary plaque, quantify in the image data, radiodensity in at least one region of corresponding perivascular tissue adjacent to the coronary plaque, determine gradients of the quantified radiodensity values within the coronary plaque and the quantified radiodensity values within the corresponding perivascular tissue, determine a ratio of the quantified radiodensity values within the coronary plaque and the corresponding perivascular tissue, and characterizing the coronary plaque by analyzing one or more of the gradients of the quantified radiodensity values in the coronary plaque and the corresponding perivascular tissue, or the ratio of the coronary plaque radiodensity values and the radiodensity values of the corresponding perivascular tissue.

Various embodiments of the present disclosure may be a system, a method, and/or a computer program product at any possible technical detail level of integration. The computer program product may include a computer readable storage medium (or mediums) having computer readable program instructions thereon for causing a processor to carry out aspects of the present disclosure. For example, the functionality described herein may be performed as software instructions are executed by, and/or in response to software instructions being executed by, one or more hardware processors and/or any other suitable computing devices. The software instructions and/or other executable code may be read from a computer readable storage medium (or mediums).

The computer readable storage medium can be a tangible device that can retain and store data and/or instructions for use by an instruction execution device. The computer readable storage medium may be, for example, but is not limited to, an electronic storage device (including any volatile and/or non-volatile electronic storage devices), a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a solid state drive, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions (as also referred to herein as, for example, "code," "instructions," "module," "application," "software application," and/or the like) for carrying out operations of the present disclosure may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. Computer readable program instructions may be callable from other instructions or from itself, and/or may be invoked in response to detected events or interrupts. Computer readable program instructions configured for execution on computing devices may be provided on a computer readable storage medium, and/or as a digital download (and may be originally stored in a compressed or installable format that requires installation, decompression or decryption prior to execution) that may then be stored on a computer readable storage medium. Such computer readable program instructions may be stored, partially or fully, on a memory device (e.g., a computer readable storage medium) of the executing computing device, for execution by the computing device. The computer readable program instructions may execute entirely on a user's computer (e.g., the executing computing device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart(s) and/or block diagram(s) block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks. For example, the instructions may initially be carried on a magnetic disk or solid state drive of a remote computer. The remote computer may load the instructions and/or modules into its dynamic memory and send the instructions over a telephone, cable, or optical line using a modem. A modem local to a server computing system may receive the data on the telephone/cable/optical line and use a converter device including the appropriate circuitry to place the data on a bus. The bus may carry the data to a memory, from which a processor may retrieve and execute the instructions. The instructions received by the memory may optionally be stored on a storage device (e.g., a solid state drive) either before or after execution by the computer processor.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. In addition, certain blocks may be omitted in some implementations. The methods and processes described herein are also not limited to any particular sequence, and the blocks or states relating thereto can be performed in other sequences that are appropriate.

It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions. For example, any of the processes, methods, algorithms, elements, blocks, applications, or other functionality (or portions of functionality) described in the preceding sections may be embodied in, and/or fully or partially automated via, electronic hardware such application-specific processors (e.g., application-specific integrated circuits (ASICs)), programmable processors (e.g., field programmable gate arrays (FPGAs)), application-specific circuitry, and/or the like (any of which may also combine custom hard-wired logic, logic circuits, ASICs, FPGAs, etc. with custom programming/execution of software instructions to accomplish the techniques).

Any of the above-mentioned processors, and/or devices incorporating any of the above-mentioned processors, may be referred to herein as, for example, "computers," "computer devices," "computing devices," "hardware computing devices," "hardware processors," "processing units," and/or the like. Computing devices of the above-embodiments may generally (but not necessarily) be controlled and/or coordinated by operating system software, such as Mac OS, iOS, Android, Chrome OS, Windows OS (e.g., Windows XP, Windows Vista, Windows 7, Windows 8, Windows 10, Windows Server, etc.), Windows CE, Unix, Linux, SunOS, Solaris, Blackberry OS, VxWorks, or other suitable operating systems. In other embodiments, the computing devices may be controlled by a proprietary operating system. Conventional operating systems control and schedule computer processes for execution, perform memory management, provide file system, networking, I/O services, and provide a user interface functionality, such as a graphical user interface ("GUI"), among other things.

Figure 4B:
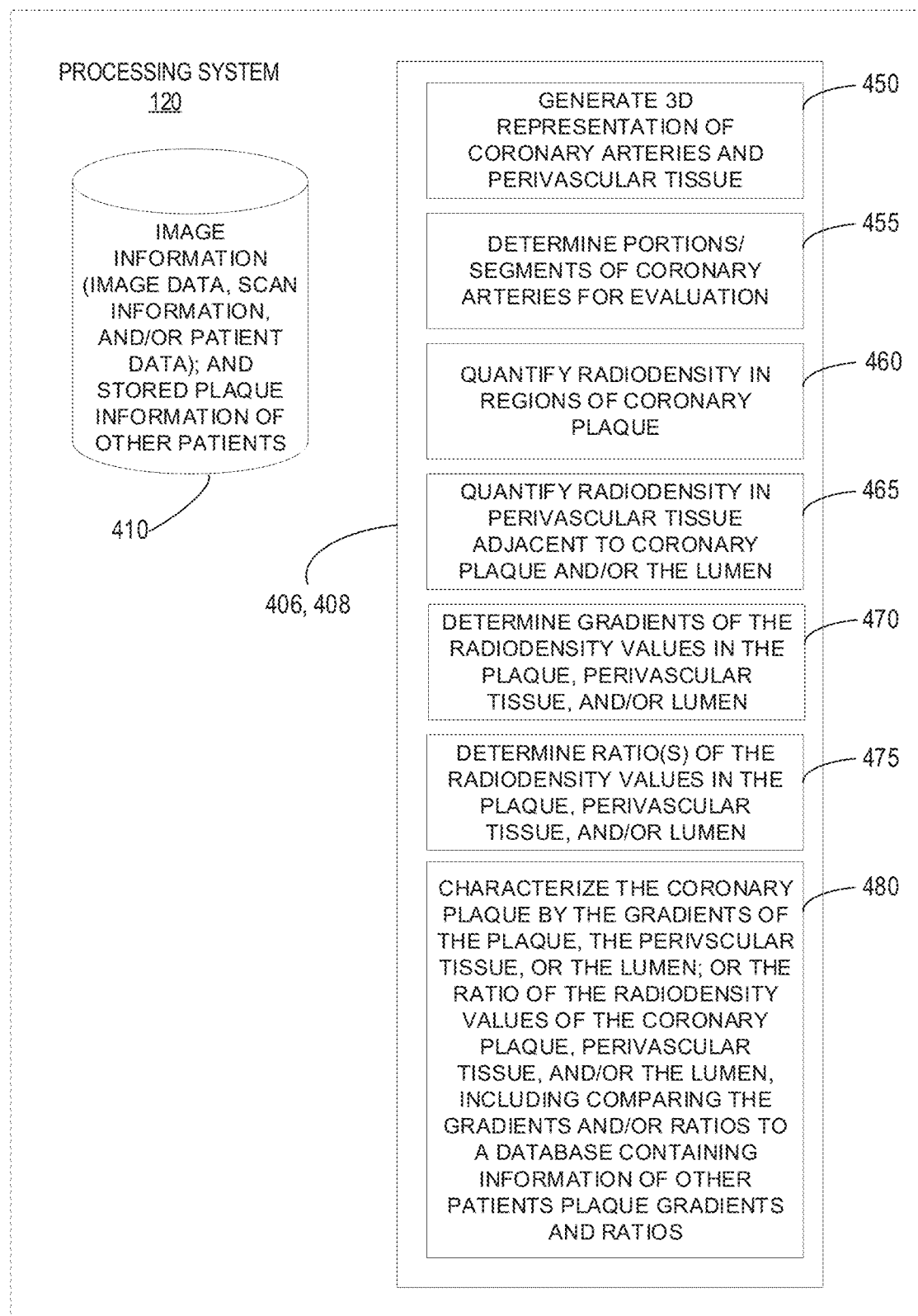
FIG. 4B is a block diagram that illustrates computer modules in a computer system 400 which may implement various embodiments.

FIG. 4B is a block diagram that illustrates examples of representative instructions which may be executed by one or more computer hardware processors in one or more computer modules in a representative processing system (computer system) 120 which may implement various embodiments described herein. As illustrated in FIG. 1, the processing system 120 can be implemented in one computer (for example, a server) or in 2 or more computers (two or more servers). Although the instructions are represented in FIG. 4B as being in seven modules 450, 455, 460, 465, 470, 475, 480, in various implementations the executable instructions may be in fewer modules, including a single module, or more modules.

The processing system 120 includes image information stored on a storage device 410, which may come from the network 125 illustrated in FIG. 1. The image information may include image data, scan information, and/or patient data. In this example, the storage device 410 also includes stored plaque information of other patients. For example, the stored plaque information of other patients may be stored in a database on the storage device 410. In other examples, stored plaque information of other patients is stored on a storage device that is in communication with processing system 120. The other patients' stored plaque information may be a collection of information from one, dozens, hundreds, thousands, tens of thousands, hundreds of thousands, or millions of patients, or more.

The information for each patient may include characterizations of that patient's plaque, such as densities and density gradients of the patient's plaque, and the location of the plaque relative to the perivascular tissue near or adjacent to the plaque. The information for each patient may include patient information as illustrated in FIG. 13. For example, the information may include one or more of sex, age, BMI (body mass index), medication, blood pressure, heart rate, weight, height, race, body habitus, smoking history, history or diagnosis of diabetes, history or diagnosis of hypertension, prior coronary artery disease, family history of coronary artery disease and/or other diseases, or one or more lab results (e.g., blood test results). The information for each patient may include scan information as illustrated in FIG. 14. For example, the information may include one or more of contrast-to-noise ratio, signal-to-noise ratio, tube current, tube voltage, contrast type, contrast volume, flow rate, flow duration, slice thickness, slice spacing, pitch, vasodilator, beta blockers, recon option whether it's iterative or filter back projection, recon type whether it's standard or high resolution, display field-of-view, rotation speed, gating whether it's perspective triggering or retrospective gating, stents, heart rate, or blood pressure. The information for each patient may also include cardiac information as illustrated in FIG. 15. For example, the information may include characterizations of plaque including one or more of density, volume, geometry (shape), location, remodeling, baseline anatomy (for diameter, length), compartments (inner, outer, within), stenosis (diameter, area), myocardial mass, plaque volume, and/or plaque composition, texture, or uniformity.

The processing system 120 also includes memory 406, 408, which may be main memory of the processing system or read only memory (ROM). The memory 406, 408 stores instructions executable by one or more computer hardware processors 404 (groups of which referred to herein as "modules") to characterize coronary plaque. The memory 406, 408 will be collectively referred to, in reference to this diagram, as memory 406 for the sake of brevity. Examples of the functionality that is performed by the executable instructions are described below.

Memory 406 includes module 450 that generates, from the image data stored on the storage device 410, 2-D or 3-D representations of the coronary arteries, including plaque, and perivascular tissue that is located adjacent to or in proximity of the coronary arteries in the plaque. The generation of the 2-D or 3-D representations of the coronary arteries may be done from a series of images 305 (e.g., CCTA images) is described above in reference to FIG. 3. Once the representation of the coronary arteries are generated, different portions or segments of the coronary arteries can be identified for evaluation. For example, portions of interest of the right coronary artery 205, the left anterior descending artery 215, or the circumflex branch of the left coronary artery 220 may be identified as areas of analysis (areas of interest) based on input from a user, or based on a feature determined from the representation of the coronary artery (plaque).

In module 460, the one or more computer hardware processors quantify radiodensity in regions of coronary plaque. For example, the radiodensity in regions of coronary plaque are set to a value on the Hounsfield scale. In module 465, the one or more computer hardware processors quantify radiodensity of perivascular tissue that is adjacent to the coronary plaque, and quantify radiodensity value of the lumen of the vessel of interest. In module 470, the one or more computer hardware processors determine gradients of the radiodensity values of the plaque the perivascular tissue and/or the lumen. In module 475, the one or more computer hardware processors determine one or more ratios of the radiodensity values in the plaque, perivascular tissue, and/or the lumen. Next, in module 480, the one or more computer hardware processors characterize the coronary plaque using the gradients of the plaque, the perivascular tissue, and/or the lumen, and/or characterize ratio of the radiodensity values of the coronary plaque to perivascular tissue and/or the lumen including comparing the gradients and or ratios to a database containing information of other patients plaque gradients and ratios. For example, the gradients and/or the ratios are compared to patient data that stored on storage device 410. Determining gradients and ratios of the plaque the perivascular tissue and the lumen are described in more detail with reference to FIGS. 6-12.

Figure 5A:
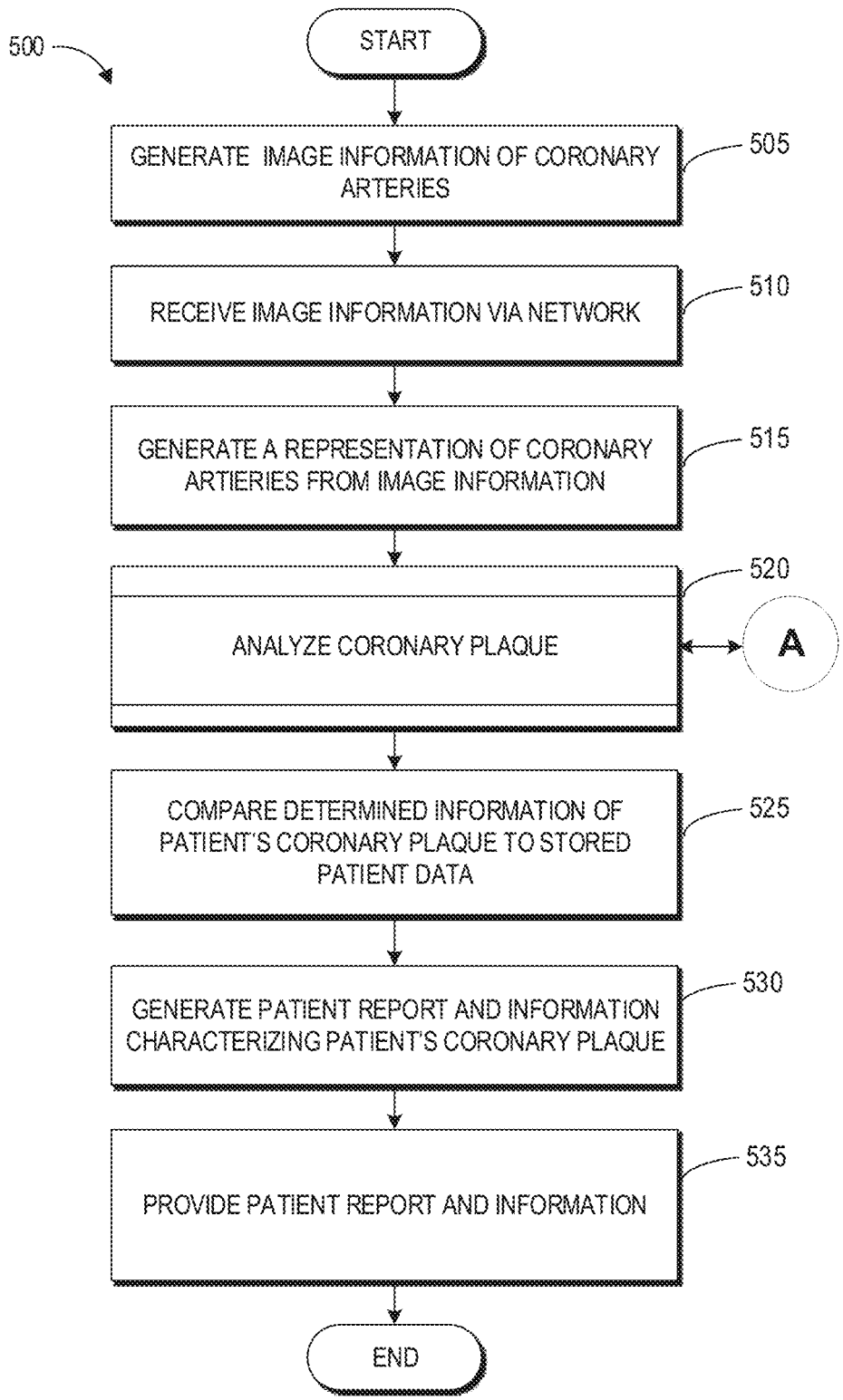
FIG. 5A illustrates an example of a flowchart of a process for analyzing coronary plaque.

FIG. 5A illustrates an example of a flowchart of a process 500 for analyzing coronary plaque. At block 505, the process 500 generates image information including image data relating to coronary arteries. In various embodiments, this may be done by a scanner 130B (FIG. 1). At block 510, a processing system may receive image information via a network 125 (FIG. 1), the image information including the image data. At block 515, the process 500 generates a 3D representation of the coronary arteries including perivascular fat and plaque on the processing system. The functionality of blocks 505, 510, and 515, can be performed, for example, using various scanning techniques (e.g., CCTA) to generate image data, communication techniques to transfer data over the network, and processing techniques to generate the 3D representation of the coronary arteries from the image data.

At block 520, the processing system performs a portion of the process 500 to analyze the coronary plaque, which is described in further detail in reference to process 550 of FIG. 5B. Additional details of this process to analyze the coronary plaque in particular in reference to FIGS. 6-12.

FIG. 5B illustrates an example of a flowchart that expands on a portion of the flowchart in FIG. 5A for determining characteristics of coronary plaque. Referring now to FIG. 5B, at block 555, process 550 can utilize the one or more processors 404 to quantify the radiodensity in regions of coronary plaque. At block 560, the process 550 can utilize the one or more processors 404 to quantify, in the image data, radiodensity in at least one region of corresponding perivascular tissue, meaning perivascular tissue that is adjacent to the coronary plaque. At block 565, the process 550 determines gradients of the quantified radiodensity values within the coronary plaque and the quantified radiodensity values within the corresponding perivascular tissue. The one or more processors 404 can be the means to determine these gradients. At block 570, the process 550 may determine a ratio of the quantified radiodensity values within the coronary plaque and the corresponding perivascular tissue. For example, the perivascular tissue that is adjacent to the coronary plaque. The one or more processors 404 can determine these ratios. At block 575, process 550 can utilize the one or more processors 404 to characterize the coronary plaque by analyzing one or more of the gradients of the quantified radiodensity values in the coronary plaque and the corresponding perivascular tissue, or the ratio of the coronary plaque radiodensity values and the radiodensity values of the corresponding perivascular tissue. The process 550 can then return back to process 500 as illustrated by the circle A.

Referring again to FIG. 5A, at block 525, the process 500 may compare determined information of a particular patient's coronary plaque to stored patient data, for example patient data stored on storage device 410. An example of the coronary plaque information of a particular patient that can be compared to stored patient data is illustrated in FIG. 15. To better understand the particular patient's coronary plaque information, and/or to help determine the particular patient's coronary plaque information, one or more of the scan information illustrated in FIG. 14 may be used. Also, when comparing a particular patient's coronary plaque information to previously stored coronary plaque information, one or more characteristics of the patient may be compared, including, for example, one or more of the characteristics of a patient that are shown in FIG. 13. In some examples, the coronary plaque information of the particular patient being examined may be compared to or analyzed in reference to a patient who has one or more of the same or similar patient characteristics. For example, the patient being examined may be compared to a patient that has the same or similar characteristics of sex, age, BMI, medication, blood pressure, heart rate, weight, height, race, body habitus, smoking, diabetes, hypertension, prior coronary artery disease, family history, and lab results. Such comparisons can be done through various means, for example machine learning and/or artificial intelligence techniques. In some examples, neural network is used to compare a patient's coronary artery information to numerous (e.g., 10,000+) other patients' coronary artery information. For such patients that have similar patient information and similar cardiac information (for example, the characteristics shown in FIG. 15), risk assessments of the plaque of the patient being examined may be determined.

Figure 6:
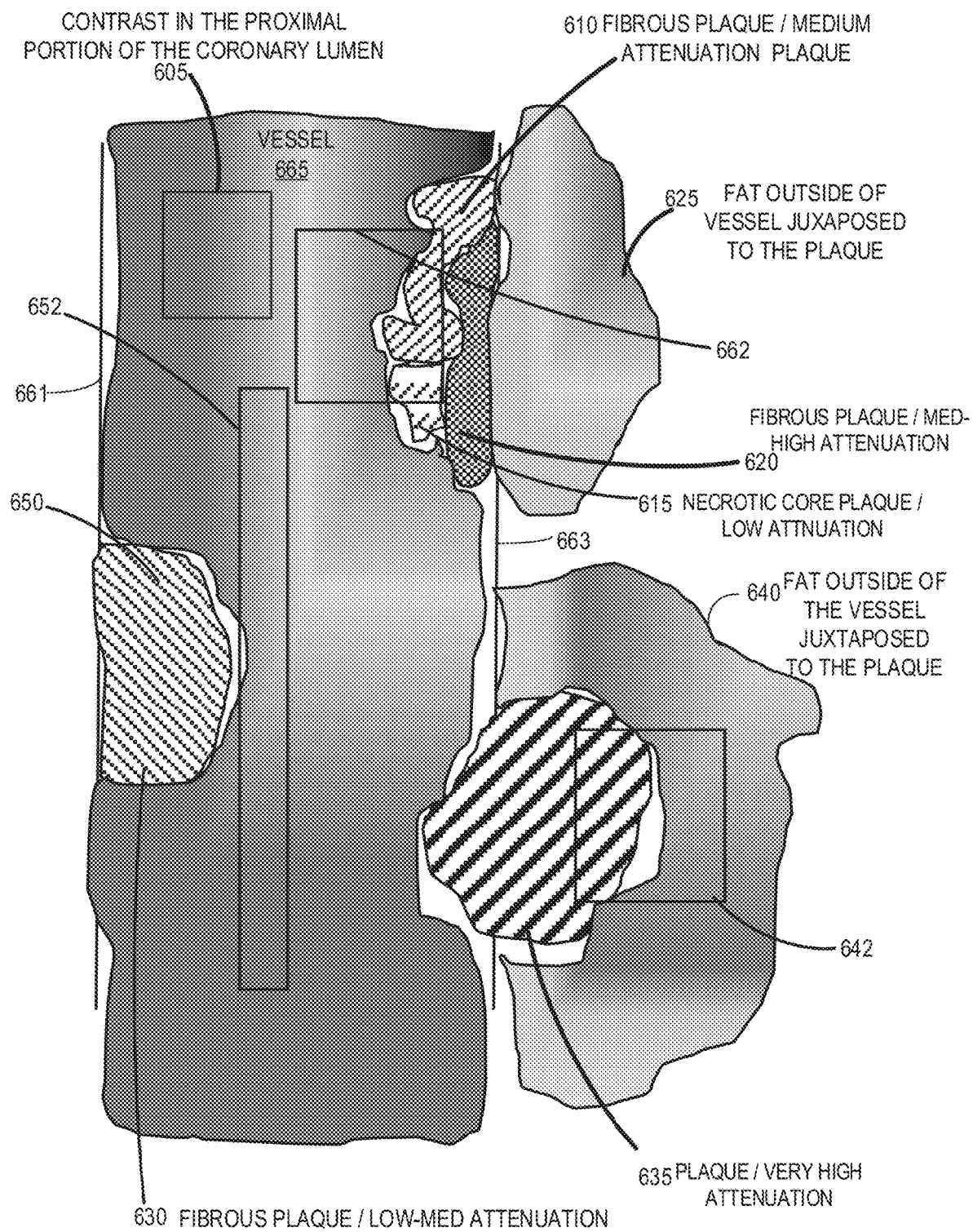
FIG. 6 illustrates a representation of image data depicting an example of a portion of a coronary artery 665 (sometimes referred to herein as a "vessel" for ease of reference).

FIG. 6 illustrates a representation of image data depicting an example of a portion of a coronary artery 665 (sometimes referred to herein as a "vessel" for ease of reference). Although FIG. 6 is a two-dimensional (2D) illustration, the image data analyzed may be two dimensional or three dimensional (e.g., volumetric). FIG. 6 also illustrates examples of plaque located in the vessel 665 and perivascular fat located adjacent to the vessel 665. FIG. 6 further illustrates examples of areas (shown on FIG. 6 as rectangles) that may contain at least a portion of the vessel 665, plaque that is in the vessel 665, or perivascular fat that is adjacent to the vessel 665, where these areas indicate portions of one or more of the vessel 665, plaque, or perivascular fat that may be analyzed to determine densities, density gradients, and/or density ratios of the vessel 665, plaque, or perivascular fat to determine one or more characteristics of a patient's coronary arteries. As illustrated in FIG. 6, the vessel 665 includes a vessel wall 661 and a vessel wall 663 which are depicted as boundary lines to provide a graphical reference of where plaque and fat are located relative to the vessel 665 in FIG. 6. The vessel wall 661 and the vessel wall 662 may sometimes be referred to herein as a first vessel wall and a second vessel wall, or vice versa. The line delineating the vessel walls 661, 663 indicate an outer boundary of the vessel walls 661, 663. In the example illustrated in FIG. 6, all of the fat 625, 640 is located outside of the vessel walls 661, 663, and all of the plaque 610, 620, 635, 650 is located within the vessel walls 661, 663.

Plaque can be characterized by its attenuation that is exhibited in images of the coronary arteries. For example, plaque can be characterized as being low attenuation plaque, a medium attenuation plaque, a high attenuation plaque, or very high attenuation plaque. In some cases, these characterizations are not exactly precise and may be affected by the methods and processes used to collect the images of the coronary arteries. In some examples, low attenuation plaque can have a density of about 0 to about 70. In some examples, medium attenuation plaque can have a density of about 70 to about 350 In some examples, high attenuation plaque can have a density of about 350 to about 1000. In some examples, very high attenuation plaque can have a density of more than 1000.

FIG. 6 illustrates examples of different types of plaque that may be contained within the vessel walls 661 and 663 of the vessel 665, according to some embodiments. In an example, the plaque may be fibrous plaque 610 having a medium attenuation characteristic, inside the vessel wall 663 and extending towards the interior of the vessel 665. In this example the fibrous plaque 610 has other types of plaque adjacent to it within the vessel wall 663, and fat disposed outside of the vessel 665 juxtaposed or adjacent to the fibrous plaque 610. As illustrated in FIG. 6, disposed adjacent to the fibrous plaque 610 is necrotic core plaque 615 which has a low attenuation characteristic. FIG. 6 also illustrates an example of a plaque 620 having medium-high attenuation characteristics, that is also disposed (or located) adjacent to the fibrous plaque 610. In this example, plaque 620 is also disposed adjacent to necrotic core plaque 615, such that plaque 620 is at least partially between the plaque fibrous 610 and the necrotic core plaque 615, and the outside boundary of the vessel wall 663. FIG. 6 also illustrates an example of a very high attenuation plaque 635 disposed within vessel wall 663, but protruding out of the vessel 665 such that vessel wall 663 extends outward (i.e., away from the center of the vessel 665) around plaque 635. In another example, FIG. 6 illustrates a fibrous plaque 650 having a medium attenuation characteristics (i.e., the attenuation characteristics not being as high as fibrous plaque 610) that is disposed adjacent to and within the vessel wall 661. As illustrated in FIG. 6, the fibrous plaque 650 generally extends towards the center of the vessel 665.

FIG. 6 further illustrates examples of fat that is outside of the vessel adjacent to (or at least in proximity of) the vessel 665. The fat illustrated in FIG. 6 is also in proximity to and/or adjacent to one or more of the plaques 610, 615, 620, 635. In one example, fat 625 is along a portion of the vessel wall 623, adjacent to the vessel wall 663, and juxtaposed to the plaque 620, such that it is adjacent to plaque 620 and in the proximity of plaque 610 and 615. In another example illustrated in FIG. 6, fat 640 as shown outside of the vessel wall 662 and adjacent to plaque 635. In this example, fat 640 at least partially surrounds the portion of plaque 635 extending from the vessel 665 such that a portion of fat 640 is adjacent to the vessel wall 663 on two or more sides of plaque 635.

Identifying high risk plaques may be dependent upon the interplay between contrast attenuation's in the coronary lumen, attenuation patterns of plaque, and fat attenuation patterns. As mentioned above, FIG. 6 also illustrates boxes indicating examples of areas that include all or portions vessel 665, perivascular fat, and/or plaque, for analysis of density gradients and density ratios. In the illustrated boxes in FIG. 6, as well as similar boxes illustrated in FIGS. 7, 10, 11, and 12, the boxes are shown as two-dimensional rectangles the cover portions of the representation of the image data depicting a portion of a coronary artery (vessel 665), plaque, and fat. As will be discussed below in reference to FIGS. 11 and 12, the portion of the image data that is analyzed may be, in some examples, data representing a one-dimensional vector of pixels that is in the rectangular box. In other words, image data along the line that is in the rectangular box. In other examples, the portion of the image data that is analyzed may be a two dimensional vector of pixels that is in the rectangular box. In other words, image data contained in two or more adjacent lines that are in the rectangular box. In some cases for the two dimensional vector of pixels, the image data in the two or more adjacent lines may be processed to form a one dimensional vector. For example, the image data in the two or more adjacent lines of image data may be averaged, which may help reduce the effect of noise. In some cases, the image data may be filtered to reduce the effect of noise. In some examples, filtering may occur before the image data is analyzed for gradient, ratios, slope, minimum density, maximum density, etc.

FIG. 6 illustrates an example of an area, indicated by box 605, where contrast attenuation patterns in a proximal portion of the coronary lumen can be analyzed, box 605 extending from a central area of the vessel 665 towards the vessel wall 661. FIG. 6 illustrates another example of an area, indicated by box 652, where contrast attenuation patterns in a portion of the coronary lumen of vessel 665 can be analyzed, box 652 extending longitudinally relative to vessel 665 from a central area of the vessel 665 towards the vessel wall 661. FIG. 6 further illustrates an example of an area, indicated by box 662, where contrast attenuation patterns of a portion of the lumen, a portion of fibrous plaque 610 and plaque 620 can be analyzed, box 662 thus covering a portion of the vessel 665 and a portion of fibrous plaque 610 and plaque 620. FIG. 6 further illustrates an example of an area indicated by box 642, where contrast attenuation patterns of a portion of plaque 635 and a portion of fat 640 positioned adjacent to plaque 635 can be analyzed, box 642 extending over a portion of plaque 635 and a portion of fat 640. Information determined by analyzing various aspects of the density of coronary artery features (e.g., the lumen, the plaque, and/or the perivascular fat) can be combined with other information to determine characteristics of a patient's arteries. In some examples, the determined information may include for any of the lumen, plaque or perivascular fat, one or more of a slope/gradient of a feature, a maximum density, a minimum density, a ratio of a slope of the density of one feature to the slope of the density of another feature, a ratio of a maximum density of one feature to the maximum density of another feature, a ratio of a minimum density of a feature to the minimum density of the same feature, a directionality of the density ratios, e.g., a density ratio between features facing one way or direction and features facing in an opposite direction (for example, the radiodensity ratio of features facing inwards towards the myocardium and features facing outwards toward the pericardium), or a ratio of the minimum density of a feature to the maximum density of another feature. Such determined information may indicate distinct differences in risks of plaque in a patient. In some examples, determined information (for example as listed above) may be used with a percentage diameter of stenosis to determine characteristics of a patient's arteries. Additional information regarding examples of analysis of the attenuation patterns in the coronary lumen attenuation patterns of plaque, and attenuation patterns of fat are described in reference to FIGS. 9-12.

Still referring to FIG. 6, in an example of the directionality of radiodensity ratios, the density of a portion of the necrotic core plaque 615 to the density of a portion of the vessel 665 (e.g., plaque:vessel inward facing ratio) can be determined and may indicate a certain risk of plaque. In another example of the directionality of radiodensity ratios, the density of a portion of a portion of the vessel 665 to the density of the necrotic core plaque 615 (e.g., vessel:plaque outward facing) can be determined and may indicate a certain risk of plaque. In another example, the density ratio of the necrotic core plaque 615 to the density of a portion of the vessel 665 (e.g., plaque:vessel inward facing ratio) can be compared to the density ratio of the necrotic core plaque 615 to the fibrous plaque 620 (e.g., plaque:plaque outward facing) may indicate a certain risk of plaque. In other examples, features that are adjacently positioned can be used to determine inward and/or outward directional radiodensity values that may be used to indicate a risk associated with plaque. Such ratios may provide distinct differences in risk of plaque. Various embodiments of directional radiodensity values and/or directional radiodensity ratios can be included with any of the other information described herein to indicates plaque risk.

The size of a compartment may be used to also indicate a risk associated with plaque. For example, determination of risk associated with a plaque may be based at least partially on the size of the compartments, such that the ratio of the of the radiodensities affects the determination of risk and the function of the size of the compartments can also affect the determination of risk. While the presence of plaque in a patient where the ratio of plaque:fat may indicate a high risk plaque, if there is only a small amount of plaque (e.g., a small compartment of plaque), it would be of risk than if there was a larger compartment of the same plaque with the same radiodensity ratio of plaque to fat. In one implementation, the size (e.g., a volume) of the compartment a feature (e.g., of lumen, plaque, perivascular tissue (fat), and myocardium) can be determined, and a radiodensity ratio can also be determined, and then the ratio can be weighted based on the size of the compartment. For example, a large compartment can increase the weight of a ratio to make the ratio more indicative of a risk associated with the plaque. Similarly, a small compartment can decrease the weight of a ratio to make the ratio less indicative of a risk associated with the plaque. In an implementation, only the compartment size of the plaque is used to weight (or adjust) the ratio.

In an implementation, the compartment size of both of the features that are used in the radiodensity ratio can be used to weight the ratio to determine a resulting risk. In an implementation, the compartment size of one of plaque, lumen, perivascular tissue, or myocardium is used to weight (or adjust) the risk associated with the radiodensity ratio. In an implementation, the compartment size of more than one of plaque, lumen, perivascular tissue, or myocardium is used to weight the risk associated with the radiodensity ratio. Various embodiments of determining plaque risk using compartment size can be included with any of the other information described herein to indicate plaque risk. Using a compartment size to weight other information, or otherwise adjust a risk associated with the radiodensity ratio, can be done in the examples as described in reference to FIGS. 7-12 and 16-19.

Figure 7:
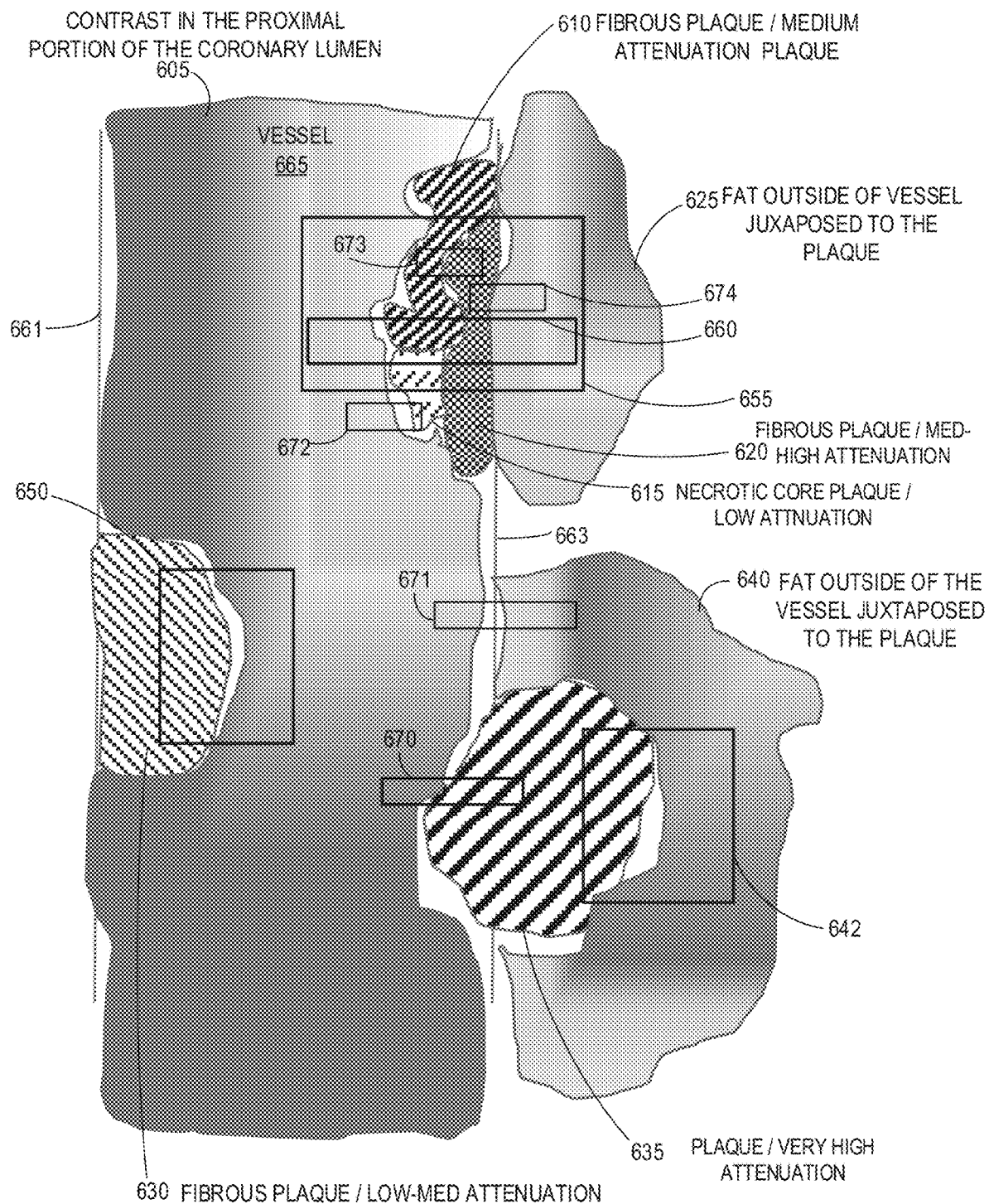
FIG. 7 illustrates the same vessel 665 and features of plaque and fat as illustrated in FIG. 6 and further illustrates additional examples of areas of an artery, and the plaque and/or perivascular fat that is near an artery, that may be analyzed to determine characteristics of a patient's arteries

FIG. 7 illustrates the same vessel 665 and features of plaque and fat as illustrated in FIG. 6 and further illustrates additional examples of areas of an artery, and plaque and/or perivascular fat near the artery, that may be analyzed to determine characteristics of a patient's arteries. Such areas are indicated in FIG. 7 by rectangular boxes, similar to the illustrations in FIG. 6. Although particular locations of the rectangular boxes are illustrated in FIG. 6 and FIG. 7, these are only examples of areas that may be analyzed. In one example, FIG. 7 illustrates box 660 which includes a portion of the vessel 665, a portion of necrotic core plaque 615, a portion of fibrous plaque 610, a portion of plaque 620, and a portion of fat 625. In another example, FIG. 7 illustrates box 655 which includes a portion of the vessel 665, a portion of the fibers plaque 610 a portion of the plaque 620 the portion of the necrotic core plaque 615, and a portion of fat 625. Box 655 may, in some cases, illustrate the general area for analysis due to the existence of 3 different types of plaque 610, 615, 620, and adjacently disposed fat 625. Particular portions of a general area for analysis may be analyzed to better understand the characteristics formed by adjacent features. For example, FIG. 7 illustrates the general area 665 containing box 660 (described above), box 673, which extends across a portion of fibrous plaque 610 and plaque 620, and box 674 which extends across a portion of plaque 620 and perivascular fat 625. As another example, FIG. 7 also illustrates another box 672 that extends across a portion of the vessel 655 and necrotic core plaque 615. As a further example, FIG. 7 illustrates box 671 that extends across a portion of the vessel 665 and fat 640 juxtaposed to the vessel 665. As a further example, FIG. 7 illustrates box 670 that extends across a portion of the vessel 665 and plaque 635. Characteristics of a patient's arteries that can be analyzed based on these features can include:

1. A ratio of lumen attenuation to plaque attenuation, wherein the volumetric model of scan-specific attenuation density gradients within the lumen adjusts for reduced luminal density across plaque lesions that are more functionally significant in terms of risk value
2. A ratio of plaque attenuation to fat attenuation, wherein plaques with high radiodensities are considered to present a lower risk, even within a subset of plaques considered "calcified," where there can be a gradation of densities (for example, 130 to 4000 HU) and risk is considered to be reduced as density increases.
3. A ratio of lumen attenuation/plaque attenuation/fat attenuation
4. A ratio of #1-3 as a function of 3D shape of atherosclerosis, which can include a 3D texture analysis of the plaque 5. The 3D volumetric shape and path of the lumen along with its attenuation density from the beginning to the end of the lumen.
6. The totality of plaque and plaque types before and after any given plaque to further inform its risk.
7. Determination of "higher plaque risks" by "subtracting" calcified (high-density) plaques to obtain a better absolute measure of high risk plaques (lower-density plaques). In other words, this particular embodiment involves identifying calcified plaque and excluding it from further analysis of plaque for the purpose of identifying high risk plaques.

Figure 8:
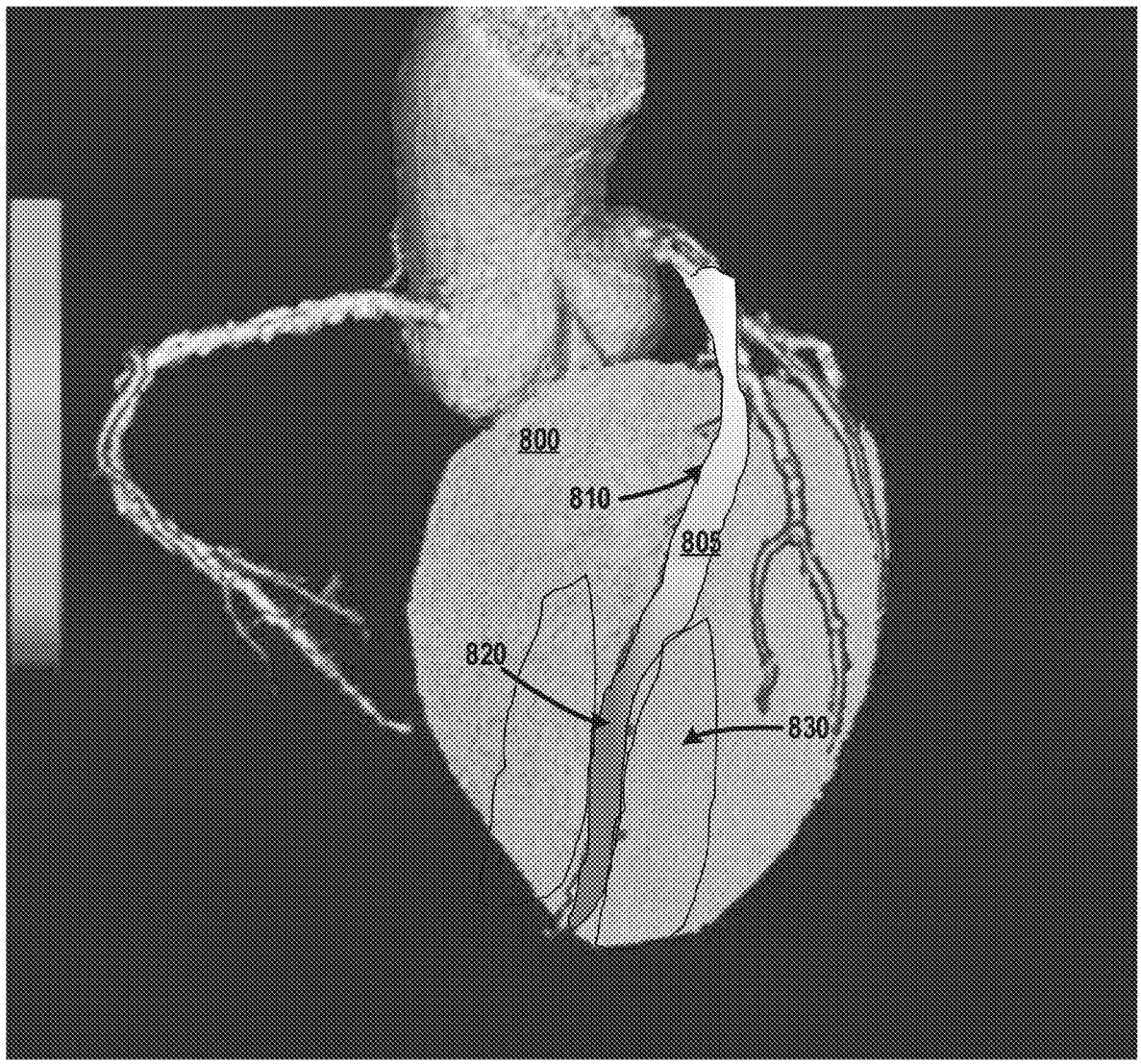
FIG. 8 illustrates examples of regions that may be evaluated to characterize plaque, the regions including a portion of a coronary artery and perivascular tissue disposed adjacent to the coronary artery.

FIG. 8 illustrates an example of an image of a heart 800 and certain regions of a coronary artery 805. In this example, at region 810, contrast attenuation in the proximal portion of the vessel is high. At region 820, contrast attenuation in the distal portion of the vessel is low. At region 830, contrast attenuation in the heart muscle is low, that is, in that region of the heart muscle that is close to the distal portion of the vessel. The radiodensity values in these regions may be determined and compared. In some examples a ratio of the radiodensity values of regions 830 and 820 (i.e., radiodensity values 830:radiodensity values 820) and/or the radiodensity values of regions 830 and 810 (i.e., radiodensity values 830:radiodensity values 810) can be used to determine whether there is ischemia or not.

Figure 9:
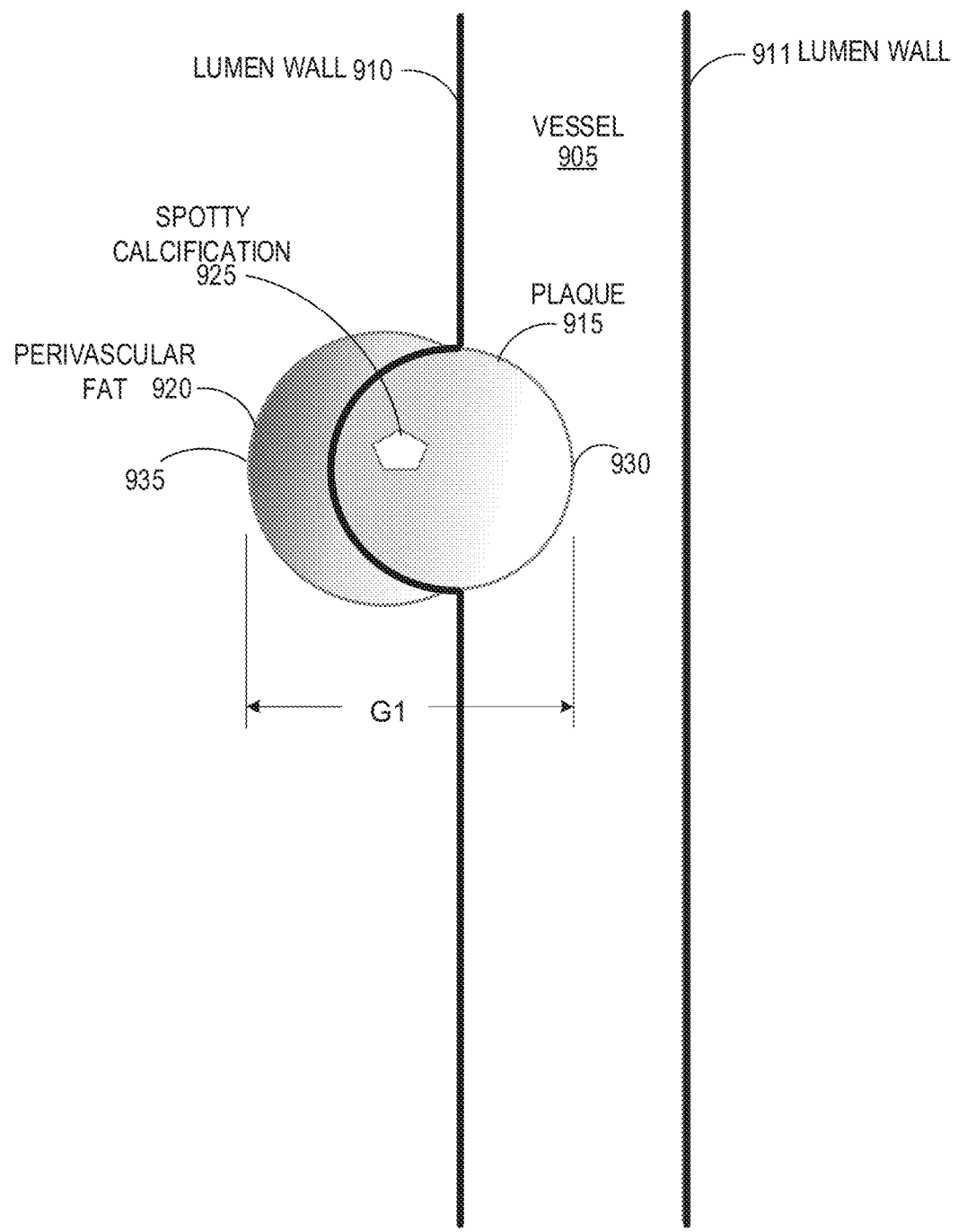
FIG. 9 illustrates an example of an overview of a representation of image data of a coronary artery (vessel) 905.

FIG. 9 illustrates an example of an overview of a representation of image data of a coronary artery (vessel) 905. In this example, vessel 905 includes a lumen walls 910, 911 (the lines indicating the outer boundary of the lumen wall), and plaque 915 which is within the vessel 905, that is, plaque 915 is within lumen wall 910, and extends outward away from the center of the vessel 905 as well as extending inward towards the center of the vessel 905. FIG. 9 also illustrates perivascular fat 920 that is disposed adjacent to plaque 915 and outside of the vessel 905. That is, lumen wall 910 is between perivascular fat 920 and plaque 915. Both the plaque 915 in the perivascular fat dietary 920 include contrast attenuation patterns that may be analyzed to determine characteristics of the coronary artery 905. FIG. 9 also includes spotty calcification 925 located in plaque 915. In this example, G1 represents a portion of the perivascular fat 920 and the plaque 915, from the inner surface 930 of the plaque 915 to the outer surface 935 of the perivascular fat 920, where the gradient the gradient of the density of the contrast attenuation may be determined and evaluated, described in more detail in FIG. 10.

Figure 10:
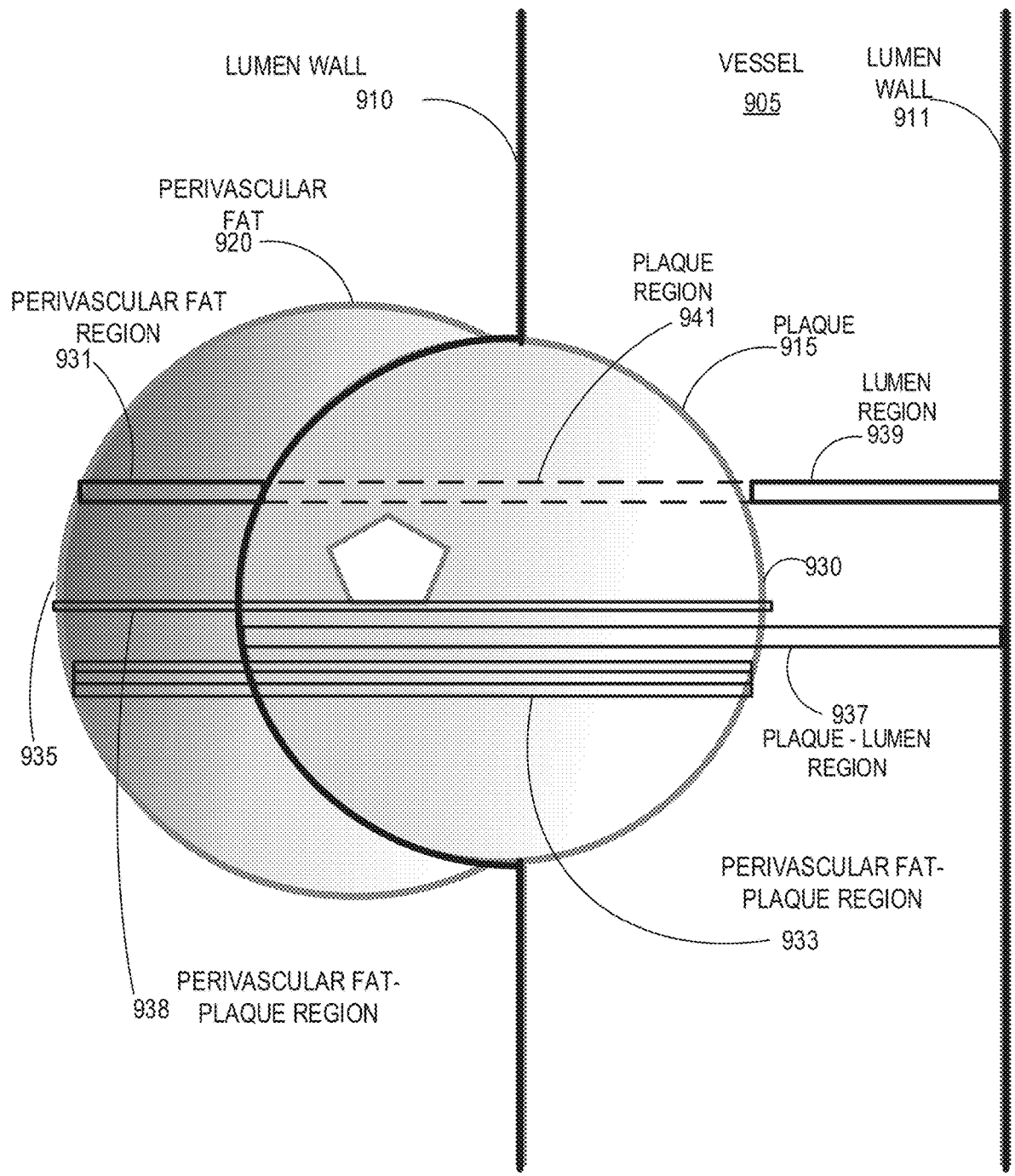
FIG. 10 illustrates another view of the representation of image data of the coronary artery (vessel) 905 illustrated in FIG. 9, showing examples of certain features of plaque, perivascular tissue (e.g., fat) and lumen that can be evaluated to characterize coronary plaque determine health characteristics of a patient's arteries.

FIG. 10 illustrates another view of the representation of image data of the coronary artery (vessel) 905 illustrated in FIG. 9, showing examples of certain features of plaque, perivascular tissue (e.g., fat) and lumen that can be evaluated to characterize coronary plaque determine health characteristics of a patient's arteries. Plaque 915 and perivascular fat 920 that were shown in FIG. 9 are also shown in FIG. 10. The image data in FIG. 10 demonstrates a gradient the transitions from lighter density values to darker density values along a line in the image data that extends from an edge of the plaque 915, that is closest to the center of the vessel 905, to the edge 935 of the perivascular fat 920.

The density of portions of the image data depicting the perivascular fat 920, plaque 915, and/or the lumen of the vessel 905 may be evaluated to characterize coronary plaque into determine health characteristics of a patient's arteries. As mentioned above, information determined by analyzing various aspects of the density of the lumen, the plaque, and/or the perivascular fat can include, but is not limited to, one or more of a slope/gradient of a feature, a maximum density, minimum density, a ratio of a slope of one feature to the slope of another feature, a ratio of a maximum density of one feature to the maximum density of another feature, a ratio of a minimum density of a feature to the minimum density of the same feature, or a ratio of the minimum density of a feature to the maximum density of another feature. Any of this information can be combined with other information to determine characteristics of a patient's arteries.

FIG. 10 illustrates several examples of regions of features in image data that may be evaluated, other regions of evaluation may also be selected in other examples. A first example is a region 931 of perivascular fat 920 delineated by a rectangular box indicating perivascular fat 920. Region 931 extends from an edge of the perivascular fat region 920 to the plaque 915, and the image data evaluated may be in one or more dimensions (for example two dimensions). Another example is a region 941 that extends across plaque 915. Region 941 is adjacent to the perivascular fat region 931 on one side, and adjacent to lumen region 939 on the opposite side. Lumen region 939 extends from plaque 915 across a portion of the vessel 905. In this configuration, perivascular fat region 931, plaque region 941, and lumen region 939, are aligned and span the lumen of the vessel 905, the plaque 915, and the perivascular fat region 920. The densities of the image data in a portion of, or all of, these regions may be evaluated relating to their maximum density, minimum density, gradient, or ratio of one of these characteristics, as described herein.

In another example, plaque—lumen region 937 is delineated by rectangular box that extends from the lumen wall 911 across the vessel 905 and across the plaque 915. Plaque—lumen region 937 represents a two dimensional set densities of image data that all, or portion of, may be evaluated.

In another example, as illustrated in FIG. 10, perivascular fat—plaque region 933 is an evaluation region delineated by retainer boxes that extends from the edge 930 of the plaque 915 to the edge 935 of the perivascular fat 920. This example illustrates that in some cases, two or more adjacent vectors (or "lines") of image data across features in the image data that may include one or more features (e.g., fat, plaque, lumen) may be evaluated. Evaluation of two or more adjacent vectors of image data may result in more robust metrics that are less affected by noise in the image data.

In another example, perivascular fat—plaque region 938 is delineated by a rectangular box that extends from the edge 930 of the plaque 915, that extends into the vessel 905, to the edge 935 of the perivascular fat 920 disposed distal to the plaque 915. Perivascular fat—plaque region 938 represents a one dimensional set of densities of image data that all, or a portion of, may be evaluated. As an example of metrics of the features depicted in FIG. 10 (using mere examples of radiodensity values), the slope of the gradient of the image density values in the plaque 915 in the perivascular fat—plaque region 938 may be −3, the maximum density of the plaque 915 may be 98 and the minimum density of the plaque 915 may be −100. The slope of the gradient of the perivascular fat 920 and the perivascular fat—plaque region 938 may be −5, the maximum density of the perivascular fat 920 in the perivascular fat—plaque region 938 may be 180, and a minimum density of the perivascular fat 920 in the perivascular fat—plaque region 938 may be 102. Other metrics of the perivascular fat—plaque region 938 may include: a ratio of the slopes of the plaque 915 to the perivascular fat 920 {−3/−5}, a ratio of the maximum density of the plaque 915 to the maximum density of the perivascular fat 920 {98/180}; a ratio of the minimum density of the plaque 915 to the minimum density of the perivascular fat 920 {−100/102}; a ratio of the minimum density of the plaque 915 to the maximum density of the perivascular fat 920 {−100/180}; a ratio of the maximum density of the plaque 915 and the minimum density of the perivascular fat 920 {98/102}; and the gradient across the entire perivascular fat—plaque region 938 (e.g., −4).

Figure 11:
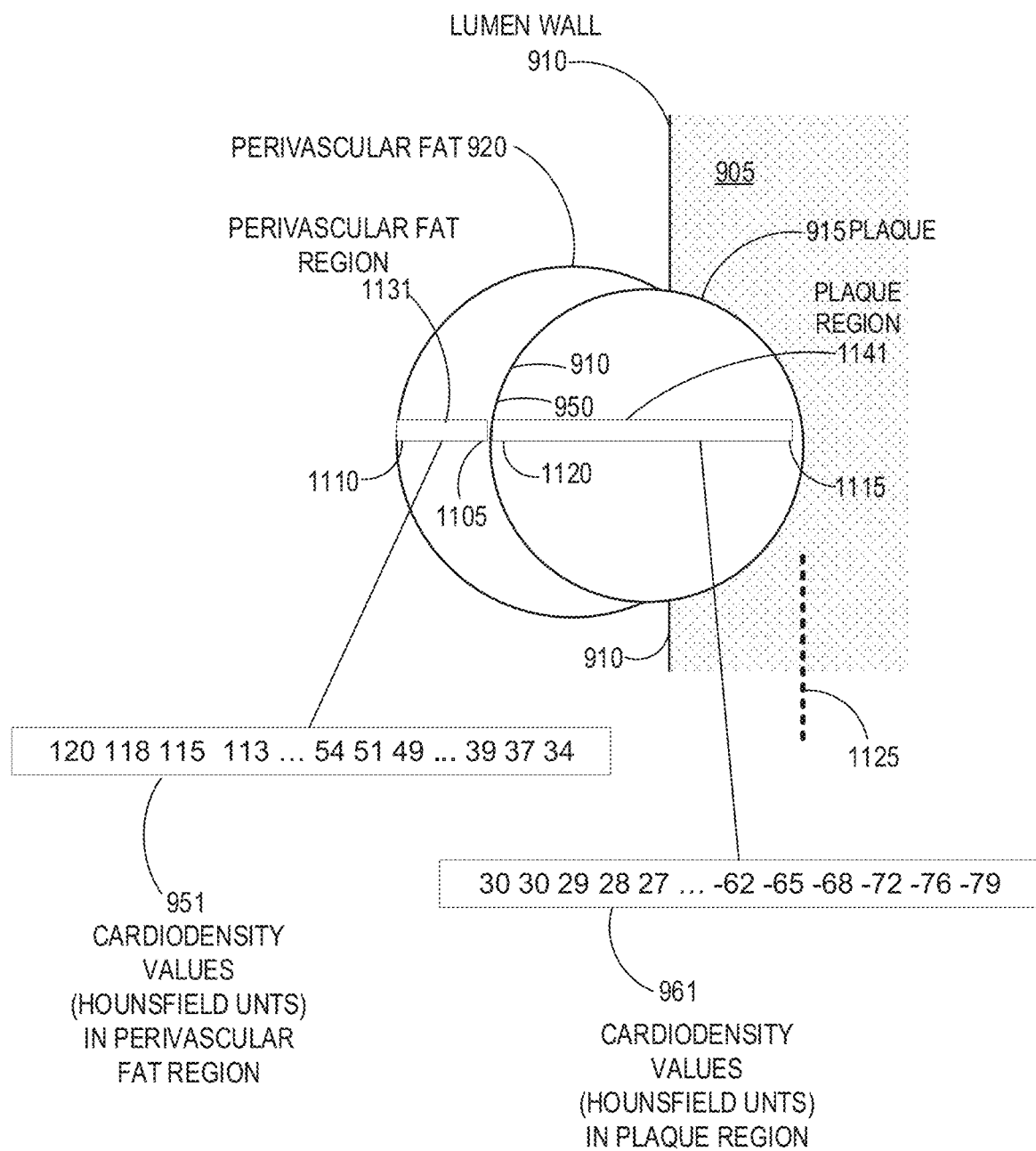
FIG. 11 illustrates another example of determining radiodensity values of regions of the perivascular fat and plaque to determine metrics, as described herein.

FIG. 11 illustrates another example of determining radiodensity values of regions of the perivascular fat and plaque to determine metrics, as described herein. FIG. 11 shows coronary artery 905, coronary plaque 915 located in a lumen wall 910 of the coronary artery 905, and perivascular fat 920 located outside of the lumen wall 910 and adjacent to the coronary plaque 915, similarly as shown in FIG. 10.

FIG. 11 further illustrates an example of two regions where radiodensity data that may be evaluated to characterize the plaque. The two regions include a first region (or a perivascular fat 1131 region) in the perivascular fat 920 and a second region (or a plaque region) 1141, adjacent to the first region 1131 and in the coronary plaque 915. In this example, the coronary artery 905 and the lumen wall 910 are depicted as being aligned generally vertically on the page. The plaque 915 and the fat 920 are illustrated as extending laterally from the artery 905 (e.g., to the left relative to the figure orientation). The plaque 915 is within the lumen wall 910 of the artery 905, such that the lateral extent of the lumen wall 910 is shown as coincident with the leftmost boundary 950 of the plaque 915. Dashed line 1125 indicates the alignment of the coronary artery 905 at this location, and in this example indicates a center line of the artery 905 which is aligned with the artery 905 at this location.

As illustrated in FIG. 11, the fat region 1131 and the plaque region 1141 represent areas of radiodensity information (e.g., 3D or 2D) of image data, generated from one or more images, that are evaluated to characterize plaque 915. As described above, in some examples, one or more images can be used to generate a 3D data set that represents a coronary artery, plaque in the artery, and perivascular tissue that is located near or adjacent to the artery and/or the plaque. Once a data set is generated, it can be used to characterize the relationship between one or more of plaque, perivascular tissue and lumen tissue. In some embodiments of evaluating plaque, the data set is used as a 3D data set (which may also be referred to as a 3D model). In some embodiments of evaluating plaque, the data set is used as a 2D data set where information in the data set is looked at in XY (2D) region. In the example illustrated in FIG. 12, the image data can present 2D or 3D data.

In some embodiments of evaluating plaque, a region of radiodensity values can be used that are along a line in the image data, whether the data evaluated is a 2D or 3D representation of an artery. A region radiodensity values along a line can be referred to as a "linear region." The linear region may indicate data that includes, or goes across, part or all of one or more types of tissues, for example, plaque, perivascular tissue, and/or lumen tissue of the coronary artery. That is, the region may be referred to as indicating a portion of one or more type of tissue (e.g., plaque, perivascular tissue, and/or lumen tissue of the coronary artery) which indicates that some information in the data set is included in the particular region. The radiodensity data in a linear region is a vector with dimensions 1×n, where n represents the number of discrete points of radiodensity data along the vector. Some examples of regions which may be linear regions are illustrated and described in FIG. 10. For example, lumen region 939 (FIG. 10) which includes part of the vessel 905 tissue, coronary plaque region 941 which includes a portion of the coronary plaque 915, perivascular fat region 931 which includes a portion of the perivascular fat 920, perivascular fat-plaque region 935 which includes a portion of the perivascular fat 920 and the plaque 915, and plaque-lumen region 937 which includes a portion of the plaque 915 and the lumen of the vessel 905.

In the example illustrated in FIG. 11, the plaque region 1141 delineates a portion of the plaque 915 and extends in a lateral (or substantially lateral) direction relative to the alignment of the coronary artery as indicated by centerline 1125 of the vessel 905. The plaque region 1141 extends from a proximal end 1115 that is closest to the center of the artery 905, to a distal end 1120 that extends laterally away from the center line 1125 of the artery 905. The perivascular fat region 931 extends from a proximal end 1105 that is closer to the artery 905 to a distal end 1110, farthest from the artery 905. Also shown in FIG. 11, the perivascular fat region 1131 is aligned (or substantially aligned) with the plaque region 1141. The proximal end 1105 of the perivascular fat region 1131 is near, or adjacent to, the distal end 1120 of the plaque region 1141.

Radiodensity data in the perivascular fat region 931 is represented by radiodensity values 951. Radiodensity data in the plaque region 941 is represented by radiodensity values 961. These radiodensity values 951, 961 may be in Hounsfield Units, described above. Once the regions 1131, 1141 are determined, and the radiodensity values in the regions are determined, the radiodensity values 951 representing the density of a portion the perivascular fat 920 and the radiodensity values 961 representing the radiodensity values of a portion of the plaque 915 may be analyzed to determine characterizations of the plaque and help assess its risk.

Analysis of the radiodensity values of each linear region can be performed to determine metrics that indicate the radiodensity values in a region, or the relationship of the cardio density values in one region as compared to another region. The plaque can be characterized by analyzing metrics that are determined by one or more of the maximum density, minimum density, and/or the slope of the gradients (sometimes referred to simply as "slope" for ease of reference) for a region or several regions, for example, adjacent regions. In some examples, determining metrics can include determining one or more of a maximum density of the radiodensity values, a minimum density of the radiodensity values, and/or a slope of the gradient of the radiodensity values., one or more of a slope/gradient of a feature, a maximum density, minimum density, a ratio of a slope of one feature to the slope of another feature, a ratio of a maximum density of one feature to the maximum density of another feature, a ratio of a minimum density of a feature to the minimum density of the same feature, or a ratio of the minimum density of a feature to the maximum density of another feature.

In one particular example, referring to FIG. 11, the plaque 915 may be characterized by analyzing one of more of the maximum density, minimum density, and slope of the radiodensity values in the perivascular fat region 1131 and the adjacent plaque regions 1141. For example, in the illustrated examples of radiodensity values in regions 1131, 1141, the maximum and minimum density of the perivascular fat 920 is 120 and 34, respectively, and the maximum and minimum density of the plaque 915 is 30 and −79 respectively. The gradient of the radiodensity values in plaque region 1141 is −2. The gradient the cardio density values in perivascular fat region 1131 is −3. The determined metrics may include, for example:

(a) a ratio of the gradient of the perivascular fat region 1131 and the gradient of the plaque region 1141: {−2:−3};

(b) a ratio of the maximum density of the perivascular fat region 1131 and the maximum density of the plaque region 1141: {120:30};

(c) a ratio of the minimum density of the perivascular fat region 1131 and the minimum density of the plaque region 1141: {34:−79};

(d) a ratio of the minimum density of the perivascular fat region 1131 and the maximum density of the plaque region 1141: {34:30};

(e) a ratio of the maximum density of the perivascular fat region 1131 and the minimum density of the plaque region 1141: {120:−79}; and (f) the gradient from the proximal end 1115 of the plaque region 1141 (e.g., the inner surface of the plaque 915) to the distal end 1110 of the perivascular fat region 1131 (e.g., the outer surface of the perivascular fat 920): −2.

A maximum or a minimum density of the radiodensity values in a regions may be determined several ways, according to various embodiments. In one example, simply the maximum/minimum radiodensity value can be selected as the maximum or minimum value. However, some data sets may include outliers that indicate erroneous data. If it can be determined that an outlying radiodensity value is in fact erroneous (e.g., using statistical methods), then the outlying value may be deleted from the analysis, or corrected if possible. Outliers may be due to random variation or may indicate something scientifically interesting. In any event, we typically do not want to simply delete the outlying observation. However, if the data contains significant outliers, robust statistical techniques or alternatively, imaging techniques, can be used to filter the image data to improve the accuracy of the metrics.

Figure 12:
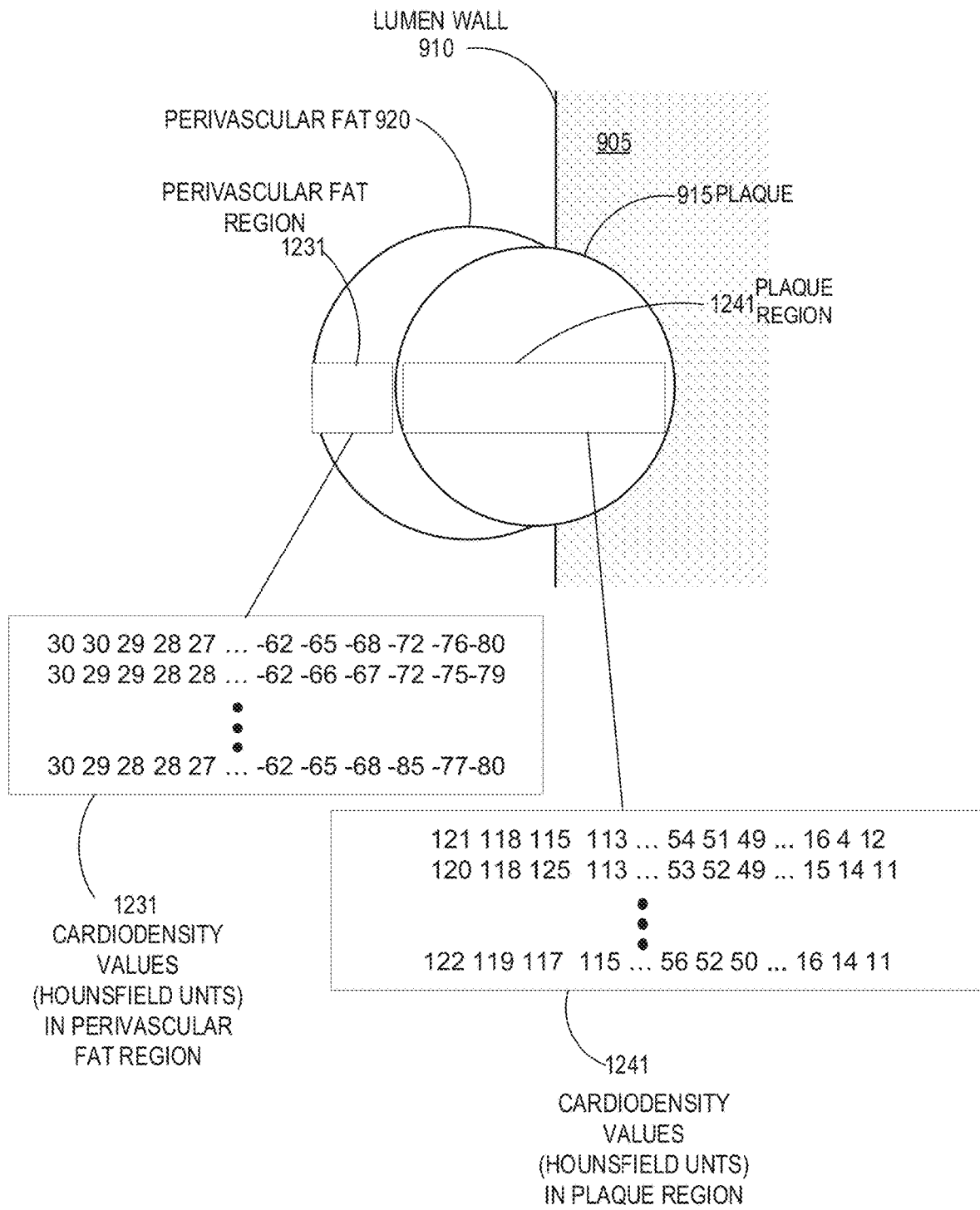
FIG. 12 illustrates a representation of image data showing a coronary artery 905, plaque 915, and perivascular fat 920 located adjacent to the plaque (as similarly shown in FIG. 11).

FIG. 12 illustrates a representation of image data showing a coronary artery 905, plaque 915, and perivascular fat 920 located adjacent to the plaque (as similarly shown in FIG. 11). FIG. 12 also illustrates a perivascular fat region 1231 and the perivascular fat 920, and a plaque region 1241 in the plaque 915. The perivascular fat region and 1231 and the plaque region 1241 differ from the fat region 1131 and the plaque region 1141 illustrated in FIG. 11 in that the radiodensity values in these regions are in the form of a two dimensional vector. That is, if each of the regions 1231, 1241 contains rows (e.g., lateral with reference to the page) and columns (e.g., vertical with reference to the page) of cardio representing the image data in regions 1231, 1241, density values in regions 1231, 1241 includes two or more adjacent rows of radiodensity values. In one example, the two or more adjacent rows of radiodensity values may be used to generate minimum and maximum density values, for example, by taking the maximum and minimum density value from any of the two or more rows. In another example, the two or more adjacent rows of radiodensity values may be used to generate minimum and maximum density values by averaging the information in the two or more rows, for example, by averaging the maximum radiodensity values in each of the rows to determine a maximum radiodensity value for the region, and by averaging the minimum radiodensity values in each of the rows to determine a minimum cardio density value for the region. Similarly, the gradient of the radiodensity values in each of the regions may be calculated based on the radiodensity values in two or more rows. For example the gradient of the radiodensity value in each row of the region may be calculated, and the gradient can be determined by averaging each of the calculated gradient values. It is contemplated to use other statistical techniques to average multiple radiodensity values in a region to determine characteristics and metrics of the region. Such techniques may be particularly useful to minimize the effect of noise (inaccurate data) in a region.

FIG. 13 is a table 1300 illustrating an example of a set of patient information. In this example, the table 1300 includes two columns, a first column 1305 labeled "Item" and a second column 1310 labeled "Importance or Value."

In this example, the items of patient information in the first column 1305 includes information of a patient's sex, age, BMI, medication, blood pressure, heart rate, weight, height, race, body habitus, smoking, diabetes, hypertension, prior CAD, family history, and labs. In other examples, more or fewer items may be included, and/or different items may be included.

The second column 1310 can include a numeric assessment of the importance or value of each item in the first column 1305. The numeric assessment can be provided by a risk score and used to bias the analysis based on one or items that are deemed to be more important. In some examples, each item has the same assigned value. In other examples, different values can be assigned to one or more of the items. In some example, the values can be normalized to add up to 1.0, or 100%, or another value.

FIG. 14 is a table 1400 illustrating an example of a set of scan information. The table 1400 includes a first column 1405 labeled "Item" listing scan related items, and a second column 1410 labeled "Importance or Value." In this example, the items of scan information in the first column 1405 includes contrast to noise ratio, signal-to-noise ratio, tube current, tube voltage, contrast type, contrast volume, flow rate, flow duration, slice thickness, slice spacing, pitch, vasodilator, beta blockers, recon option whether it's iterative or filter back projection, recon type whether it's standard or high resolution, display field-of-view, rotation speed, gating whether it's perspective triggering or retrospective gating, stents, heart rate, or blood pressure. In other examples, more or fewer items may be included, and/or different items may be included.

The second column 1410 can include a numeric assessment of the importance or value of each item in the first column 1405. The numeric assessment can be provided by a risk score and used to bias the analysis based on one or items that are deemed to be more important. In some examples, each item has the same assigned value. In other examples, different values can be assigned to one or more of the items. In some example, the values can be normalized to add up to 1.0, or 100%, or another value.

FIG. 15 is a table 1500 illustrating an example of a set of cardiac information. The table 1500 includes a first column 1505 labeled "Item" listing scan related items, and a second column 1510 labeled "Importance or Value." In this example, the items of cardiac information in the first column 1504 includes contrast to density, volume, geometry—shape, location, remodeling, baseline anatomy (for diameter, length), compartments (inner, outer, within), stenosis (diameter, area), myocardial mass, plaque volume, plaque composition, texture, or uniformity. In other examples, more or fewer items may be included, and/or different items may be included.

The second column 1510 can include a numeric assessment of the importance or value of each item in the first column 1505. The numeric assessment can be provided by a risk score and used to bias the analysis based on one or items that are deemed to be more important. In some examples, each item has the same assigned value. In other examples, different values can be assigned to one or more of the items. In some examples, the values can be normalized to add up to 1.0, or 100%, or another value.

Figure 16:
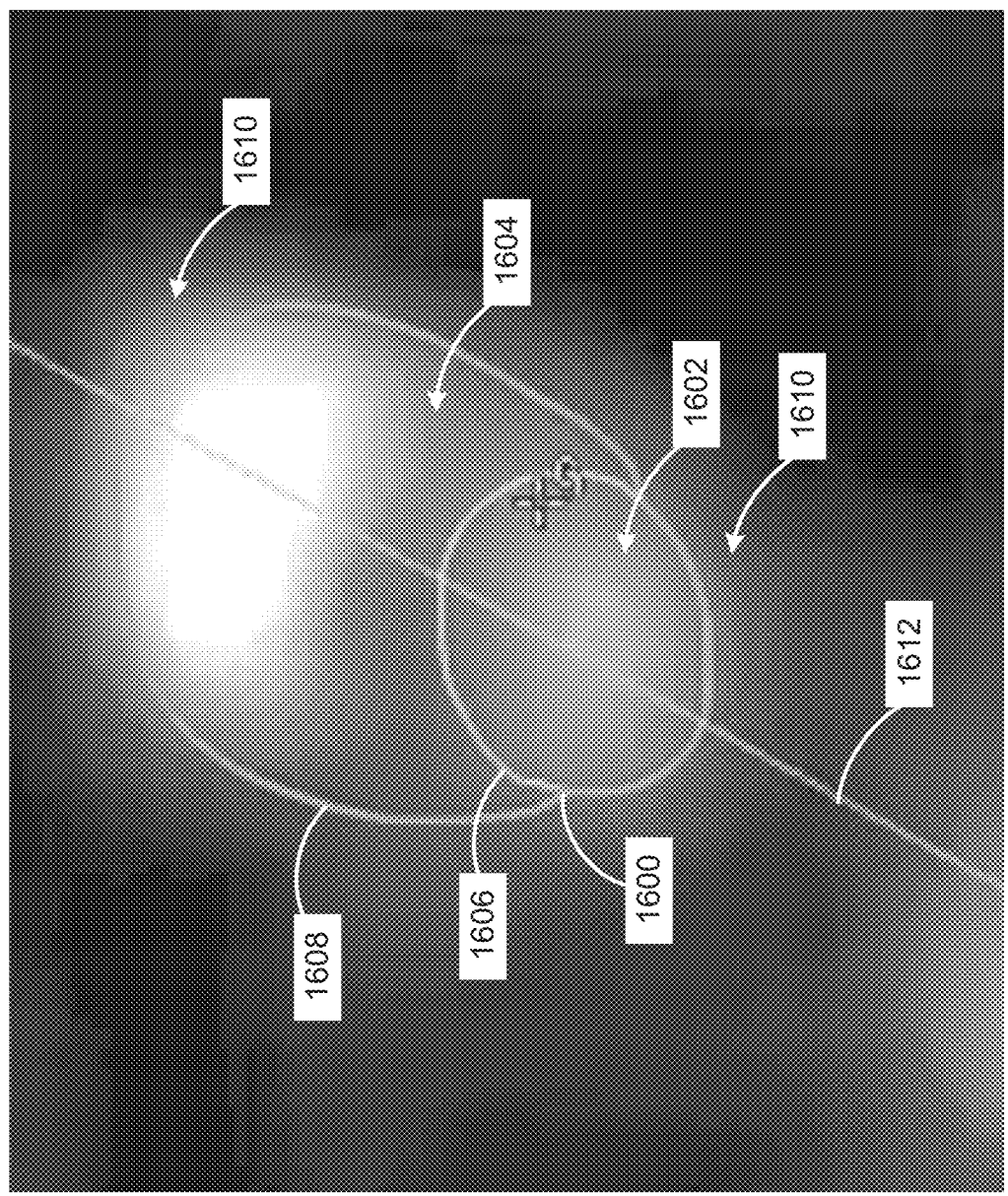
FIG. 16 is an example of a cross section of a coronary artery 1600. The coronary artery includes an inside lumen of the artery and an outer vessel wall with gradient radiodensities exhibited in the lumen, within the plaque and perivascular tissue outside of the vessel.

FIG. 16 is an example of a cross section of a coronary artery 1600. In FIG. 16 illustrates the inside lumen wall 1606 of the artery 1600 having an interior portion 1602 and the outer vessel wall 1608 with gradient radiodensities exhibited in the lumen within the plaque 1604 between the lumen wall 1606 and perivascular tissue 1620 outside of the vessel. The line 1612 indicates a line through a diameter of the artery 1600.

Figure 17:
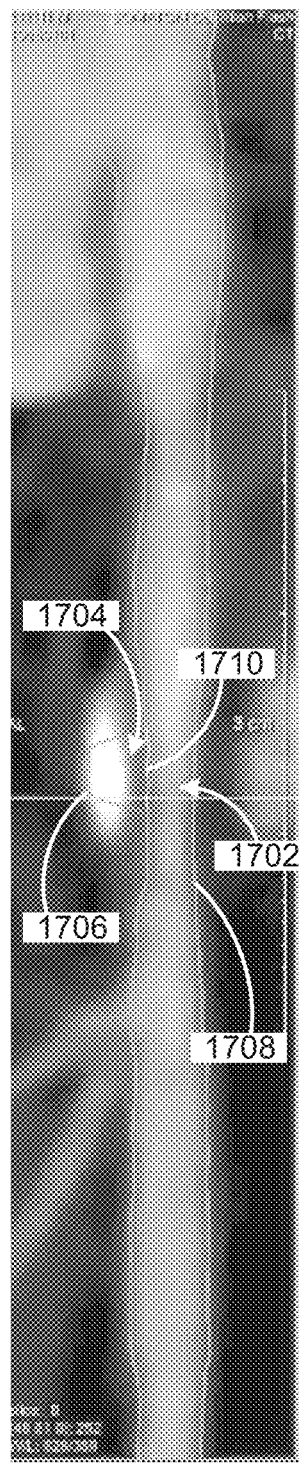
FIG. 17 is an image showing an example of a longitudinal straightened rendering of a coronary artery 1708 that shows a buildup of plaque between an inner portion and an outer portion of the coronary artery 1708. This figure demonstrates the different compartments of lumen, plaque and perivascular tissue.

FIG. 17 is an image showing an example of a longitudinal straightened rendering of a coronary artery 1708 that shows a buildup of plaque between an inner portion and an outer portion of the coronary artery 1708. As illustrated in FIG. 17, the coronary artery 1708 includes an inner lumen 1710 having a cavity 1702 within the inner lumen 1710 for transporting blood. The coronary artery 1708 also includes an outer vessel 1706 extending from the left side (relative to the orientation of FIG. 17) of the coronary artery 1708. Plaque 1704 buildup is between the outer vessel 1706 and the inner lumen 1710. This figure demonstrates the different compartments of the lumen, the plaque and perivascular tissue outside of the inner lumen 1710 and plaque 1702.

Figure 18:
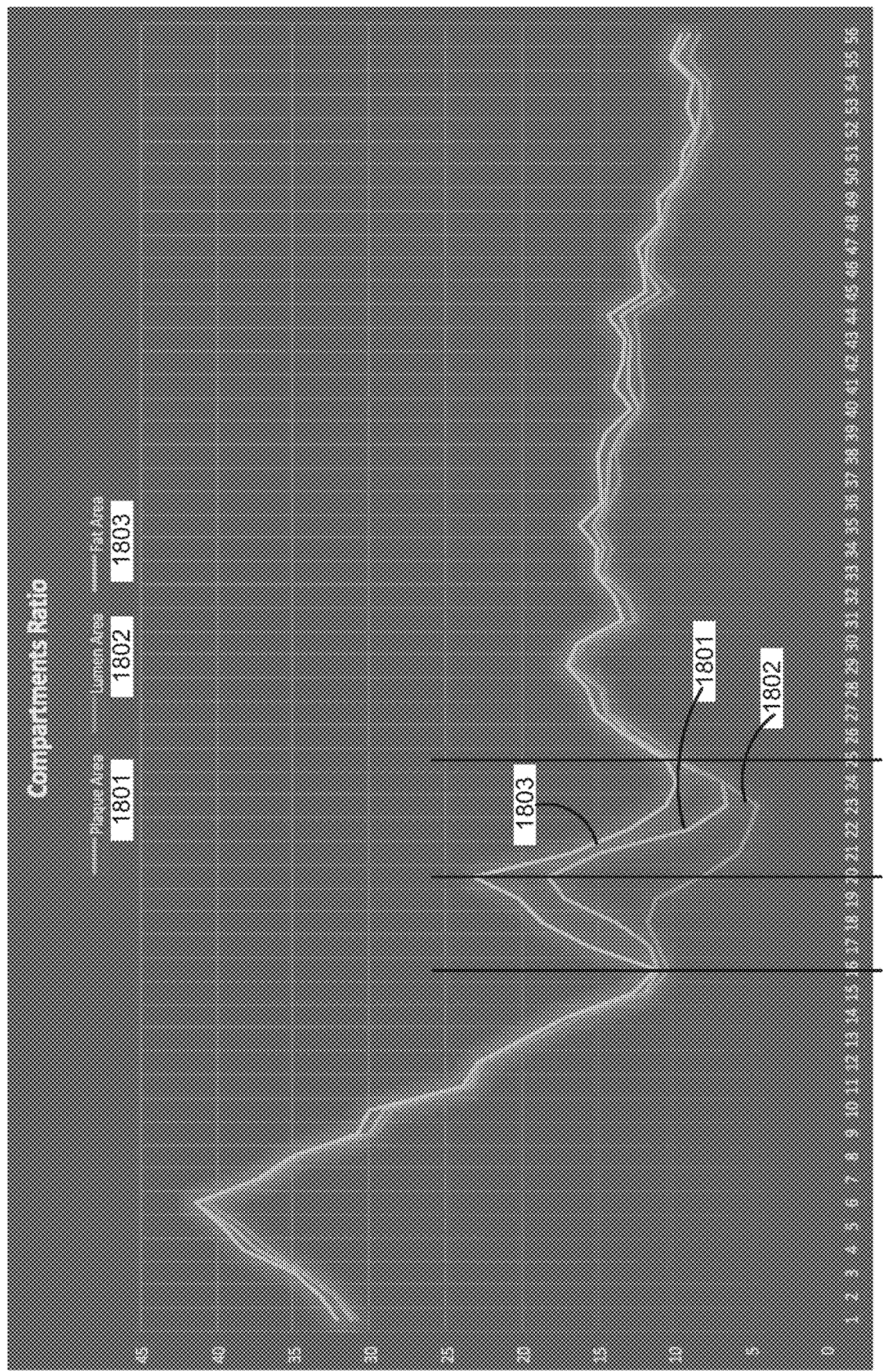
FIG. 18 is a chart of plots illustrating the compartment areas of cross-sections of plaque 1801, lumen 1802, and fat 1803 along the length of a coronary artery. Different ratios of these compartments can be calculated by area or by summated volume.

FIG. 18 is a chart of plots illustrating the compartment areas of cross-sections of plaque 1801, lumen 1802, and fat 1803 along the length of a coronary artery. Such plots 1801, 1802, 1803 can be generated for the left and/or right coronary artery. A plurality of cross-sectional areas of plaque of a coronary artery can be determined along a length of the coronary artery. The distance from the ostium of each plaque, lumen, and fat cross-section can also be determined. The ratios of cross-sections of the plaque, lumen and fat at one or more portions of one or more coronary arteries may be indicative of a patient's risk associated with plaque. FIG. 18 illustrates an example of plots of the plaque cross-sections 1801, lumen cross-sections 1802, and fat cross-sections 1803, where the distance from the ostium of the plaque, lumen, and fat cross-sections 1801, 1802, 1803 are plotted on the x-axis, and area of the respective plaque, lumen, and fat cross-sections 1801, 1802, 1803 are plotted on the y-axis. In some embodiments, the distance scale along the x-axis can be in millimeters, although other scales can be used in other embodiments. In some embodiments, the areas of the cross-sections can be in $mm^2$, although another area unit of measurement can be used in other embodiments. Ratios of these compartments along portions of a coronary artery can be calculated based on one or more or the plaque cross-sections 1801, the lumen cross-sections 1802, and the fat cross-sections 1803 at one or more corresponding distances from the ostium, and the calculated ratios can be included in a generated display or in a report.

In the example illustrated in FIG. 18, along the entire distance from the ostium, the cross-sections of the lumen 1802 are generally smaller than the cross-sections of the plaque 1801 and the cross-sections of the fat 1803, and the cross-sections of the plaque 1 801 are smaller than the cross-sections of the lumen 1802. At some distances from the ostium (for example, from about distances 7 to 9 along the x-axis) one or more of the cross-sectional areas of the plaque, the lumen, and/or the fat are substantially similar, or nearly the same, although even in these areas the cross-sections of the lumen 1802 are smaller than the cross-sections of the plaque 1801, and the cross-sections of the plaque 1801 are smaller than the cross-sections of the fat 1803. However, at other distances from the ostium the cross-sections differ greatly and this difference is clearly visible from the plaque cross-section plot 1801, the lumen cross-section plot 1802, and the fat cross-section plot 1803. For example, in a section of the coronary from about the distance 16 (indicated by line "A") to about the distance 25 (indicated by line "B") along the x-axis, the cross-section area of the fat 1803 is visibly greater the cross-section of the plaque 1801, and the cross-section area of the plaque 1801 is visibly greater than the cross-section area of the lumen 1802. As a general example, at one specific distance "20" indicated by the line "C" the cross-sectional area of the lumen 1802 is about 9 units, the cross-sectional area of the plaque 1801 is about 18 $units^2$, and the cross-sectional area of the fat is about 24 $units^2$. As a specific example, at the specific distance 20 mm indicated by the line C, the cross-sectional area of the lumen 1802 is about 9 $mm^2$, the cross-sectional area of the plaque 1801 is about 18 $mm^2$, and the cross-sectional area of the fat is about 24 $mm^2$. Accordingly, at distance "20" the ratio of the fat:plaque=1.33, the ratio of the fat:lumen=2.67, and the ratio of the plaque:fat=2.00. In some embodiments, the ratios of one or more of fat:plaque, fat:lumen, and/or plaque:fat are calculated as a plurality of distances in this data can be provided on a display or in a report as numbers or in a plot of the ratios. In an example, ratios that exceed a certain threshold can be flagged for further investigation of the portion or the coronary artery that corresponds to where the ratio exceeds a certain threshold. In another example, ratios that exceed a certain threshold for a certain distance (portion of the coronary artery) can be flagged for further investigation of the corresponding portion of the coronary artery. Such compartmental ratios may be used to indicate distinct differences in risks associated with plaque.

Ratios of compartments of the plaque, lumen and fat along a coronary artery can also be calculated based on summated volume (e.g., based on the cross-sectional area of the plaque, lumen, and fat over a certain distance) and the summated volume can be included in a generated display or in a report. The ratios of compartments of the plaque, lumen and fat along a coronary artery calculated based on summated volume may be indicative of a patient's risk associated with plaque. In an example, a plurality of portions of the coronary artery can be used to calculate a plurality of summated volumes. In an example, for a point where a cross-section area ratio (e.g., fat:plaque, fat:lumen, and/or plaque:fat) is exceeds a certain threshold (or is above a certain threshold for a certain distance), this can mark a starting point to calculate the summated volume of the coronary artery. In an example, the point where cross-sectional area ratio (e.g., fat:plaque, fat:lumen, and/or plaque:fat) falls back below a certain threshold (or falls below a certain threshold for a certain distance) this can mark and ending point to calculate the summated volume of the coronary artery. An example using the plots in FIG. 18, at about line A one or more of the cross section area ratios (e.g., fat:plaque, fat:lumen, and/or plaque:fat) may exceed a certain threshold and thus line a can mark a starting point to calculate this made volume of the coronary artery; and then at about line B one or more of the cross section area ratios (e.g., fat:plaque, fat:lumen, and/or plaque:fat) may fall below a certain threshold and thus line B may mark the ending point to calculate this made volume of the coronary artery. Although the portion of the plots corresponding to distances 16-25 generally shows the largest ratios, in some examples smaller ratios may it may also indicate the beginning/ending of summated volume calculations. For example, beginning at a distance 34, the plots of the plaque cross-section 1801, lumen cross-section 1802, and fat cross-section 1803 vary consistently (although not greatly) to distance 46, and then again continue to vary consistently (although not greatly) to distance 56. In some examples, the summated volume may be determined to be calculated for a portion of the coronary artery when one or more of the cross section area ratios (e.g., fat:plaque, fat:lumen, and/or plaque:fat) such that they exceed a certain threshold for a certain distance, and the results flagged for further investigation of the corresponding part of the coronary artery either on a display or in a generated report. Such compartmental ratios may be used to indicate distinct differences in risks associated with plaque.

In some implementations, other compartmental ratios (e.g., fat:plaque, fat:lumen, and/or plaque:fat) may be calculated and provided on a display, or in a report, to provide additional information about a patient's coronary arteries. Such information may indicate a portion of an artery for further investigation, or may indicate a condition of a patient. One or more compartmental ratios may be determined at a first point in time (e.g., at a start date), and then determined again at a subsequent (second) point in time (e.g., 2 months later, 6 months later, 1 year later, 2 years later, and the like) to track any changes that occur in the patient over the theme period. The period of time can be, for example, from 1 week or two weeks, to months or years. In an example, one or more compartmental ratios may be determined at a first point in time (e.g., when a patient is 50 years old), and then determined again that a second point in time (e.g., when a patient is 60 years old) to track any changes that occur in the patient over a certain time period. In an example, for a patient that has a family history of coronary artery issues, such testing may be conducted when the patient is 40 years old, and then subsequently every 5 or 10 years to collect information on the patient's coronary arteries that may indicate changes to the coronary arteries that may indicate the onset of coronary artery issues/diseases.

In some implementations, compartmental ratios may be determined for coronary segments. For example, compartmental ratios of one or more of the right coronary artery proximal segment, the right coronary artery middle segment, right coronary artery distal segment, a posterior intraventricular branch of the right coronary artery, the left coronary artery (main stem), the interior intraventricular branch of the left coronary artery, the interior intraventricular branch of the left coronary artery middle segment, interior intraventricular branch left coronary artery distal segment, the first diagonal branch, the second diagonal branch, the circumflex branch of the left coronary artery proximal segment, the first marginal branch, circumflex branch of the left coronary artery middle segment, second marginal branch, the circumflex branch of the left coronary artery distal segment, the posterior left intraventricular branch the right coronary artery, and/or the intermediate atrial branch for the right coronary artery. In some implementations, compartmental ratios may be determined for any coronary vessels. Information relating to compartmental ratios that are determined for a patient may be presented on one or more paper or electronic reports, plots, graphs and the like. In some implementations, two or more compartmental ratios for a particular patient are determined and presented as a patient summation of compartmental ratios. For example, compartmental ratios of two or more portions of a patient's right coronary artery may be presented and report on a display to indicate the compartmental ratios of these portions of the right coronary artery. In some examples, compartmental ratios of all of the portions of the right coronary artery are determined presented for evaluation. In some examples, compartmental ratios of all the portions of the left coronary artery are determined and presented for evaluation. In some examples, compartmental ratios of corresponding parts of the left coronary artery and the right coronary artery are determined and presented for evaluation. Various embodiments of compartmental ratios can be included with any of the other information described herein to indicates plaque risk.

Figure 19:
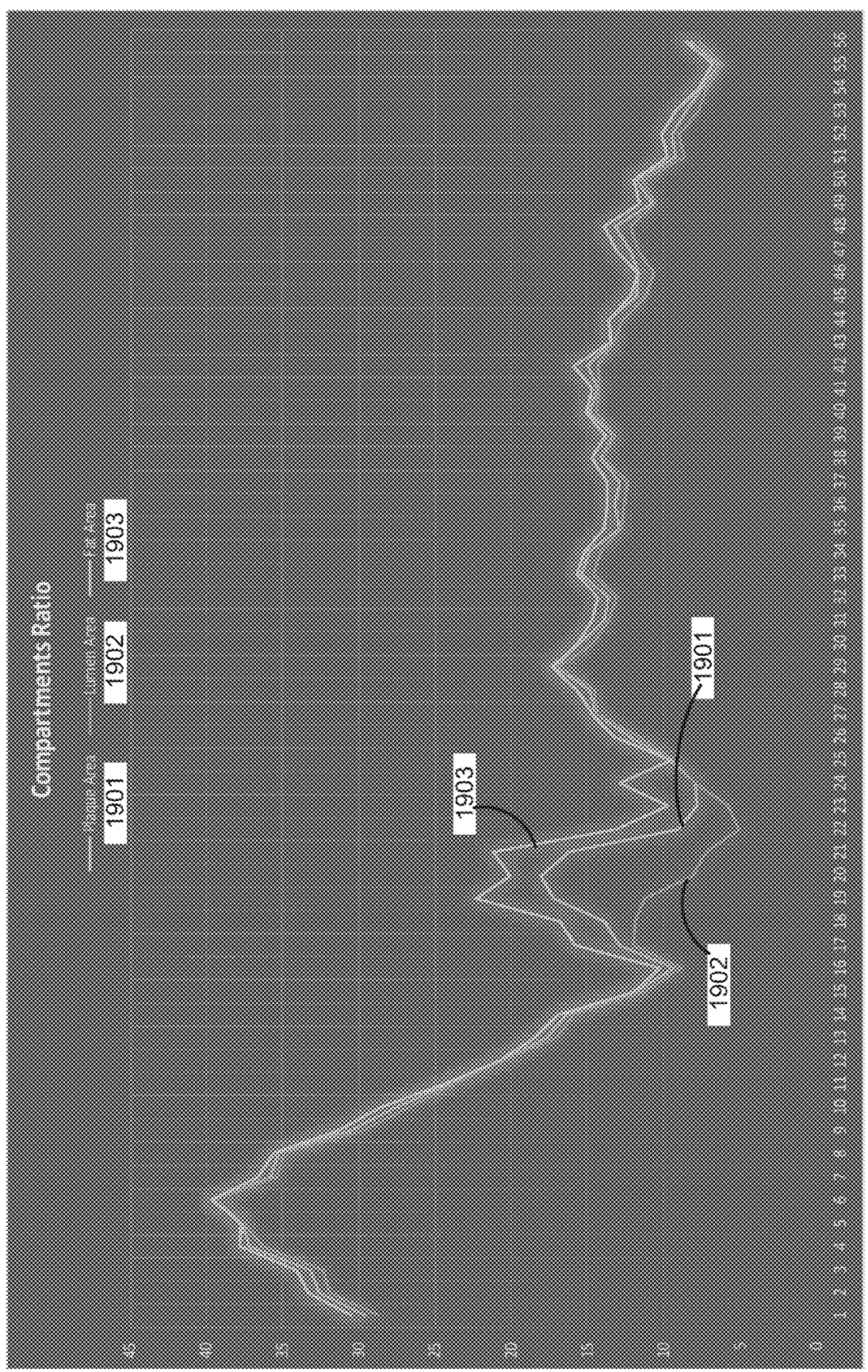
FIG. 19 is another chart of plots illustrating the compartment areas of cross-sections of plaque 1901, lumen 1902, and fat 1903 along the length of a coronary artery.

FIG. 19 is another chart of plots illustrating the compartment areas of cross-sections of plaque 1901, lumen 1902, and fat 1903 along the length of a coronary artery. Similar to FIG. 18, the distances of a measured cross-section of plaque, lumen, and fat from the ostium of a coronary artery are plotted on the x-axis, and areas of the respective cross-section of the plaque are plotted on the y-axis. The coronary artery in FIG. 19 illustrates an example of different compartmental ratios than the artery in FIG. 18.

Examples of Certain Embodiments

The following are non-limiting examples of certain embodiments of systems and methods of characterizing coronary plaque. Other embodiments may include one or more other features, or different features, that are discussed herein.

Embodiment 1: A method for characterization of coronary plaque tissue data and perivascular tissue data using image data gathered from a computed tomography (CT) scan along a blood vessel, the image information including radiodensity values of coronary plaque and perivascular tissue located adjacent to the coronary plaque, the method comprising: quantifying, in the image data, the radiodensity in regions of coronary plaque; quantifying, in the image data, radiodensity in at least one region of corresponding perivascular tissue adjacent to the coronary plaque; determining gradients of the quantified radiodensity values within the coronary plaque and the quantified radiodensity values within the corresponding perivascular tissue; determining a ratio of the quantified radiodensity values within the coronary plaque and the corresponding perivascular tissue; and characterizing the coronary plaque by analyzing one or more of: the gradients of the quantified radiodensity values in the coronary plaque and the corresponding perivascular tissue, or the ratio of the coronary plaque radiodensity values and the radiodensity values of the corresponding perivascular tissue, wherein the method is performed by one or more computer hardware processors configured to execute computer-executable instructions on a non-transitory computer storage medium.

Embodiment 2: The method of embodiment 1, wherein the perivascular tissue comprises at least one of coronary artery lumen, fat, coronary plaque or myocardium.

Embodiment 3: The method of any one of embodiments 1 and 2, further comprising receiving, via a network, the image data at a data storage component.

Embodiment 4: The method of embodiment 3, wherein the network is one of the Internet or a wide area network (WAN).

Embodiment 5: The method of any one of embodiments 1-4, wherein the image data from the CT scan includes at least ten images.

Embodiment 6: The method of any one of embodiments 1-4, wherein the image data from the CT scan includes at least 30 images.

Embodiment 7: The method of any one of embodiments 1-6, further comprising generating a patient report comprising at least one of a diagnosis, a prognosis, or a recommended treatment for a patient based on the characterization of the coronary plaque.

Embodiment 8: The method of any one of embodiments 1-7, wherein quantifying radiodensity in at least one region of perivascular tissue comprises quantifying radiodensity, of the scan information, for coronary plaque and adipose tissue in each of one or more regions or layers of perivascular tissue.

Embodiment 9: The method of any one of embodiments 1-8, wherein the radiodensity of the scan information is quantified for water in each of one or more of the regions of coronary plaque and perivascular tissue.

Embodiment 10: The method of any one of embodiments 1-9, wherein radiodensity of the scan information is quantified for low radiodensity plaque in the each of one or more regions or layers of coronary plaque.

Embodiment 11: The method of any one of embodiments 1-10, wherein the coronary plaque radiodensity values and the perivascular tissue radiodensity values are an average radiodensity.

Embodiment 12: The method of any one of embodiments 1-10, wherein the wherein the coronary plaque radiodensity values and the perivascular tissue radiodensity values are a maximum radiodensity.

Embodiment 13: The method of any one of embodiments 1-10, wherein the wherein the coronary plaque radiodensity values and the perivascular tissue radiodensity values are a minimum radiodensity.

Embodiment 14: The method of any one of embodiments 1-13, wherein the quantified radiodensities are transformed numerical radiodensity values of the image data.

Embodiment 15: The method of any one of embodiments 1-14, wherein the quantified radiodensities account for patient- and CT-specific parameters, including one or more of iodinated contrast agent, contrast type, injection rate, aortic contrast opacification, left ventricular blood pool opacification, signal-to-noise, contrast-to-noise, tube voltage, milliamps, method of cardiac gating, single and multiple energy image acquisition, CT scanner type, heart rate, heart rhythm, or blood pressure.

Embodiment 16: The method of any one of embodiments 1-15, further comprising reporting the quantified radiodensities of the coronary plaque and the perivascular tissue as a gradient.

Embodiment 17: The method of any one of embodiments 1 and 16, wherein the quantified radiodensities of the coronary plaque and the perivascular tissue are reported as a ratio of the slopes of the gradients from the coronary plaque to perivascular tissue adjacent to the coronary plaque.

Embodiment 18: The method of any one of embodiments 1-17, wherein the quantified radiodensities of the coronary plaque and the perivascular tissue are reported as the difference in radiodensity values from the coronary plaque to the perivascular tissue.

Embodiment 19: The method of any one of embodiments 1-18, wherein the image data is gathered from a CT scan along a length of at least one of a right coronary artery, left anterior descending artery, left circumflex artery, or their branches, or aorta, or carotid arteries, or femoral arteries, or renal arteries.

Embodiment 20: The method of any one of embodiments 1-18, wherein the data is gathered from a CT scan along a length of a non-coronary reference vessel.

Embodiment 21: The method of embodiment 20, wherein the non-coronary reference vessel is the aorta.

Embodiment 22: The method of any one of embodiments 1-21, wherein the radiodensity is quantified in Hounsfield units.

Embodiment 23: The method of any one of embodiments 1-21, wherein radiodensity is quantified in absolute material densities when multienergy CT is performed.

Embodiment 24: The method of any one of embodiments 1-24, wherein one or more regions or layers of perivascular tissue extend to an end distance from the outer wall of the blood vessel, the end distance being the fixed distance where the radiodensity of adipose tissue (i) reaches a minimum value within the scanned anatomical area in a healthy vessel, or (ii) drops by a relative percent (e.g., 10%); or (iii) drops by a relative percent versus a baseline radiodensity value in a vessel of the same type free of disease.

Embodiment 25: The method of any one of embodiments 1-25, wherein one or more regions or layers of the coronary plaque extend to an end distance from the outer wall of the blood vessel, the end distance being the fixed distance where the radiodensity of adipose tissue (i) reaches a maximum value within the plaque, or (ii) increases by a relative percent (e.g., 10%); (iii) or changes by a relative percent vs the lowest radiodensity value in the plaque.

Embodiment 26: The method of embodiment 24, wherein the baseline radiodensity value is the average radiodensity quantified in a layer of perivascular tissue lying within a fixed layer or region surrounding the outer vessel wall is measured by a thickness, area or volume.

Embodiment 27: The method of embodiment 24, wherein the baseline perivascular tissue radiodensity is the radiodensity quantified for adipose tissue in a layer of perivascular tissue lying proximal to the outer wall of the blood vessel.

Embodiment 28: The method of embodiment 24, wherein the baseline perivascular tissue radiodensity is the radiodensity quantified for water in a layer of perivascular tissue lying proximal to the outer wall of the blood vessel.

Embodiment 29: The method of embodiment 24, wherein the baseline radiodensity is an average radiodensity.

Embodiment 30: The method of embodiment 24, wherein the baseline radiodensity is a maximum radiodensity.

Embodiment 31: The method of embodiment 24, wherein the baseline radiodensity is a minimum radiodensity.

Embodiment 32: The method of embodiment 24, wherein the baseline radiodensity value is the average radiodensity quantified in a layer of coronary plaque tissue within a fixed layer or region within the plaque and is measured by a thickness, area or volume.

Embodiment 33: The method of embodiment 24, wherein the baseline coronary plaque radiodensity is the radiodensity quantified for all coronary plaques in the measured vessels.

Embodiment 34: The method of any one of embodiments 1-33, further comprising: determining a plot of the change in quantified radiodensity relative to baseline radiodensity in each of one or more concentric layers of perivascular tissue with respect to distance from the outer wall of the blood vessel up to an end distance; determining the area of the region bound by the plot of the change in quantified radiodensity and a plot of baseline radiodensity with respect to distance from the outer wall of the blood vessel up to the end distance; and dividing said area by the quantified radiodensity measured at a distance from the outer wall of the blood vessel, wherein the distance is less than the radius of the vessel or is a distance from the outer surface of the vessel above which the quantified radiodensity of adipose tissue drops by more than 5% compared to the baseline radiodensity of adipose tissue in a vessel of the same type free of disease.

Embodiment 35: The method of any one of embodiments 1-34, further comprising: determining a plot of the change in quantified radiodensity relative to baseline radiodensity in each of one or more concentric layers of coronary plaque tissue with respect to distance from the outer wall of the blood vessel up to the inner surface of the plaque; determining the area of the region bound by the plot of the change in quantified radiodensity and a plot of baseline radiodensity with respect to distance from the outer wall of the blood vessel up to the inner surface of the plaque; and dividing said area by the quantified radiodensity measured at a distance from the outer wall of the blood vessel, wherein the distance is less than the radius of the vessel or is a distance from the outer surface of the vessel above which the quantified radiodensity of adipose tissue drops by more than 5% compared to the baseline radiodensity of adipose tissue in a vessel of the same type free of disease.

Embodiment 36: The method of embodiment 25, wherein the quantified radiodensity is the quantified radiodensity of adipose tissue in the each of one or more regions or layers of perivascular tissue or coronary plaque.

Embodiment 37: The method of embodiment 25, wherein the quantified radiodensity is the quantified radiodensity of water in the each of one or more regions or layers of perivascular tissue.

Embodiment 38: The method of embodiment 25, wherein the quantified radiodensity is an average radiodensity.

Embodiment 39: The method of embodiment 25, wherein the quantified radiodensities are a maximum radiodensity.

Embodiment 40: The method of embodiment 25, wherein the perivascular tissue extends to an end distance from the outer wall of the blood vessel, the end distance being the fixed distance where the radiodensity of adipose tissue (i) reaches a minimum value within the scanned anatomical area in a healthy vessel; (ii) or drops by a relative percent (e.g., 10%); or (iii) drops by a relative percent vs the baseline radiodensity value in a vessel of the same type free of disease.

Embodiment 41: The method of any one of embodiments 1-40, wherein one or more regions or layers of coronary plaque tissue extend to an end distance from the outer wall of the blood vessel, the end distance being the fixed distance where the radiodensity of adipose tissue (i) reaches a maximum value within the plaque; or (ii) increases by a relative percent (e.g., 10%); (iii) or changes by a relative percent vs the lowest radiodensity value in the plaque.

Embodiment 42: The method of any one of embodiments 1-41, further comprising normalizing the quantified radiodensity of the coronary plaque and the perivascular tissue to CT scan parameters (patient- and CT-specific parameters), which include one or more of iodinated contrast agent, contrast type, injection rate, aortic contrast opacification, left ventricular blood pool opacification, signal-to-noise, contrast-to-noise, tube voltage, milliamps, method of cardiac gating, single and multiple energy image acquisition, CT scanner type, heart rate, heart rhythm, or blood pressure; normalize the quantified radiodensity of the coronary plaque-associated perivascular fat to remote perivascular fat; and normalize the quantified radiodensity of the coronary plaque to remote coronary plaques.

Embodiment 43: The method of any one of embodiments 1-42, further comprising quantifying other high risk plaque features, such as remodeling, volume, spotty calcifications, and further characterizing the high risk plaque based on one or more of the high risk plaque features.

Embodiment 44: The method of any one of the preceding embodiments, wherein characterizing the coronary plaque is based in part on plaque heterogeneity comprising calcium and non-calcified plaque admixtures.

Embodiment 45: The method of any one of the preceding embodiments, wherein characterizing the coronary plaque comprises identifying the coronary plaque as a high risk plaque if it is prone to be implicated as culprit lesions in future acute coronary events, based on comparison with previously classified patient image data.

Embodiment 46: The method of any one of the preceding embodiments, wherein characterizing the coronary plaque comprises identifying the coronary plaque as a high risk plaque if it is likely to cause ischemia based on a comparison with previously classified patient image data.

Embodiment 47: The method of any one of the preceding embodiments, wherein characterizing the coronary plaque comprises identifying the coronary plaque as a high risk plaque if it is likely to cause vasospasm based on a comparison with previously classified patient image data.

Embodiment 48: The method of any one of the preceding embodiments, wherein characterizing the coronary plaque comprises identifying the coronary plaque as a high risk plaque if it is likely to rapidly progress based on a comparisons with previously classified patient image data.

Embodiment 49: The method of any one of the preceding embodiments, wherein characterizing the coronary plaque comprises identifying the coronary plaque as a high risk plaque if it is likely not to calcify, based on a comparisons with previously classified patient image data.

Embodiment 50: The method of any one of the preceding embodiments, wherein characterizing the coronary plaque comprises identifying the coronary plaque as a high risk plaque if it is likely not to respond, regress or stabilize to medical therapy based on a comparisons with previously classified patient image data.

Embodiment 51: The method of any one of the preceding embodiments, wherein characterizing the coronary plaque comprises identifying the coronary plaque as a high risk plaque if it is associated with complications at the time of revascularization (such as by inducing no-reflow phenomenon) based on a comparisons with previously classified patient image data.

Embodiment 52: A system for volumetric characterization of coronary plaque tissue data and perivascular tissue data using image data gathered from one or more computed tomography (CT) scans along a blood vessel, the image information including radiodensity values of coronary plaque and perivascular tissue located adjacent to the coronary plaque, comprising: a first non-transitory computer storage medium configured to at least store the image data; a second non-transitory computer storage medium configured to at least store computer-executable instructions; and one or more computer hardware processors in communication with the second non-transitory computer storage medium, the one or more computer hardware processors configured to execute the computer-executable instructions to at least: quantify, in the image data, the radiodensity in regions of coronary plaque; quantify, in the image data, radiodensity in at least one region of corresponding perivascular tissue adjacent to the coronary plaque; determine gradients of the quantified radiodensity values within the coronary plaque and the quantified radiodensity values within the corresponding perivascular tissue; determine a ratio of the quantified radiodensity values within the coronary plaque and the corresponding perivascular tissue; and characterize the coronary plaque by analyzing one or more of: the gradients of the quantified radiodensity values in the coronary plaque and the corresponding perivascular tissue, or the ratio of the coronary plaque radiodensity values and the radiodensity values of the corresponding perivascular tissue.

Embodiment 53: A non-transitory computer readable medium comprising instructions that, when executed, cause an apparatus to perform a method comprising: quantifying, in the image data, the radiodensity in regions of coronary plaque; quantifying, in the image data, radiodensity in at least one region of corresponding perivascular tissue adjacent to the coronary plaque; determining gradients of the quantified radiodensity values within the coronary plaque and the quantified radiodensity values within the corresponding perivascular tissue; determining a ratio of the quantified radiodensity values within the coronary plaque and the corresponding perivascular tissue; and characterizing the coronary plaque by analyzing one or more of: the gradients of the quantified radiodensity values in the coronary plaque and the corresponding perivascular tissue, or the ratio of the coronary plaque radiodensity values and the radiodensity values of the corresponding perivascular tissue.

Embodiment 54: A system comprising a processor and a non-transient storage medium including processor executable instructions implementing a processing system for characterizing coronary plaque configured to: quantify, in the image data, radiodensity in regions of coronary plaque; quantify, in the image data, radiodensity in at least one region of corresponding perivascular tissue adjacent to the coronary plaque; characterize one or more medical conditions based on the quantified radiodensity properties of coronary plaque and the radiodensity in at least one region of corresponding perivascular tissue adjacent to the coronary plaque using at least one of a ratio of the quantified radiodensity values within the coronary plaque and the corresponding perivascular tissue, or at least one gradient of the quantified radiodensity values in the coronary plaque and the corresponding perivascular tissue.

Embodiment 55: A non-transitory computer readable medium comprising instructions that, when executed, cause an apparatus to perform a method comprising: quantifying, in the image data, radiodensity in regions of coronary plaque; quantifying, in the image data, radiodensity in at least one region of corresponding perivascular tissue adjacent to the coronary plaque; characterizing one or more medical conditions based on the quantified radiodensity properties of coronary plaque and the radiodensity in at least one region of corresponding perivascular tissue adjacent to the coronary plaque using at least one of a ratio of the quantified radiodensity values within the coronary plaque and the corresponding perivascular tissue, or at least one gradient of the quantified radiodensity values in the coronary plaque and the corresponding perivascular tissue.

Implementing Systems and Terminology

Implementations disclosed herein provide systems, methods and apparatus for mask-less phase detection autofocus. One skilled in the art will recognize that these embodiments may be implemented in hardware, software, firmware, or any combination thereof.

In some embodiments, the circuits, processes, and systems discussed above may be utilized in a wireless communication device, for example, a mobile wireless device. The wireless communication device may be a kind of electronic device used to wirelessly communicate with other electronic devices. Examples of wireless communication devices include cellular telephones, smart phones, Personal Digital Assistants (PDAs), e-readers, gaming systems, music players, netbooks, wireless modems, laptop computers, tablet devices, etc., for example, the mobile wireless device 130C (FIG. 1).

The wireless communication device may include one or more image sensors, one or more image signal processors, and a memory including instructions or modules for carrying out the process discussed above. The device may also have data, a processor loading instructions and/or data from memory, one or more communication interfaces, one or more input devices, one or more output devices such as a display device and a power source/interface. The wireless communication device may additionally include a transmitter and a receiver. The transmitter and receiver may be jointly referred to as a transceiver. The transceiver may be coupled to one or more antennas for transmitting and/or receiving wireless signals.

The wireless communication device may wirelessly connect to another electronic device (e.g., base station) to communicate information. For example, to communicate information received from the processing system 120 (FIG. 1) to/from another device 130 (FIG. 1). A wireless communication device may alternatively be referred to as a mobile device, a mobile station, a subscriber station, a user equipment (UE), a remote station, an access terminal, a mobile terminal, a terminal, a user terminal, a subscriber unit, etc. Examples of wireless communication devices include laptop or desktop computers, cellular phones, smart phones, tablet devices, etc. Wireless communication devices may operate in accordance with one or more industry standards. Thus, the general term "wireless communication device" or "mobile device" may include wireless communication devices described with varying nomenclatures according to industry standards (e.g., access terminal, user equipment (UE), remote terminal, etc.).

The functions described herein may be stored as one or more instructions on a processor-readable or computer-readable medium. For example, on the processing system 120 or any of the devices 130. The term "computer-readable medium" refers to any available medium that can be accessed by a computer or processor. By way of example, and not limitation, such a medium may comprise RAM, ROM, EEPROM, flash memory, CD-ROM or other optical disk storage, magnetic disk storage or other magnetic storage devices, or any other medium that can be used to store desired program code in the form of instructions or data structures and that can be accessed by a computer. Disk and disc, as used herein, includes compact disc (CD), laser disc, optical disc, digital versatile disc (DVD), floppy disk and Blu-ray® disc where disks usually reproduce data magnetically, while discs reproduce data optically with lasers. It should be noted that a computer-readable medium may be tangible and non-transitory. The term "computer-program product" refers to a computing device or processor in combination with code or instructions (e.g., a "program") that may be executed, processed or computed by the computing device or processor. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component or directly connected to the second component. As used herein, the term "plurality" denotes two or more. For example, a plurality of components indicates two or more components.

The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

In the foregoing description, specific details are given to provide a thorough understanding of the examples. However, it will be understood by one of ordinary skill in the art that the examples may be practiced without these specific details. For example, electrical components/devices may be shown in block diagrams in order not to obscure the examples in unnecessary detail. In other instances, such components, other structures and techniques may be shown in detail to further explain the examples. Thus, the present invention is not intended to be limited to the implementations shown herein but is to be accorded the widest scope consistent with the principles and novel features disclosed herein.

What is claimed is:

1. A computer-implemented method for characterization of coronary plaque by analyzing metrics generated from radiodensity values of coronary plaque and radiodensity values of perivascular tissue located adjacent to the coronary plaque of a patient and previously stored metrics generated from radiodensity values of coronary plaque and radiodensity values of perivascular tissue located adjacent to the coronary plaque of other people, the method comprising:
   generating image information for the patient, the image information including image data of computed tomography (CT) scans along a vessel of the patient, the image data having radiodensity values of coronary plaque and radiodensity values of perivascular tissue located adjacent to the coronary plaque, wherein generating the image information includes
      accessing CT scan parameters stored for the patient in a database, the CT scan parameters including
      one or more of a CT scanner type, CT scanner tube amperage, or CT scanner peak tube voltage of the CT scanner used to generate the CT scans,
      one or more of the CT scanner noise, CT scanner signal-to-noise ratio, or CT scanner contrast-to-noise ratio of the CT scanner used to generate the CT scans,
      one or more of contrast type used in the patient for the CT scans, or an injection rate of the contrast into the patient, and
      one or more of the patient's heart rate or the patient's blood pressure when the CT scans were generated; and
      automatically determining radiodensity values of coronary plaque and radiodensity values of perivascular tissue in the image accounting for the CT scan parameters;
   determining, based on applying a machine learning algorithm to the image information, coronary plaque information of the patient, wherein determining the coronary plaque information comprises
      quantifying, using the image information, radiodensity values in a region of coronary plaque of the patient,
      quantifying, using the image information, radiodensity values in a region of perivascular tissue adjacent to the region of coronary plaque of the patient, and
      generating metrics of coronary plaque of the patient using the quantified radiodensity values in the region of coronary plaque and the quantified radiodensity values in the region of perivascular tissue adjacent to the region of coronary plaque;
   accessing a database of coronary plaque information and characteristics of other people, the coronary plaque information in the database including metrics generated from radiodensity values of a region of coronary plaque in the other people and radiodensity values of perivascular tissue adjacent to the region of coronary plaque in the other people, and the characteristics of the other people including information at least of age, sex, race, diabetes, smoking, and prior coronary artery disease; and
   characterizing the coronary plaque information of the patient by comparing the metrics of the coronary plaque information and characteristics of the patient to the metrics of the coronary plaque information of other people in the database having one or more of the same characteristics, wherein characterizing the coronary plaque information includes identifying the coronary plaque as a high risk plaque,
   wherein the method is performed by one or more computer hardware processors configured to execute computer-executable instructions on a non-transitory computer storage medium.

2. The method of claim 1, wherein generating metrics using the quantified radiodensity values in the region of coronary plaque and the quantified radiodensity values in a region of perivascular tissue adjacent to the region of the patient comprises determining, along a line, a slope value of the radiodensity values of the coronary plaque and a slope value of the radiodensity values of the perivascular tissue adjacent to the coronary plaque.

3. The method of claim 2, wherein generating metrics further comprises determining a ratio of the slope value of the radiodensity values of the coronary plaque and a slope value of the radiodensity values of the perivascular tissue adjacent to the coronary plaque.

4. The method of claim 1, wherein generating metrics using the quantified radiodensity values in the region of coronary plaque and the quantified radiodensity values in a region of perivascular tissue adjacent to the region of the patient comprises generating, using the image information, a ratio between quantified radiodensity values of the coronary plaque and quantified radiodensity values of the corresponding perivascular tissue.

5. The method of claim 1, wherein the perivascular tissue is perivascular fat, and generating metrics using the quantified radiodensity values in the region of coronary plaque and the quantified radiodensity values in the region of perivascular tissue adjacent to the region of coronary plaque of the patient comprises generating a ratio of a density of the coronary plaque and a density of the perivascular fat.

6. The method of claim 1, wherein the perivascular tissue is a coronary artery, and generating metrics using the quantified radiodensity values in the region of coronary plaque and the quantified radiodensity values in the region of perivascular tissue adjacent to the region of coronary plaque of the patient comprises generating a ratio of a density of the coronary plaque and a density of the coronary artery.

7. The method of claim 5, wherein generating the ratio comprises generating the ratio of a maximum radiodensity value of the coronary plaque and a maximum radiodensity value of the perivascular fat.

8. The method of claim 5, wherein generating the ratio comprises generating a ratio of a minimum radiodensity value of the coronary plaque and a minimum radiodensity value of the perivascular fat.

9. The method of claim 5, wherein generating the ratio comprises generating a ratio of a maximum radiodensity value of the coronary plaque and a minimum radiodensity value of the perivascular fat.

10. The method of claim 5, wherein generating the ratio comprises generating a ratio of a minimum radiodensity value of the coronary plaque and a maximum radiodensity value of the perivascular fat.

11. The method of claim 1, wherein the characteristics of the patient comprise information of age, sex, race, blood pressure, diabetes, smoking, and prior coronary artery disease.

12. The method of claim 11, wherein the database includes coronary plaque information and characteristics of numerous other people.

13. The method of claim 1, wherein characterizing the coronary plaque comprises identifying the coronary plaque as a high risk plaque if it is likely to cause ischemia based on a comparison of the coronary plaque information and characteristics of the patient to the coronary plaque information and characteristics of the other people in the database.

14. The method of claim 1, wherein characterizing the coronary plaque comprises identifying the coronary plaque as a high risk plaque if it is likely to cause vasospasm based on a comparison of the coronary plaque information and characteristics of the patient to the coronary plaque information and characteristics of the other people in the database.

15. The method of claim 1, wherein characterizing the coronary plaque comprises identifying the coronary plaque as a high risk plaque if it is likely to rapidly progress based on a comparison of the coronary plaque information and characteristics of the patient to the coronary plaque information and characteristics of the other people in the database.

16. A system for characterization of coronary plaque tissue data and perivascular tissue data using image data gathered from one or more computed tomography (CT) scans along a blood vessel, the image data including radiodensity values of coronary plaque and perivascular tissue located adjacent to the coronary plaque, the system comprising:

a first non-transitory computer storage medium configured to store (i) a database of coronary plaque information and characteristics of other people, the coronary plaque information including metrics generated from radiodensity values in coronary plaque and radiodensity values of perivascular tissue adjacent to the coronary plaque, and (ii) image information including image data of computed tomography (CT) scans along a vessel of a patient, the image data having radiodensity values of coronary plaque and radiodensity values of perivascular tissue located adjacent to the coronary plaque;

a second non-transitory computer storage medium configured to at least store computer-executable instructions; and one or more computer hardware processors in communication with the second non-transitory computer storage medium, the one or more computer hardware processors configured to execute the computer-executable instructions to:

generate the image information and storing the image information on the first non-transitory computer storage medium, wherein generating the image information includes accessing CT scan parameters stored for the patient in a database, the CT scan parameters including one or more of a CT scanner type, CT scanner tube amperage, or CT scanner peak tube voltage of the CT scanner used to generate the CT scans, one or more of the CT scanner noise, CT scanner signal-to-noise ratio, or CT scanner contrast-to-noise ratio of the CT scanner used to generate the CT scans, one or more of contrast type used in the patient for the CT scans, or an injection rate of the contrast into the patient, and one or more of the patient's heart rate or the patient's blood pressure when the CT scans were generated; and automatically determining radiodensity values of coronary plaque and radiodensity values of perivascular tissue in the image accounting for the CT scan parameters;

determine, based on applying a machine learning algorithm to the image information, coronary plaque information of the patient, wherein determining the coronary plaque information comprises quantifying, using the image information, radiodensity values in a region of coronary plaque of the patient, quantifying, using the image information, radiodensity values in a region of perivascular tissue adjacent to the region of coronary plaque of the patient, and generating metrics using the quantified radiodensity values in the region of coronary plaque and the quantified radiodensity values in the region of perivascular tissue adjacent to the region of the patient; and characterize the coronary plaque information of the patient by comparing the metrics of the coronary plaque information and characteristics of the patient to the metrics of the coronary plaque information and characteristics of other people in the database, wherein characterizing the coronary plaque information of the patient includes identifying the coronary plaque as a high risk plaque.

17. The system of claim 16, wherein the one or more computer hardware processors are further configured to execute the computer-executable instructions to generate the metrics using the quantified radiodensity values in the region of coronary plaque and the quantified radiodensity values in a region of perivascular tissue adjacent to the region of the patient by determining, along a line, a slope value of the radiodensity values of the coronary plaque and a slope value of the radiodensity values of the perivascular tissue adjacent to the coronary plaque.

18. The system of claim 16, wherein the one or more computer hardware processors are further configured to execute the computer-executable instructions to generate the metrics by determining a ratio of the slope value of the radiodensity values of the coronary plaque and a slope value of the radiodensity values of the perivascular tissue adjacent to the coronary plaque.

19. The system of claim 16, wherein the one or more computer hardware processors are further configured to execute the computer-executable instructions to generating the metrics using the quantified radiodensity values in the region of coronary plaque and the quantified radiodensity values in a region of perivascular tissue adjacent to the region of the patient by generating, using the image information, a ratio between quantified radiodensity values of the coronary plaque and quantified radiodensity values of the corresponding perivascular tissue.

20. The system of claim 16, wherein the perivascular tissue is perivascular fat, and generating metrics using the quantified radiodensity values in the region of coronary plaque and the quantified radiodensity values in the region of perivascular tissue adjacent to the region of coronary plaque of the patient comprises generating a ratio of a density of the coronary plaque and a density of the perivascular fat.

21. The system of claim 16, wherein the perivascular tissue is a coronary artery, and generating metrics using the quantified radiodensity values in the region of coronary plaque and the quantified radiodensity values in the region of perivascular tissue adjacent to the region of coronary plaque of the patient comprises generating a ratio of a density of the coronary plaque and a density of the coronary artery.

22. The system of claim 21, wherein the ratio is one of a ratio of a maximum radiodensity value of the coronary plaque and a maximum radiodensity value of the perivascular fat, a ratio of a minimum radiodensity value of the coronary plaque and a minimum radiodensity value of the perivascular fat, a ratio of a maximum radiodensity value of the coronary plaque and a minimum radiodensity value of the perivascular fat, or
a ratio of a minimum radiodensity value of the coronary plaque and a maximum radiodensity value of the perivascular fat.

23. The system of claim 16, wherein the characteristics of the patient comprise information of age, sex, race, blood pressure, diabetes, smoking, and prior coronary artery disease.

24. The system of claim 16, wherein the database includes coronary plaque information and characteristics of thousands of other people.

25. A non-transitory computer readable medium comprising instructions that, when executed by one or more processors, cause an apparatus to perform a method for characterization of coronary plaque and perivascular tissue using (i) a database of coronary plaque information and characteristics of other people, the coronary plaque information including metrics generated from radiodensity values in coronary plaque and radiodensity values of perivascular tissue adjacent to the coronary plaque, and using (ii) image information including image data of computed tomography (CT) scans along a vessel of a patient, the image data having radiodensity values of coronary plaque and radiodensity values of perivascular tissue located adjacent to the coronary plaque, the method comprising:
generating the image information and storing the image information on the first non-transitory computer storage medium, wherein generating the image information includes
accessing CT scan parameters stored for the patient in a database, the CT scan parameters including
one or more of a CT scanner type, CT scanner tube amperage, or CT scanner peak tube voltage of the CT scanner used to generate the CT scans,
one or more of the CT scanner noise, CT scanner signal-to-noise ratio, or CT scanner contrast-to-noise ratio of the CT scanner used to generate the CT scans,
one or more of contrast type used in the patient for the CT scans, or an injection rate of the contrast into the patient, and
one or more of the patient's heart rate or the patient's blood pressure when the CT scans were generated; and
automatically determining radiodensity values of coronary plaque and radiodensity values of perivascular tissue in the image accounting for the CT scan parameters;
determining, based on applying a machine learning algorithm to the image information, coronary plaque information of the patient, wherein determining the coronary plaque information comprises
quantifying, using the image information, radiodensity values in a region of coronary plaque of the patient,
quantifying, using the image information, radiodensity values in a region of perivascular tissue adjacent to the region of coronary plaque of the patient, and
generating metrics using the quantified radiodensity values in the region of coronary plaque and the quantified radiodensity values in the region of perivascular tissue adjacent to the region of the patient; and
characterizing the coronary plaque information of the patient by comparing the metrics of the coronary plaque information and characteristics of the patient to the metrics of the coronary plaque information and characteristics of other people in the database, wherein characterizing the coronary plaque information of the patient includes identifying the coronary plaque as a high risk plaque.

26. The non-transitory computer readable medium of claim 25, wherein generating metrics using the quantified radiodensity values in the region of coronary plaque and the quantified radiodensity values in a region of perivascular tissue adjacent to the region of the patient comprises determining, along a line, a slope value of the radiodensity values of the coronary plaque and a slope value of the radiodensity values of the perivascular tissue adjacent to the coronary plaque.

27. The non-transitory computer readable medium of claim 26, wherein generating metrics further comprises determining a ratio of the slope value of the radiodensity values of the coronary plaque and a slope value of the radiodensity values of the perivascular tissue adjacent to the coronary plaque.

28. The non-transitory computer readable medium of claim 26, wherein generating metrics using the quantified radiodensity values in the region of coronary plaque and the quantified radiodensity values in a region of perivascular tissue adjacent to the region of the patient comprises generating, using the image information, a ratio between quantified radiodensity values of the coronary plaque and quantified radiodensity values of the corresponding perivascular tissue.

29. The non-transitory computer readable medium of claim 26, wherein the characteristics of the patient and the other people comprise information of age, sex, race, blood pressure, diabetes, smoking, and prior coronary artery disease.

30. The non-transitory computer readable medium of claim 26, wherein the database includes coronary plaque information and characteristics of numerous other people.

\* \* \* \* \*

UNITED STATES PATENT AND TRADEMARK OFFICE
CERTIFICATE OF CORRECTION

PATENT NO. : 11,317,883 B2
APPLICATION NO. : 17/461587
DATED : May 3, 2022
INVENTOR(S) : James K. Min It is certified that error appears in the above-identified patent and that said Letters Patent is hereby corrected as shown below:

On the Title Page

Page 4, Column 1 (item (56) Other Publications), Line 8, delete "vunerability" and insert --vulnerability--.

Page 4, Column 1 (item (56) Other Publications), Line 33, delete "JACCL" and insert --JACC--.

Page 4, Column 1 (item (56) Other Publications), Line 46, delete "Amercan Heart Assocation," and insert --American Heart Association,--.

Page 4, Column 1 (item (56) Other Publications), Line 54, delete "Predictiong" and insert --Predicting--.

Page 4, Column 1 (item (56) Other Publications), Line 63, delete "Halftsone" and insert --Halftone--.

Page 4, Column 2 (item (56) Other Publications), Line 22, delete "professinals" and insert --professionals--.

Page 4, Column 2 (item (56) Other Publications), Line 68, delete "Cardivasc" and insert --Cardiovasc--.

Page 4, Column 2 (item (56) Other Publications), Line 70, delete "Quantatitive" and insert --Quantitative--.

Page 5, Column 1 (item (56) Other Publications), Line 7, delete "Quantitiative" and insert --Quantitative--.

Page 5, Column 1 (item (56) Other Publications), Line 15, delete "Instanteous" and insert --Instantaneous--.

Signed and Sealed this
Thirteenth Day of September, 2022

Katherine Kelly Vidal
*Director of the United States Patent and Trademark Office*

CERTIFICATE OF CORRECTION (continued)
U.S. Pat. No. 11,317,883 B2

Page 5, Column 1 (item (56) Other Publications), Line 19, delete "Franctional" and insert --Fractional--.

Page 5, Column 1 (item (56) Other Publications), Line 22-23, delete "Non-invasice" and insert --Non-invasive--.

Page 5, Column 1 (item (56) Other Publications), Line 37, delete "Statble" and insert --Stable--.

Page 5, Column 2 (item (56) Other Publications), Line 17, delete "2016." and insert --2016].--.

Page 5, Column 2 (item (56) Other Publications), Line 20, delete "Progostic" and insert --Prognostic--.

Page 5, Column 2 (item (56) Other Publications), Line 26, delete "clas" and insert --class--.

Page 5, Column 2 (item (56) Other Publications), Line 45, delete "(AIRC)" and insert --(ARIC)--.

Page 5, Column 2 (item (56) Other Publications), Line 64, delete "ariability" and insert --variability--.

Page 6, Column 1 (item (56) Other Publications), Line 28, delete "(Progession" and insert --(Progression--.

Page 6, Column 1 (item (56) Other Publications), Line 35, delete "Progession" and insert --Progression--.

Page 6, Column 2 (item (56) Other Publications), Line 35, delete "Evalution" and insert --Evaluation--.

Page 6, Column 2 (item (56) Other Publications), Line 44, delete "(35:" and insert --(35):--.

Page 6, Column 2 (item (56) Other Publications), Line 71, delete "indentification" and insert --identification--.

Page 7, Column 1 (item (56) Other Publications), Line 51, delete "Tomorgraphy" and insert --Tomography--.

Page 7, Column 1 (item (56) Other Publications), Line 55, delete "Toogr," and insert --Tomogr,--.

Page 7, Column 1 (item (56) Other Publications), Line 57, delete "plaqie" and insert --plaque--.

Page 7, Column 1 (item (56) Other Publications), Line 60, delete "Reproductibility" and insert --Reproducibility--.

Page 7, Column 2 (item (56) Other Publications), Line 29, delete "departement."" and insert --department."--.

Page 7, Column 2 (item (56) Other Publications), Line 39, delete "Three-Dimentional" and insert --Three-Dimensional--.

Page 7, Column 2 (item (56) Other Publications), Line 40, delete "Transactons" and insert --Transactions--.

Page 7, Column 2 (item (56) Other Publications), Line 49, delete "Circuliation," and insert --Circulation,--.

Page 7, Column 2 (item (56) Other Publications), Line 51, delete ""Nonivasive elalusation" and insert --"Noninvasive evaluation--.

Page 7, Column 2 (item (56) Other Publications), Line 51, delete "desease:" and insert --disease:--.

Page 8, Column 1 (item (56) Other Publications), Line 1, delete "trail" and insert --trial--.

Page 8, Column 1 (item (56) Other Publications), Line 3, delete "JAAC" and insert --JACC--.

Page 8, Column 1 (item (56) Other Publications), Line 14, delete "Heatlh" and insert --Health--.

Page 8, Column 1 (item (56) Other Publications), Line 19, delete "stucy" and insert --study--.

Page 8, Column 2 (item (56) Other Publications), Line 9, delete "diseae" and insert --disease--.

Page 8, Column 2 (item (56) Other Publications), Line 13, delete "hemorrage."" and insert --hemorrhage."--.

Page 8, Column 2 (item (56) Other Publications), Line 24, delete "progession" and insert --progression--.

Page 8, Column 2 (item (56) Other Publications), Line 29, delete "Chracteristics" and insert --Characteristics--.

Page 8, Column 2 (item (56) Other Publications), Line 42, delete "Imaging)" and insert --Imaging--.

Page 8, Column 2 (item (56) Other Publications), Line 44, delete "quanititive" and insert --quantitative--.

Page 8, Column 2 (item (56) Other Publications), Line 50, delete "Cardiocascular" and insert --Cardiovascular--.

In the Drawings

Sheet 5 of 21 (Reference Numeral 480) (FIG. 4B), and on the Title Page, the illustrative figure, Line 3, delete "PERIVSCULAR" and insert --PERIVASCULAR--.

CERTIFICATE OF CORRECTION (continued)
U.S. Pat. No. 11,317,883 B2

Sheet 6 of 21 (Reference Numeral 515) (FIG. 5A), Line 2, delete "ARTIERIES" and insert --ARTERIES--.

Sheet 7 of 21 (Reference Numeral 555) (FIG. 5B), Line 1, delete "QUANTFYING" and insert --QUANTIFYING--.

Sheet 8 of 21 (Reference Numeral 625) (FIG. 6), Line 2, delete "JUXAPOSED" and insert --JUXTAPOSED--.

Sheet 8 of 21 (Reference Numeral 615) (FIG. 6), Line 2, delete "ATTNUATION" and insert --ATTENUATION--.

Sheet 9 of 21 (Reference Numeral 625) (FIG. 7), Line 2, delete "JUXAPOSED" and insert --JUXTAPOSED--.

Sheet 9 of 21 (Reference Numeral 615) (FIG. 7), Line 2, delete "ATTNUATION" and insert --ATTENUATION--.

Sheet 13 of 21 (Reference Numeral 951) (FIG. 11), Line 1, delete "CARDIODENSITY" and insert --RADIODENSITY--.

Sheet 13 of 21 (Reference Numeral 951) (FIG. 11), Line 3, delete "UNTS)" and insert --UNITS)--.

Sheet 13 of 21 (Reference Numeral 961) (FIG. 11), Line 1, delete "CARDIODENSITY" and insert --RADIODENSITY--.

Sheet 13 of 21 (Reference Numeral 961) (FIG. 11), Line 3, delete "UNTS)" and insert --UNITS)--.

Sheet 14 of 21 (Reference Numeral 1231) (FIG. 12), Line 1, delete "CARDIODENSITY" and insert --RADIODENSITY--.

Sheet 14 of 21 (Reference Numeral 1231) (FIG. 12), Line 3, delete "UNTS)" and insert --UNITS)--.

Sheet 14 of 21 (Reference Numeral 1241) (FIG. 12), Line 1, delete "CARDIODENSITY" and insert --RADIODENSITY--.

Sheet 14 of 21 (Reference Numeral 1241) (FIG. 12), Line 3, delete "UNTS)" and insert --UNITS)--.

In the Specification

Column 2, Line 8, delete "SYNAX" and insert --SYNTAX--.

Column 4, Line 10, delete "plaque" and insert --plaque.--.

Column 8, Line 44, delete "arteries" and insert --arteries.--.

Column 11, Line 48, delete "(e.g.," and insert --e.g.,--.

Column 11, Line 52, delete "artery):" and insert --artery);--.

Column 11, Line 67, delete "value" and insert --value.--.

Column 12, Line 8, delete "attenuation" and insert --attenuation.--.

Column 12, Line 11, delete "plaque" and insert --plaque.--.

Column 15, Line 40, delete "(for" and insert --for--.

Column 15, Line 47, delete "(MM)" and insert --(MRI)--.

Column 23, Line 40, delete "and or" and insert --and/or--.

Column 27, Line 48-49, delete "of the of the" and insert --of the--.

Column 28, Line 56, delete "value" and insert --value.--.

Column 28, Line 64, delete "attenuation" and insert --attenuation.--.

Column 28, Line 67, delete "plaque" and insert --plaque.--.

Column 33, Line 13, delete "{34:30}:" and insert --{34:30};--.

Column 36, Line 65, delete "may it may" and insert --may--.

Column 40, Line 16 (approx.), delete "10%);" and insert --≥10%);--.

Column 40, Line 25, delete "10%);" and insert --≥10%);--.

Column 41, Line 40, delete "10%);" and insert --≥10%);--.

Column 41, Line 49, delete "10%);" and insert --≥10%);--.